US007223597B2

(12) United States Patent
Simmons et al.

(10) Patent No.: US 7,223,597 B2
(45) Date of Patent: May 29, 2007

(54) ANTI-APOPTOSIS GENES AND METHODS OF USE THEREOF

(75) Inventors: Carl R. Simmons, Des Moines, IA (US); William J. Gordon-Kamm, Urbandale, IA (US); Gurmukh S. Johal, West Lafayette, IN (US); Pedro A. Navarro Acevedo, Ames, IA (US); Yumin Tao, Urbandale, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 213 days.

(21) Appl. No.: 10/167,015

(22) Filed: Jun. 11, 2002

(65) Prior Publication Data

US 2003/0056249 A1 Mar. 20, 2003

Related U.S. Application Data

(60) Provisional application No. 60/297,478, filed on Jun. 12, 2001.

(51) Int. Cl.
*C12N 15/82* (2006.01)
*C12N 15/29* (2006.01)
(52) U.S. Cl. .................... 435/419; 536/23.6; 435/320.1
(58) Field of Classification Search ............. 435/320.1, 435/252.3, 419; 536/23.6; 800/290, 298
See application file for complete search history.

(56) References Cited

U.S. PATENT DOCUMENTS

| | | | |
|---|---|---|---|
| 6,211,437 B1* | 4/2001 | Briggs et al. | ................ 800/298 |
| 6,310,273 B1 | 10/2001 | Gilchrist et al. | ............ 800/279 |
| 2003/0008785 A1 | 1/2003 | Reed | |

FOREIGN PATENT DOCUMENTS

| | | |
|---|---|---|
| WO | WO 00/09664 | 2/2000 |
| WO | WO 00/26391 | 5/2000 |
| WO | WO 01/59108 A2 | 8/2001 |
| WO | WO 01/66696 A2 | 9/2001 |
| WO | WO 02/22822 A2 | 3/2002 |

OTHER PUBLICATIONS

Broun et al. Catalytic plasticity of fatty acid modification enzymes underlying chemical diversity of plant lipids. Science. 1998 N 13;282(5392):1315-7.*
Holinger et al. Bak BH3 peptides antagonize Bcl-xL function and induce apoptosis through cytochrome c-independent activatio of caspases. J Biol Chem. May 7, 1999;274(19):13298-304.*
Kawai et al. Evolutionarily conserved plant homologue of the Bax inhibitor-1 (Bl-1) gene capable of supressing Bax-induced ce death in yeast(1). FEBS Lett. Dec. 31, 1999;464(3):143-7.*
Kawai et al., Oryza sativa Bl-1 mRNA for Bax inhibitor-1, complete cds. GenBank Accession No. AB025926, Mar. 4, 2000.*
Mittler R. et al. Inhibition of Programmed Cell Death in Tobacco Plants during a Pathogen-Induced Hypersensitive Response at Low Oxygen Pressure. Plant Cell. Nov. 1996;8(11):1991-20.*
Segal et al. Zinc fingers and a green thumb: manipulating gene expression in plants. Curr Opin Plant Biol. Apr. 2003;6(2):163-8. Review.*
Cotter et al., "Cell death (apoptosis) in cell culture systems", (1995) *TIBTECH* 13:150-155.
Kawai-Yamada et al., "Mammalian Bax-induced plant cell death can be down-regulated by overexpression of *Arabidopsis Bax Inhibitor-1* (AtBI-1)", (2001) *Plant Biology* 98(21):12295-12300.
Mitsuhara et al., "Animal cell-death suppressors BcI-$x_L$ and Ced-9 inhibit cell death in tobacco plants", (1999) *Current Biology* 9(14):775-778.
Oltvai et al., "BcI-2 Heterodimerizes In Vivo with a Conserved Homolog, Bax, That Accelerates Programmed Cell Death", (1993) *Cell* 74:609-619.
Pennell et al., "Programmed Cell Death in Plants" (1997) Plant *Cell* 9:1157-1168.
Sanchez et al., "AtBI-1, a plant homologue of Bax Inhibitor-1, suppresses Bax-induced cell death in yeast and is rapidly upregulated during wounding and pathogen challenge", *Plant Journal* 21(4):393-399.
Wei et al., "Proapoptotic BAX and BAK: A Requisite Gateway to Mitochondiral Dysfunction and Death", (2001) *Science* 292:727-730.
GAP Nucleotide Comparisons of the Seven Maize Bax Inhibitor Genes to Each other using Nucleotide Coding Regions; 26 pages.
BLAST results of *Zea mays* Bax Inhibitor (Zm-BI) genes with public sequence databases (NR, NT, public EST, and GeneSeq); 31 pages.
GAP DNA Sequence Alignment Analysis; 9 pages.
GAP DNA Sequence Alignment Analysis; 11 pages.
GAP DNA Sequence Alignment Analysis; 47 pages.
Kawai et al., Evolutionarily conserved plant homologue of the Bax Inhibitor-1 (Bl-1) gene capable of supressing Bax-induced cell death in yeast, FEBS Letters 464 (1999) 143-147.
Database Gen Bank Accession No. BG321220, Singh et al., Expressed Sequence Tags from Cold-Stressed maize Seedlings, Gene Sequence (Feb. 27, 2001).
Database GenBank Accession No. AB025926, Kawat et al., Evolutionally conserved plant homologue of the BAX inhibitor-1 (BI-1) gene capable of suppressing Bax-induced cell death in yeast, Gene Sequence (Mar. 4, 2000).

* cited by examiner

*Primary Examiner*—Cynthia Collins

(57) ABSTRACT

The invention provides isolated nucleic acids and their encoded proteins that act as cell death inhibitors and methods of use thereof. The invention further provides expression cassettes, transformed host cells, transgenic plants and plant parts, and antibody compositions.

3 Claims, No Drawings

```
                            SEQUENCE LISTING

<160> NUMBER OF SEQ ID NOS: 34

<210> SEQ ID NO 1
<211> LENGTH: 957
<212> TYPE: DNA
<213> ORGANISM: Zea mays
<220> FEATURE:
<221> NAME/KEY: CDS
<222> LOCATION: (72)...(823)

<400> SEQUENCE: 1
aagcaattct ccaaattagg gtttctttcc gcttgctttc cagtttgcgg catcagtcgg      60
tggcgcctgc g atg gag tct ctg ttc ggc caa tcg cag cgg agg agg agg    110
            Met Glu Ser Leu Phe Gly Gln Ser Gln Arg Arg Arg Arg
              1               5                  10 gcg ggc ggc agc ggc ttc gaa tcg ctc aag cgt ctg ggt cac atc tca     158
Ala Gly Gly Ser Gly Phe Glu Ser Leu Lys Arg Leu Gly His Ile Ser
         15                  20                  25 ccc gct gtg cag tcc cac ctc aaa cat gtg tac ctc acc cta tgc tcc     206
Pro Ala Val Gln Ser His Leu Lys His Val Tyr Leu Thr Leu Cys Ser
 30                  35                  40                  45 gcg ctg gcc ttc tct gca ctc ggc gcg tac ctc cac atc ctc ctc aac     254
Ala Leu Ala Phe Ser Ala Leu Gly Ala Tyr Leu His Ile Leu Leu Asn
                 50                  55                  60 gtc gga ggc gcc ctc acg acc gtg gga tgc gtg gcc tcc atc gcc ttc     302
Val Gly Gly Ala Leu Thr Thr Val Gly Cys Val Ala Ser Ile Ala Phe
             65                  70                  75 ctc atc tcc ctg ccc gct tca cgg gac cag gag agg aac cgc ttg gcg     350
Leu Ile Ser Leu Pro Ala Ser Arg Asp Gln Glu Arg Asn Arg Leu Ala
         80                  85                  90 ctg ctc atg tct gcc gcg ctc ctt caa ggc gcg tcc gtt ggt ccg ctc     398
Leu Leu Met Ser Ala Ala Leu Leu Gln Gly Ala Ser Val Gly Pro Leu
```

-continued

```
              95                  100                 105
gtc gac ctt gtt att gac ttg gat tcg agg att ctc gtc act gcg ttc    446
Val Asp Leu Val Ile Asp Leu Asp Ser Arg Ile Leu Val Thr Ala Phe
110                 115                 120                 125 gtc ggg acc gca gtt gct ttt gca tgc ttc tct ggc gct gcc atc atc    494
Val Gly Thr Ala Val Ala Phe Ala Cys Phe Ser Gly Ala Ala Ile Ile
            130                 135                 140 gcc aag cgc agg gaa tac ctg tac ctc ggc ggt ctg ctt tca tct ggc    542
Ala Lys Arg Arg Glu Tyr Leu Tyr Leu Gly Gly Leu Leu Ser Ser Gly
        145                 150                 155 ctc tcc att ctt ctc tgg ctg cag ttt gct act tca atc ttt ggc cac    590
Leu Ser Ile Leu Leu Trp Leu Gln Phe Ala Thr Ser Ile Phe Gly His
    160                 165                 170 acc agc gcg acc ttc atg ttt gag ctc tac ttt ggc ctc ctg gtt ttc    638
Thr Ser Ala Thr Phe Met Phe Glu Leu Tyr Phe Gly Leu Leu Val Phe
        175                 180                 185 ctg gga tat atg gtg ttt gac acc cag gag atc atc gag agg gcg cac    686
Leu Gly Tyr Met Val Phe Asp Thr Gln Glu Ile Ile Glu Arg Ala His
190                 195                 200                 205 cgt ggg gac atg gac tac atc aag cac gcg ctg act ctc ttc acc gac    734
Arg Gly Asp Met Asp Tyr Ile Lys His Ala Leu Thr Leu Phe Thr Asp
            210                 215                 220 ttt gtt gcg gtt ctt gtt cga atc ctt gtc atc atg atg aag aat gca    782
Phe Val Ala Val Leu Val Arg Ile Leu Val Ile Met Met Lys Asn Ala
        225                 230                 235 cag gag aaa tcc caa gac gag aag aag agg aag aag cgg ta gctgctgaat  833
Gln Glu Lys Ser Gln Asp Glu Lys Lys Arg Lys Lys Arg
    240                 245                 250 gaattggatg acatatgttg ttgtggtcac tacttcatag taccgtgtac tcctatccta   893
ttgtactaat aataataata gtaagacgaa agatgactgc tgggaatgaa tatttggttc   953
tgct                                                                957
```

<210> SEQ ID NO 2
<211> LENGTH: 250
<212> TYPE: PRT
<213> ORGANISM: Zea mays

<400> SEQUENCE: 2

```
Met Glu Ser Leu Phe Gly Gln Ser Gln Arg Arg Arg Arg Ala Gly Gly
  1               5                  10                  15

Ser Gly Phe Glu Ser Leu Lys Arg Leu Gly His Ile Ser Pro Ala Val
             20                  25                  30

Gln Ser His Leu Lys His Val Tyr Leu Thr Leu Cys Ser Ala Leu Ala
         35                  40                  45

Phe Ser Ala Leu Gly Ala Tyr Leu His Ile Leu Leu Asn Val Gly Gly
     50                  55                  60

Ala Leu Thr Thr Val Gly Cys Val Ala Ser Ile Ala Phe Leu Ile Ser
 65                  70                  75                  80

Leu Pro Ala Ser Arg Asp Gln Glu Arg Asn Arg Leu Ala Leu Leu Met
             85                  90                  95

Ser Ala Ala Leu Leu Gln Gly Ala Ser Val Gly Pro Leu Val Asp Leu
            100                 105                 110

Val Ile Asp Leu Asp Ser Arg Ile Leu Val Thr Ala Phe Val Gly Thr
        115                 120                 125

Ala Val Ala Phe Ala Cys Phe Ser Gly Ala Ala Ile Ile Ala Lys Arg
    130                 135                 140
```

```
Arg Glu Tyr Leu Tyr Leu Gly Gly Leu Leu Ser Ser Gly Leu Ser Ile
145                 150                 155                 160

Leu Leu Trp Leu Gln Phe Ala Thr Ser Ile Phe Gly His Thr Ser Ala
                165                 170                 175

Thr Phe Met Phe Glu Leu Tyr Phe Gly Leu Leu Val Phe Leu Gly Tyr
            180                 185                 190

Met Val Phe Asp Thr Gln Glu Ile Ile Glu Arg Ala His Arg Gly Asp
        195                 200                 205

Met Asp Tyr Ile Lys His Ala Leu Thr Leu Phe Thr Asp Phe Val Ala
    210                 215                 220

Val Leu Val Arg Ile Leu Val Ile Met Met Lys Asn Ala Gln Glu Lys
225                 230                 235                 240

Ser Gln Asp Glu Lys Lys Arg Lys Lys Arg
                245                 250

<210> SEQ ID NO 3
<211> LENGTH: 1026
<212> TYPE: DNA
<213> ORGANISM: Zea mays
<220> FEATURE:
<221> NAME/KEY: CDS
<222> LOCATION: (72)...(830)

<400> SEQUENCE: 3
cctcgatcgg cctccctccc ccaagatcct ccactcgatc ccaaacaaac caacaaatcc      60
atccatcgca c atg gac gcg ttc ttc tcg gcc tcc tcc gcg tcg gcg ccc     110
            Met Asp Ala Phe Phe Ser Ala Ser Ser Ala Ser Ala Pro
              1               5                  10 tac ggc tac ggc gcc ggc gga tgg agc tac gac tcg ctc aag aac ttc     158
Tyr Gly Tyr Gly Ala Gly Gly Trp Ser Tyr Asp Ser Leu Lys Asn Phe
 15                  20                  25 cgc cag atc acc ccc gcc gtc cag acc cac ctc aag ctc gtc tac ctc     206
Arg Gln Ile Thr Pro Ala Val Gln Thr His Leu Lys Leu Val Tyr Leu
 30                  35                  40                  45 acc ctg tgc gcg gcg ctg gcc tcg tcg gcg gtg ggc gct tac ctg cac     254
Thr Leu Cys Ala Ala Leu Ala Ser Ser Ala Val Gly Ala Tyr Leu His
                 50                  55                  60 gtg gtc tgg aac atc ggc ggt acg ctg aca atg ctc ggt tgc gtc ggc     302
Val Val Trp Asn Ile Gly Gly Thr Leu Thr Met Leu Gly Cys Val Gly
             65                  70                  75 agc atc gcc tgg ctc ttc tcg gtg ccc gtc tac gag gag agg aag agg     350
Ser Ile Ala Trp Leu Phe Ser Val Pro Val Tyr Glu Glu Arg Lys Arg
         80                  85                  90 tat ggg ctg ctg atg gcg gct gcc ctc ctg gaa ggc gct tcg gtc gga     398
Tyr Gly Leu Leu Met Ala Ala Ala Leu Leu Glu Gly Ala Ser Val Gly
     95                 100                 105 ccc ctc gtc aag ctc gcc gtg gaa ttt gac cca agc atc ctg gtg acg     446
Pro Leu Val Lys Leu Ala Val Glu Phe Asp Pro Ser Ile Leu Val Thr
110                 115                 120                 125 gcg ttc gtg ggg act gcc atc gcg ttc gcg tgc ttc acc ggc gcg gcc     494
Ala Phe Val Gly Thr Ala Ile Ala Phe Ala Cys Phe Thr Gly Ala Ala
                130                 135                 140 atg gtg gcc agg cgc agg gag tac ctc tac ctg ggt ggg ctg ctc tcg     542
Met Val Ala Arg Arg Arg Glu Tyr Leu Tyr Leu Gly Gly Leu Leu Ser
            145                 150                 155 tcg ggg ctc tcc atc ctg ctc tgg ctg cag cta gcc ggc tcc atc ttc     590
Ser Gly Leu Ser Ile Leu Leu Trp Leu Gln Leu Ala Gly Ser Ile Phe
        160                 165                 170 ggc cac tcc gca acc agc ttc atg ttc gag gtc tac ttc ggg ctg ctc     638
```

```
              Gly His Ser Ala Thr Ser Phe Met Phe Glu Val Tyr Phe Gly Leu Leu
                  175                 180                 185 atc ttc ctg ggc tac gtg gtg tac gac acg cag gag atc atc gag agg              686
Ile Phe Leu Gly Tyr Val Val Tyr Asp Thr Gln Glu Ile Ile Glu Arg
190                 195                 200                 205 gcg cac cgc ggc gac atg gac cac gtc aag cac gcc ctc acc ctc ttc              734
Ala His Arg Gly Asp Met Asp His Val Lys His Ala Leu Thr Leu Phe
                    210                 215                 220 aca gac ttc gtg gcc gtc ctc gtc cgc gtc ctc gtc atc atg ctc aaa              782
Thr Asp Phe Val Ala Val Leu Val Arg Val Leu Val Ile Met Leu Lys
                225                 230                 235 gaa cgg ggc cga caa gtc gga gga caa gaa gag gaa gaa gag tcg tga              830
Glu Arg Gly Arg Gln Val Gly Gly Gln Glu Glu Glu Glu Glu Ser *
            240                 245                 250 gcgcgtccag aagggaagct cttccacttc cacatatgca taggagtaac tgctggggtt            890
ccttcctggg gtggaagtgt ggaactgagc tgagtgttca aaaagtgttc ctttgttcgg            950
caactttgtt ctccttcctc tcttgaagag tctgtaaata actatgtcaa tctgggttaa           1010
gcttggtttg ggtgcc                                                           1026

<210> SEQ ID NO 4
<211> LENGTH: 252
<212> TYPE: PRT
<213> ORGANISM: Zea mays

<400> SEQUENCE: 4

Met Asp Ala Phe Phe Ser Ala Ser Ser Ala Ser Ala Pro Tyr Gly Tyr
 1               5                  10                  15

Gly Ala Gly Gly Trp Ser Tyr Asp Ser Leu Lys Asn Phe Arg Gln Ile
                20                  25                  30

Thr Pro Ala Val Gln Thr His Leu Lys Leu Val Tyr Leu Thr Leu Cys
            35                  40                  45

Ala Ala Leu Ala Ser Ser Ala Val Gly Ala Tyr Leu His Val Val Trp
        50                  55                  60

Asn Ile Gly Gly Thr Leu Thr Met Leu Gly Cys Val Gly Ser Ile Ala
65                  70                  75                  80

Trp Leu Phe Ser Val Pro Val Tyr Glu Glu Arg Lys Tyr Gly Leu
                85                  90                  95

Leu Met Ala Ala Ala Leu Leu Glu Gly Ala Ser Val Gly Pro Leu Val
                100                 105                 110

Lys Leu Ala Val Glu Phe Asp Pro Ser Ile Leu Val Thr Ala Phe Val
            115                 120                 125

Gly Thr Ala Ile Ala Phe Ala Cys Phe Thr Gly Ala Ala Met Val Ala
        130                 135                 140

Arg Arg Arg Glu Tyr Leu Tyr Leu Gly Gly Leu Leu Ser Ser Gly Leu
145                 150                 155                 160

Ser Ile Leu Leu Trp Leu Gln Leu Ala Gly Ser Ile Phe Gly His Ser
                165                 170                 175

Ala Thr Ser Phe Met Phe Glu Val Tyr Phe Gly Leu Leu Ile Phe Leu
            180                 185                 190

Gly Tyr Val Val Tyr Asp Thr Gln Glu Ile Ile Glu Arg Ala His Arg
        195                 200                 205

Gly Asp Met Asp His Val Lys His Ala Leu Thr Leu Phe Thr Asp Phe
    210                 215                 220

Val Ala Val Leu Val Arg Val Leu Val Ile Met Leu Lys Glu Arg Gly
225                 230                 235                 240
```

```
Arg Gln Val Gly Gly Gln Glu Glu Glu Glu Ser
                245                 250
```

<210> SEQ ID NO 5
<211> LENGTH: 1139
<212> TYPE: DNA
<213> ORGANISM: Zea mays
<220> FEATURE:
<221> NAME/KEY: CDS
<222> LOCATION: (136)...(993)

<400> SEQUENCE: 5

```
cccacgcgtc cgcccacgcg tccgaagcca tagccacgac acgactccat tcccagattc     60
aaatccatcc atcccatcca tcatccatc catccgcagc gggcaggcac acacacaggc    120
tttgcgttgg caggg atg gac gcg ttc tac tcg acc acc gcc tcc tcc tcc    171
             Met Asp Ala Phe Tyr Ser Thr Thr Ala Ser Ser Ser
               1               5                  10 acg tcg tcg gcg ccg tac ggc ggc ggc gaa ggc tgg ggc tac gac         219
Thr Ser Ser Ala Pro Tyr Gly Gly Gly Glu Gly Trp Gly Tyr Asp
         15                  20                  25 tcg atg aag aac ttc cgc cag atc agc ccc gcc gtc cag acc cac ctc    267
Ser Met Lys Asn Phe Arg Gln Ile Ser Pro Ala Val Gln Thr His Leu
 30                  35                  40 aag ctc gtt tac ctc acc cta tgc gtg gcg ctg gcc tcg tcg gcg gtg    315
Lys Leu Val Tyr Leu Thr Leu Cys Val Ala Leu Ala Ser Ser Ala Val
 45                  50                  55                  60 ggc gcg tac ctg cac gtc gtc tgg aac atc ggc ggg atg ctg acc atg    363
Gly Ala Tyr Leu His Val Val Trp Asn Ile Gly Gly Met Leu Thr Met
             65                  70                  75 ctc ggc tgc gtc ggc agc atc gcc tgg ctc ttc tcg gtg ccc gtc tac    411
Leu Gly Cys Val Gly Ser Ile Ala Trp Leu Phe Ser Val Pro Val Tyr
         80                  85                  90 gag gag agg aag agg tac tgg ctg ctg atg gcg gct gcc ctc ctg gaa    459
Glu Glu Arg Lys Arg Tyr Trp Leu Leu Met Ala Ala Ala Leu Leu Glu
         95                 100                 105 ggg gcg tcg gtt gga ccc ctc atc aag ctc gcc gtg gaa ttt gac cca    507
Gly Ala Ser Val Gly Pro Leu Ile Lys Leu Ala Val Glu Phe Asp Pro
110                 115                 120 agc atc ctg gtg aca gcg ttc gtg ggg act gcc att gcg ttc gcg tgc    555
Ser Ile Leu Val Thr Ala Phe Val Gly Thr Ala Ile Ala Phe Ala Cys
125                 130                 135                 140 ttc tct tgc gcg gcc atg gtg gcc aag cgc agg gag tac ctc tac ctg    603
Phe Ser Cys Ala Ala Met Val Ala Lys Arg Arg Glu Tyr Leu Tyr Leu
                145                 150                 155 ggc ggg ctg ctc tct tct ggc ctc tcc atc ctg ctc tgg ctg cag ttc    651
Gly Gly Leu Leu Ser Ser Gly Leu Ser Ile Leu Leu Trp Leu Gln Phe
            160                 165                 170 gcc gcc tcc atc ttc ggc cac caa tcc act agc agc ttc atg ttt gag    699
Ala Ala Ser Ile Phe Gly His Gln Ser Thr Ser Ser Phe Met Phe Glu
        175                 180                 185 gtc tac ttt ggg ctg ctc atc ttc ctg ggc tac atg gtg tac gac acg    747
Val Tyr Phe Gly Leu Leu Ile Phe Leu Gly Tyr Met Val Tyr Asp Thr
        190                 195                 200 cag gag gtc atc gag agg gcg cac cac ggc gac atg gac tac atc aag    795
Gln Glu Val Ile Glu Arg Ala His His Gly Asp Met Asp Tyr Ile Lys
205                 210                 215                 220 cac gcc ctc acc ctc ttc acc gac ttc gtg gct gtc ctt gtc cgc atc    843
His Ala Leu Thr Leu Phe Thr Asp Phe Val Ala Val Leu Val Arg Ile
                225                 230                 235
```

```
ctt gtc atc atg ctc aag aac gcg gct gac aag tcg gag gac aag agg        891
Leu Val Ile Met Leu Lys Asn Ala Ala Asp Lys Ser Glu Asp Lys Arg
            240                 245                 250 agg aag agg agg agt gtg gtg aaa atc tgt gtg cga aca cag cac tca        939
Arg Lys Arg Arg Ser Val Val Lys Ile Cys Val Arg Thr Gln His Ser
        255                 260                 265 agg gaa ggg aag gaa ggc act ggt gcg tct gaa atg aag ctc cca cat        987
Arg Glu Gly Lys Glu Gly Thr Gly Ala Ser Glu Met Lys Leu Pro His
270                 275                 280 aac tag gtgtatacat ataggagc gaggagttac tttggggtgg aactgacctg          1043
Asn *
285 tgcaagtgtc gttcctttgt tttctcttga tctgtcatca gtgagcctgt tgatagtttt    1103 gtcctgtcct gtgaatgaat atgacaaatc tccccc                               1139

<210> SEQ ID NO 6
<211> LENGTH: 285
<212> TYPE: PRT
<213> ORGANISM: Zea mays

<400> SEQUENCE: 6

Met Asp Ala Phe Tyr Ser Thr Thr Ala Ser Ser Ser Thr Ser Ser Ala
1               5                   10                  15

Pro Tyr Gly Gly Gly Glu Gly Trp Gly Tyr Asp Ser Met Lys Asn
            20                  25                  30

Phe Arg Gln Ile Ser Pro Ala Val Gln Thr His Leu Lys Leu Val Tyr
        35                  40                  45

Leu Thr Leu Cys Val Ala Leu Ala Ser Ser Ala Val Gly Ala Tyr Leu
    50                  55                  60

His Val Val Trp Asn Ile Gly Gly Met Leu Thr Met Leu Gly Cys Val
65                  70                  75                  80

Gly Ser Ile Ala Trp Leu Phe Ser Val Pro Val Tyr Glu Glu Arg Lys
                85                  90                  95

Arg Tyr Trp Leu Leu Met Ala Ala Ala Leu Leu Glu Gly Ala Ser Val
            100                 105                 110

Gly Pro Leu Ile Lys Leu Ala Val Glu Phe Asp Pro Ser Ile Leu Val
        115                 120                 125

Thr Ala Phe Val Gly Thr Ala Ile Ala Phe Ala Cys Phe Ser Cys Ala
    130                 135                 140

Ala Met Val Ala Lys Arg Arg Glu Tyr Leu Tyr Leu Gly Gly Leu Leu
145                 150                 155                 160

Ser Ser Gly Leu Ser Ile Leu Leu Trp Leu Gln Phe Ala Ala Ser Ile
                165                 170                 175

Phe Gly His Gln Ser Thr Ser Ser Phe Met Phe Glu Val Tyr Phe Gly
            180                 185                 190

Leu Leu Ile Phe Leu Gly Tyr Met Val Tyr Asp Thr Gln Glu Val Ile
        195                 200                 205

Glu Arg Ala His His Gly Asp Met Asp Tyr Ile Lys His Ala Leu Thr
    210                 215                 220

Leu Phe Thr Asp Phe Val Ala Val Leu Val Arg Ile Leu Val Ile Met
225                 230                 235                 240

Leu Lys Asn Ala Ala Asp Lys Ser Glu Asp Lys Arg Arg Lys Arg Arg
                245                 250                 255

Ser Val Val Lys Ile Cys Val Arg Thr Gln His Ser Arg Glu Gly Lys
            260                 265                 270
```

```
          Glu Gly Thr Gly Ala Ser Glu Met Lys Leu Pro His Asn
                  275                 280                 285

<210> SEQ ID NO 7
<211> LENGTH: 740
<212> TYPE: DNA
<213> ORGANISM: zea mays
<220> FEATURE:
<221> NAME/KEY: CDS
<222> LOCATION: (64)...(489)

<400> SEQUENCE: 7
cgctaccagg ctggcaatgc gtcaccagcc cgccataagt tgtagtagta gacaaatgct      60 tag atg acg aat ggc tgt ttt ttt tcc ctc agc atc ctg gtg acg gcg     108
    Met Thr Asn Gly Cys Phe Phe Ser Leu Ser Ile Leu Val Thr Ala
    1               5                   10                  15 ttc gtg ggg act gcc atc gcg ttc gcg tgc ttc acc ggc gcg gcc atg     156
Phe Val Gly Thr Ala Ile Ala Phe Ala Cys Phe Thr Gly Ala Ala Met
                20                  25                  30 gtg gcc agg cgc agg gag tac ctc tac ctg ggt ggg ctg ctc tcg tcg     204
Val Ala Arg Arg Arg Glu Tyr Leu Tyr Leu Gly Gly Leu Leu Ser Ser
            35                  40                  45 ggg ctc tcc atc ctg ctc tgg ctg cag cta gcc ggc tcc atc ttc ggc     252
Gly Leu Ser Ile Leu Leu Trp Leu Gln Leu Ala Gly Ser Ile Phe Gly
        50                  55                  60 cac tcc gca acc agc ttc atg ttc gag gtc tac ttc ggg ctg ctc atc     300
His Ser Ala Thr Ser Phe Met Phe Glu Val Tyr Phe Gly Leu Leu Ile
    65                  70                  75 ttc ctg ggc tac gtg gtg tac gac acg cag gag atc atc gag agg gcg     348
Phe Leu Gly Tyr Val Val Tyr Asp Thr Gln Glu Ile Ile Glu Arg Ala
80                  85                  90                  95 cac cgc ggc gac atg gac cac gtc aag cac gcc ctc acc ctc ttc aca     396
His Arg Gly Asp Met Asp His Val Lys His Ala Leu Thr Leu Phe Thr
                100                 105                 110 gac ttc gtg gcc gtc ctc gtc cgc gtc ctc gtc atc atg ctc aag aac     444
Asp Phe Val Ala Val Leu Val Arg Val Leu Val Ile Met Leu Lys Asn
            115                 120                 125 ggg gcc gac aag tcg gag gac aag aag agg aag aag agg tcg tga         489
Gly Ala Asp Lys Ser Glu Asp Lys Lys Arg Lys Lys Arg Ser *
        130                 135                 140 gcgcgtcgag aagggaagct cttccacttc cacatatgca taggagtaac tgctggggtt     549
ccttcctggg gtggaagtgt ggaactgagc tgagtgttca gaagtgttcc tttgttcggc     609
acctttgttc tcttcctctc ttgatgagtc tgtaaatagc tatgtcaatc tggttaagct     669
tggtttggtt gcctgtgcct gtgttcgctg gcctttggat agaatgcaaa ttaaagatgt     729
tgctattgca c                                                          740

<210> SEQ ID NO 8
<211> LENGTH: 141
<212> TYPE: PRT
<213> ORGANISM: zea mays

<400> SEQUENCE: 8

Met Thr Asn Gly Cys Phe Phe Ser Leu Ser Ile Leu Val Thr Ala Phe
1               5                   10                  15

Val Gly Thr Ala Ile Ala Phe Ala Cys Phe Thr Gly Ala Ala Met Val
            20                  25                  30

Ala Arg Arg Arg Glu Tyr Leu Tyr Leu Gly Gly Leu Leu Ser Ser Gly
        35                  40                  45
```

```
Leu Ser Ile Leu Leu Trp Leu Gln Leu Ala Gly Ser Ile Phe Gly His
 50                  55                  60

Ser Ala Thr Ser Phe Met Phe Glu Val Tyr Phe Gly Leu Leu Ile Phe
 65                      70                  75                  80

Leu Gly Tyr Val Val Tyr Asp Thr Gln Glu Ile Ile Glu Arg Ala His
                     85                  90                  95

Arg Gly Asp Met Asp His Val Lys His Ala Leu Thr Leu Phe Thr Asp
                100                 105                 110

Phe Val Ala Val Leu Val Arg Val Leu Val Ile Met Leu Lys Asn Gly
            115                 120                 125

Ala Asp Lys Ser Glu Asp Lys Lys Arg Lys Lys Arg Ser
130                 135                 140

<210> SEQ ID NO 9
<211> LENGTH: 1164
<212> TYPE: DNA
<213> ORGANISM: zea mays
<220> FEATURE:
<221> NAME/KEY: CDS
<222> LOCATION: (149)...(880)

<400> SEQUENCE: 9
ggtagtccga gccagcgaac caactattcg tttgcttttc gtcttcgtcc tctctttgcc      60
cagttgtcgg tcgcccgcgc cgtcgtctcc gctccgccgg ccttcctgcg aaaccctagc    120
gaggcgagcg agagagaaac tagcggcc atg ttc ggc tac agg aag gct gac       172
                                Met Phe Gly Tyr Arg Lys Ala Asp
                                  1               5 ccg gac ctc gag gcc ggc ggg tcc tcg ctg ctg tac ccg gga atg acg      220
Pro Asp Leu Glu Ala Gly Gly Ser Ser Leu Leu Tyr Pro Gly Met Thr
 10                  15                  20 gag agc ccc gag ctg cgg tgg gcg ttc gtc cgc aag atc tac gtc atc      268
Glu Ser Pro Glu Leu Arg Trp Ala Phe Val Arg Lys Ile Tyr Val Ile
25                  30                  35                  40 cta gcc gtc cag ctc gcc atg acg gcc gcg gtc tcc gcc ttc gtc gtc      316
Leu Ala Val Gln Leu Ala Met Thr Ala Ala Val Ser Ala Phe Val Val
                 45                  50                  55 aag gtg ccc gcc gtc tcc aac ttc ttc gtc ttc tcc aac gcc ggg gtc      364
Lys Val Pro Ala Val Ser Asn Phe Phe Val Phe Ser Asn Ala Gly Val
             60                  65                  70 gca ctc tac atc ttc ctc atc atc ctg cct ttc ctc gtg ctg tgc cct      412
Ala Leu Tyr Ile Phe Leu Ile Ile Leu Pro Phe Leu Val Leu Cys Pro
         75                  80                  85 ctg cgc tac tac cac cag aag cat ccg gtc aat ctg ctg ctg ctc ggc      460
Leu Arg Tyr Tyr His Gln Lys His Pro Val Asn Leu Leu Leu Leu Gly
     90                  95                 100 ctc ttc acc gtc gcc atc agc ttt gcc gtc ggc atg aca tgc gct ttc      508
Leu Phe Thr Val Ala Ile Ser Phe Ala Val Gly Met Thr Cys Ala Phe
105                 110                 115                 120 act agc gga aaa atc att ttg gag gct gcc att ctt aca gca gtg gtg      556
Thr Ser Gly Lys Ile Ile Leu Glu Ala Ala Ile Leu Thr Ala Val Val
                125                 130                 135 gtg atc agc tta act gcg tac act ttc tgg gct gca aag agg ggt cat      604
Val Ile Ser Leu Thr Ala Tyr Thr Phe Trp Ala Ala Lys Arg Gly His
            140                 145                 150 gat ttc aac ttc ctc ggt ccc ttc cta ttt gct gct atc atg gtg ctc      652
Asp Phe Asn Phe Leu Gly Pro Phe Leu Phe Ala Ala Ile Met Val Leu
        155                 160                 165 atg gtg ttt tca cta atc cag atc ttt ttc ccg ctg ggt aag ata tct      700
Met Val Phe Ser Leu Ile Gln Ile Phe Phe Pro Leu Gly Lys Ile Ser
```

```
                170                 175                 180
gtg atg ata tac ggt ggg ttg gca tcg ctt atc ttc tgt gga tac atc      748
Val Met Ile Tyr Gly Gly Leu Ala Ser Leu Ile Phe Cys Gly Tyr Ile
185                 190                 195                 200 atc tat gac acg gac aat gtc atc aag cgc tac acc tac gat gaa tac      796
Ile Tyr Asp Thr Asp Asn Val Ile Lys Arg Tyr Thr Tyr Asp Glu Tyr
                205                 210                 215 ata tgg gct gct gtt tca ctc tac ctt gac gtc atc aac ctg ttc ctg      844
Ile Trp Ala Ala Val Ser Leu Tyr Leu Asp Val Ile Asn Leu Phe Leu
                220                 225                 230 tct ctg ctg cag ctg ctg agg gca gcc gat agc tga gctcgtcaag           890
Ser Leu Leu Gln Leu Leu Arg Ala Ala Asp Ser  *
                235                 240 ctttcacttc gatcttgttc tcacatacat ctgtgtatat cacaaactct gtaatggtca    950
tggatactcc aatttataac tatactctgt cggtgttacc ttggttcaaa tggtatgtct   1010
ggctttaacg gatacccatg agagttttaa gagcgcggtc aatagctcag ctgcttacaa   1070
acgagcttgg ataaaaatca taagctgtgc agtaacagta catctgtact tgtcttgatc   1130
aattatttgc ataattatt tatgattttg cacc                                1164

<210> SEQ ID NO 10
<211> LENGTH: 243
<212> TYPE: PRT
<213> ORGANISM: zea mays

<400> SEQUENCE: 10

Met Phe Gly Tyr Arg Lys Ala Asp Pro Asp Leu Glu Ala Gly Gly Ser
 1               5                  10                  15

Ser Leu Leu Tyr Pro Gly Met Thr Glu Ser Pro Glu Leu Arg Trp Ala
             20                  25                  30

Phe Val Arg Lys Ile Tyr Val Ile Leu Ala Val Gln Leu Ala Met Thr
         35                  40                  45

Ala Ala Val Ser Ala Phe Val Val Lys Val Pro Ala Val Ser Asn Phe
     50                  55                  60

Phe Val Phe Ser Asn Ala Gly Val Ala Leu Tyr Ile Phe Leu Ile Ile
 65                  70                  75                  80

Leu Pro Phe Leu Val Leu Cys Pro Leu Arg Tyr Tyr His Gln Lys His
                 85                  90                  95

Pro Val Asn Leu Leu Leu Gly Leu Phe Thr Val Ala Ile Ser Phe
             100                 105                 110

Ala Val Gly Met Thr Cys Ala Phe Thr Ser Gly Lys Ile Ile Leu Glu
         115                 120                 125

Ala Ala Ile Leu Thr Ala Val Val Ile Ser Leu Thr Ala Tyr Thr
     130                 135                 140

Phe Trp Ala Ala Lys Arg Gly His Asp Phe Asn Phe Leu Gly Pro Phe
145                 150                 155                 160

Leu Phe Ala Ala Ile Met Val Leu Met Val Phe Ser Leu Ile Gln Ile
                165                 170                 175

Phe Phe Pro Leu Gly Lys Ile Ser Val Met Ile Tyr Gly Gly Leu Ala
            180                 185                 190

Ser Leu Ile Phe Cys Gly Tyr Ile Ile Tyr Asp Thr Asp Asn Val Ile
        195                 200                 205

Lys Arg Tyr Thr Tyr Asp Glu Tyr Ile Trp Ala Ala Val Ser Leu Tyr
    210                 215                 220

Leu Asp Val Ile Asn Leu Phe Leu Ser Leu Leu Gln Leu Leu Arg Ala
```

-continued

```
             225                 230                 235                 240
Ala Asp Ser

<210> SEQ ID NO 11
<211> LENGTH: 1174
<212> TYPE: DNA
<213> ORGANISM: zea mays
<220> FEATURE:
<221> NAME/KEY: CDS
<222> LOCATION: (135)...(929)

<400> SEQUENCE: 11
caaaatcccc aaccgcctct caacaaagtc tccccacgga ggtacacagc tacgcgcaaa      60
ccgcgtctcg cgcgaagaat ccgcatttcc ccttccccgc accgcaccgc acccaaccc     120 cgtcggagag agag atg gca tcg gtg gcg gag atg cag ccc ctc gcg ccg      170
              Met Ala Ser Val Ala Glu Met Gln Pro Leu Ala Pro
                1               5                  10 gcg ggg tac cgc cgc gcg ccg gag atg aag gag aag gtg gag gcg tcg      218
Ala Gly Tyr Arg Arg Ala Pro Glu Met Lys Glu Lys Val Glu Ala Ser
         15                  20                  25 gtg gtg gac ctg gag gcc ggg acc ggg gag acg ctg tac ccg ggg atc      266
Val Val Asp Leu Glu Ala Gly Thr Gly Glu Thr Leu Tyr Pro Gly Ile
 30                  35                  40 tcg cgc ggg gag agc gcc ctc cga tgg ggc ttc gtc cgc aag gtc tac      314
Ser Arg Gly Glu Ser Ala Leu Arg Trp Gly Phe Val Arg Lys Val Tyr
 45                  50                  55                  60 ggc atc ctc gct gcg cag ctg ctc ctc acc acc gcc gtc tcc gcc ctc      362
Gly Ile Leu Ala Ala Gln Leu Leu Leu Thr Thr Ala Val Ser Ala Leu
                 65                  70                  75 acc gtt ctc cac ccc acc ctc aac gcc acg ctc tcc gac tcc ccg ggc      410
Thr Val Leu His Pro Thr Leu Asn Ala Thr Leu Ser Asp Ser Pro Gly
             80                  85                  90 ctc gcg ctc gtg ctc gcc gtc ctg ccc ttc atc ctg atg atc cca ttg      458
Leu Ala Leu Val Leu Ala Val Leu Pro Phe Ile Leu Met Ile Pro Leu
         95                 100                 105 tat cat tat cag cac aag cac cca cac aat ttc gtt ttc ctg ggt ctg      506
Tyr His Tyr Gln His Lys His Pro His Asn Phe Val Phe Leu Gly Leu
 110                 115                 120 ttc acg ttg tgc ttg agc ttc agc atc ggt gtg gct tgt gct aac acc      554
Phe Thr Leu Cys Leu Ser Phe Ser Ile Gly Val Ala Cys Ala Asn Thr
125                 130                 135                 140 caa ggg aaa atc gtt ctg gag gct tta gtg ctg acg gct ggc gtg gtg      602
Gln Gly Lys Ile Val Leu Glu Ala Leu Val Leu Thr Ala Gly Val Val
                145                 150                 155 gtt tct ctg act gcg tat gct ttc tgg gcg tca aag aag ggc aag gaa      650
Val Ser Leu Thr Ala Tyr Ala Phe Trp Ala Ser Lys Lys Gly Lys Glu
            160                 165                 170 ttc ggg tac ctg ggg cct atc ctg tct tcc gcg ctt act atc ctc gtc      698
Phe Gly Tyr Leu Gly Pro Ile Leu Ser Ser Ala Leu Thr Ile Leu Val
        175                 180                 185 cta act agc ttt ctt cag gtt ttc ttc cca ctg gga ccc gtg tcg gtg      746
Leu Thr Ser Phe Leu Gln Val Phe Phe Pro Leu Gly Pro Val Ser Val
    190                 195                 200 ggc ttg ttc ggt ggg cta ggg gct ctg gtc ttc tca ggc ttc atc ctg      794
Gly Leu Phe Gly Gly Leu Gly Ala Leu Val Phe Ser Gly Phe Ile Leu
205                 210                 215                 220 tac gac acc gag aac ctg atc aag cgc cac acc tac gac gag tac atc      842
Tyr Asp Thr Glu Asn Leu Ile Lys Arg His Thr Tyr Asp Glu Tyr Ile
                225                 230                 235
```

```
tgg gcg tcg gtt ggg ctg tac ctc gac atc ctg aac ctg ttc ctc tcc      890
Trp Ala Ser Val Gly Leu Tyr Leu Asp Ile Leu Asn Leu Phe Leu Ser
        240                 245                 250 atc ctg aac atg ctc agg agc atg caa tcc gac aac tag cctcttgatc       939
Ile Leu Asn Met Leu Arg Ser Met Gln Ser Asp Asn  *
    255                 260 gaacacggta taccccatg gtaaatgcgg tcctgtgctc tggttgttag aggacgggat     999
cgacgtgcga catatgtatt gtgtgagccc actcgtgtca acactgcaaa caattgtggt    1059
catgtcacct tgtatgttct tggtcacttt tcaaacaatt gtaagtacct catatcgttt    1119
tgcgctcgtg ctattcgcgc taaaaatcac aatgatccag taacaggttg tcatc         1174
```

<210> SEQ ID NO 12
<211> LENGTH: 264
<212> TYPE: PRT
<213> ORGANISM: zea mays

<400> SEQUENCE: 12

```
Met Ala Ser Val Ala Glu Met Gln Pro Leu Ala Pro Ala Gly Tyr Arg
 1               5                  10                  15

Arg Ala Pro Glu Met Lys Glu Lys Val Glu Ala Ser Val Val Asp Leu
            20                  25                  30

Glu Ala Gly Thr Gly Glu Thr Leu Tyr Pro Gly Ile Ser Arg Gly Glu
        35                  40                  45

Ser Ala Leu Arg Trp Gly Phe Val Arg Lys Val Tyr Gly Ile Leu Ala
    50                  55                  60

Ala Gln Leu Leu Leu Thr Thr Ala Val Ser Ala Leu Thr Val Leu His
65                  70                  75                  80

Pro Thr Leu Asn Ala Thr Leu Ser Asp Ser Pro Gly Leu Ala Leu Val
                85                  90                  95

Leu Ala Val Leu Pro Phe Ile Leu Met Ile Pro Leu Tyr His Tyr Gln
            100                 105                 110

His Lys His Pro His Asn Phe Val Phe Leu Gly Leu Phe Thr Leu Cys
        115                 120                 125

Leu Ser Phe Ser Ile Gly Val Ala Cys Ala Asn Thr Gln Gly Lys Ile
    130                 135                 140

Val Leu Glu Ala Leu Val Leu Thr Ala Gly Val Val Ser Leu Thr
145                 150                 155                 160

Ala Tyr Ala Phe Trp Ala Ser Lys Lys Gly Lys Glu Phe Gly Tyr Leu
                165                 170                 175

Gly Pro Ile Leu Ser Ser Ala Leu Thr Ile Leu Val Leu Thr Ser Phe
            180                 185                 190

Leu Gln Val Phe Phe Pro Leu Gly Pro Val Ser Val Gly Leu Phe Gly
        195                 200                 205

Gly Leu Gly Ala Leu Val Phe Ser Gly Phe Ile Leu Tyr Asp Thr Glu
    210                 215                 220

Asn Leu Ile Lys Arg His Thr Tyr Asp Glu Tyr Ile Trp Ala Ser Val
225                 230                 235                 240

Gly Leu Tyr Leu Asp Ile Leu Asn Leu Phe Leu Ser Ile Leu Asn Met
                245                 250                 255

Leu Arg Ser Met Gln Ser Asp Asn
            260
```

<210> SEQ ID NO 13
<211> LENGTH: 1093
<212> TYPE: DNA

<213> ORGANISM: zea mays
<220> FEATURE:
<221> NAME/KEY: CDS
<222> LOCATION: (189)...(938)

<400> SEQUENCE: 13

```
aggaggcgcc gcgctcctct tcttctacgc cgttcactct ctctagtctc tcccttccct    60
tctccacgcc tccgccccca ctcgtgagac cctacctagc cctagcgcca gcaccacccg   120
cccaacctcc cggagagaga gaggaggagg ccttcgccgc cgccgttacc gtcggccgag   180 gcgccaga atg ttc ggg tac cag aag ggc ctc gac gtc gag gcg ggg aca   230
         Met Phe Gly Tyr Gln Lys Gly Leu Asp Val Glu Ala Gly Thr
           1               5                  10 tcg ggc gcc gcc gcc acg ggc ggc gcg cgc cag ctc tac ccg ggg atg   278
Ser Gly Ala Ala Ala Thr Gly Gly Ala Arg Gln Leu Tyr Pro Gly Met
 15                  20                  25                  30 cag gag agc ccc gag ctg cgc tgg gcg ctc atc cgc aag atc tac gtc   326
Gln Glu Ser Pro Glu Leu Arg Trp Ala Leu Ile Arg Lys Ile Tyr Val
                 35                  40                  45 att ctc tcc ctc cag ctg ctc ctc acc gcc gtc gtc gcc gca gtc gtc   374
Ile Leu Ser Leu Gln Leu Leu Leu Thr Ala Val Val Ala Ala Val Val
             50                  55                  60 gtc aag gtc cgc gcc atc ccg cac ttc ttc acc acc acc agc gcc ggc   422
Val Lys Val Arg Ala Ile Pro His Phe Phe Thr Thr Thr Ser Ala Gly
 65                  70                  75 ctc ggc ctc tac atc ttc ctc atc atc ctc ccc ttt atc gtg ctg tgc   470
Leu Gly Leu Tyr Ile Phe Leu Ile Ile Leu Pro Phe Ile Val Leu Cys
             80                  85                  90 ccg ctg tac ttc tac cac gag aag cac cca gtc aac ctg atc ctg ctc   518
Pro Leu Tyr Phe Tyr His Glu Lys His Pro Val Asn Leu Ile Leu Leu
 95                 100                 105                 110 ggc ctc ttc acc gtt gcc atc agc ttt gct gtg ggc atg aca tgt gcc   566
Gly Leu Phe Thr Val Ala Ile Ser Phe Ala Val Gly Met Thr Cys Ala
                115                 120                 125 ttc acc agt ggc aag gtc att ctg gag tct gca att ctg aca aca gtg   614
Phe Thr Ser Gly Lys Val Ile Leu Glu Ser Ala Ile Leu Thr Thr Val
            130                 135                 140 gtc gtg ctc agc ctt acc gca tac act ttc tgg gcc gtg aat agg ggc   662
Val Val Leu Ser Leu Thr Ala Tyr Thr Phe Trp Ala Val Asn Arg Gly
145                 150                 155 aaa gac ttc agc ttc ctg ggt cct ttc ctg ttc gcc gcc atc ata gtg   710
Lys Asp Phe Ser Phe Leu Gly Pro Phe Leu Phe Ala Ala Ile Ile Val
    160                 165                 170 ctg ctt gtg ttc gca ctc atc cag atc ctg ttc cca ctg ggc aag ctc   758
Leu Leu Val Phe Ala Leu Ile Gln Ile Leu Phe Pro Leu Gly Lys Leu
175                 180                 185                 190 tcc cag atg atc tac ggc ggg ctg gcg tcg ctc atc ttc agc ggg tac   806
Ser Gln Met Ile Tyr Gly Gly Leu Ala Ser Leu Ile Phe Ser Gly Tyr
                195                 200                 205 atc gtc tac gac aca aac aac atc atc aag cgc tac acg tac gac cag   854
Ile Val Tyr Asp Thr Asn Asn Ile Ile Lys Arg Tyr Thr Tyr Asp Gln
            210                 215                 220 tac gtc tgg gcc gca gtc tca ctg tac ctg gac gtt atc aac ctc ttc   902
Tyr Val Trp Ala Ala Val Ser Leu Tyr Leu Asp Val Ile Asn Leu Phe
        225                 230                 235 ctg tcc ctg atg acc ctc ttc agg gca gcc gac tag gcgctctgct          948
Leu Ser Leu Met Thr Leu Phe Arg Ala Ala Asp *
    240                 245 ctcatcctgt ctatctacga gtcggtgcct gaatgctccc gtggttaagc tccggtaccc  1008
```

-continued

```
agaattccag ttccaagaat agagttgtat atagctaccc gcgttgcctt tctactagta    1068
tggtcttatt cggcttgact cggtt                                          1093
```

<210> SEQ ID NO 14
<211> LENGTH: 249
<212> TYPE: PRT
<213> ORGANISM: zea mays

<400> SEQUENCE: 14

```
Met Phe Gly Tyr Gln Lys Gly Leu Asp Val Glu Ala Gly Thr Ser Gly
  1               5                  10                  15

Ala Ala Ala Thr Gly Gly Ala Arg Gln Leu Tyr Pro Gly Met Gln Glu
             20                  25                  30

Ser Pro Glu Leu Arg Trp Ala Leu Ile Arg Lys Ile Tyr Val Ile Leu
         35                  40                  45

Ser Leu Gln Leu Leu Thr Ala Val Val Ala Val Val Val Val Val Lys
     50                  55                  60

Val Arg Ala Ile Pro His Phe Phe Thr Thr Thr Ser Ala Gly Leu Gly
 65                  70                  75                  80

Leu Tyr Ile Phe Leu Ile Ile Leu Pro Phe Ile Val Leu Cys Pro Leu
                 85                  90                  95

Tyr Phe Tyr His Glu Lys His Pro Val Asn Leu Ile Leu Leu Gly Leu
            100                 105                 110

Phe Thr Val Ala Ile Ser Phe Ala Val Gly Met Thr Cys Ala Phe Thr
        115                 120                 125

Ser Gly Lys Val Ile Leu Glu Ser Ala Ile Leu Thr Thr Val Val Val
    130                 135                 140

Leu Ser Leu Thr Ala Tyr Thr Phe Trp Ala Val Asn Arg Gly Lys Asp
145                 150                 155                 160

Phe Ser Phe Leu Gly Pro Phe Leu Phe Ala Ala Ile Ile Val Leu Leu
                165                 170                 175

Val Phe Ala Leu Ile Gln Ile Leu Phe Pro Leu Gly Lys Leu Ser Gln
            180                 185                 190

Met Ile Tyr Gly Gly Leu Ala Ser Leu Ile Phe Ser Gly Tyr Ile Val
        195                 200                 205

Tyr Asp Thr Asn Asn Ile Ile Lys Arg Tyr Thr Tyr Asp Gln Tyr Val
    210                 215                 220

Trp Ala Ala Val Ser Leu Tyr Leu Asp Val Ile Asn Leu Phe Leu Ser
225                 230                 235                 240

Leu Met Thr Leu Phe Arg Ala Ala Asp
                245
```

<210> SEQ ID NO 15
<211> LENGTH: 735
<212> TYPE: DNA
<213> ORGANISM: Glycine max
<220> FEATURE:
<221> NAME/KEY: CDS
<222> LOCATION: (1)...(735)

<400> SEQUENCE: 15

```
gca cga gcc ttc aat tcc ttc ttc gat tca aga aac cga tgg aat tac     48
Ala Arg Ala Phe Asn Ser Phe Phe Asp Ser Arg Asn Arg Trp Asn Tyr
  1               5                  10                  15 gat act ctc aaa aac ttc cgt cag att tct ccg gtc gtg cag aat cac     96
Asp Thr Leu Lys Asn Phe Arg Gln Ile Ser Pro Val Val Gln Asn His
             20                  25                  30
```

```
ctg aag cag gtt tat ttt act ctg tgt ttt gcc gtg gtt gct gcg gct    144
Leu Lys Gln Val Tyr Phe Thr Leu Cys Phe Ala Val Val Ala Ala Ala
         35                  40                  45 gtc ggg gct tac ctt cat gtc ctc ttg aac att ggg ggt ttt ctt act    192
Val Gly Ala Tyr Leu His Val Leu Leu Asn Ile Gly Gly Phe Leu Thr
 50                  55                  60 aca gtg gca tgc atg gga agc agc ttt tgg tta ctc tcc aca cct cct    240
Thr Val Ala Cys Met Gly Ser Ser Phe Trp Leu Leu Ser Thr Pro Pro
 65                  70                  75                  80 ttt gaa gag agg aag agg gtg act ttg ttg atg gcc gca tca ctg ttt    288
Phe Glu Glu Arg Lys Arg Val Thr Leu Leu Met Ala Ala Ser Leu Phe
                 85                  90                  95 cag ggt tcc tct att gga ccc ttg att gat ttg gct att cat atc gat    336
Gln Gly Ser Ser Ile Gly Pro Leu Ile Asp Leu Ala Ile His Ile Asp
             100                 105                 110 cca agc ctt atc ttt agt gca ttt gtg gga aca gct ttg gcc ttt gca    384
Pro Ser Leu Ile Phe Ser Ala Phe Val Gly Thr Ala Leu Ala Phe Ala
         115                 120                 125 tgc ttc tca gga gca gct ttg gtt gca agg cgt agg gag tac ctg tac    432
Cys Phe Ser Gly Ala Ala Leu Val Ala Arg Arg Arg Glu Tyr Leu Tyr
 130                 135                 140 ctt ggt ggc ttg gtt tct tct gga ttg tcc atc ctt ctc tgg ttg cac    480
Leu Gly Gly Leu Val Ser Ser Gly Leu Ser Ile Leu Leu Trp Leu His
145                 150                 155                 160 ttt gct tct tcc atc ttt gga ggc tca aca gct ctc ttt aag ttt gag    528
Phe Ala Ser Ser Ile Phe Gly Gly Ser Thr Ala Leu Phe Lys Phe Glu
                 165                 170                 175 ttg tac ttt ggg cta ttg gtg ttt gta ggt tac att gta gta gac acc    576
Leu Tyr Phe Gly Leu Leu Val Phe Val Gly Tyr Ile Val Val Asp Thr
             180                 185                 190 caa gaa ata gtt gag agg gca cac ttg ggc gat ctg gac tat gta aag    624
Gln Glu Ile Val Glu Arg Ala His Leu Gly Asp Leu Asp Tyr Val Lys
         195                 200                 205 cat gcc ttg acc ttg ttt acc gat ttg gtc gca gtt ttt gtc cgg att    672
His Ala Leu Thr Leu Phe Thr Asp Leu Val Ala Val Phe Val Arg Ile
 210                 215                 220 ctt gtt att atg ttg aag aat tcg act gag agg aat gag aag aaa aag    720
Leu Val Ile Met Leu Lys Asn Ser Thr Glu Arg Asn Glu Lys Lys Lys
225                 230                 235                 240 aag aga aga gat tga                                                735
Lys Arg Arg Asp *

<210> SEQ ID NO 16
<211> LENGTH: 244
<212> TYPE: PRT
<213> ORGANISM: Glycine max

<400> SEQUENCE: 16

Ala Arg Ala Phe Asn Ser Phe Phe Asp Ser Arg Asn Arg Trp Asn Tyr
 1               5                  10                  15

Asp Thr Leu Lys Asn Phe Arg Gln Ile Ser Pro Val Gln Asn His
             20                  25                  30

Leu Lys Gln Val Tyr Phe Thr Leu Cys Phe Ala Val Val Ala Ala Ala
         35                  40                  45

Val Gly Ala Tyr Leu His Val Leu Leu Asn Ile Gly Gly Phe Leu Thr
 50                  55                  60

Thr Val Ala Cys Met Gly Ser Ser Phe Trp Leu Leu Ser Thr Pro Pro
 65                  70                  75                  80

Phe Glu Glu Arg Lys Arg Val Thr Leu Leu Met Ala Ala Ser Leu Phe
```

-continued

```
                    85                  90                  95
Gln Gly Ser Ser Ile Gly Pro Leu Ile Asp Leu Ala Ile His Ile Asp
            100                 105                 110
Pro Ser Leu Ile Phe Ser Ala Phe Val Gly Thr Ala Leu Ala Phe Ala
            115                 120                 125
Cys Phe Ser Gly Ala Ala Leu Val Ala Arg Arg Glu Tyr Leu Tyr
130                 135                 140
Leu Gly Gly Leu Val Ser Ser Gly Leu Ser Ile Leu Leu Trp Leu His
145                 150                 155                 160
Phe Ala Ser Ser Ile Phe Gly Gly Ser Thr Ala Leu Phe Lys Phe Glu
                165                 170                 175
Leu Tyr Phe Gly Leu Leu Val Phe Val Gly Tyr Ile Val Asp Thr
            180                 185                 190
Gln Glu Ile Val Glu Arg Ala His Leu Gly Asp Leu Asp Tyr Val Lys
            195                 200                 205
His Ala Leu Thr Leu Phe Thr Asp Leu Val Ala Val Phe Val Arg Ile
210                 215                 220
Leu Val Ile Met Leu Lys Asn Ser Thr Glu Arg Asn Glu Lys Lys Lys
225                 230                 235                 240
Lys Arg Arg Asp
```

<210> SEQ ID NO 17
<211> LENGTH: 989
<212> TYPE: DNA
<213> ORGANISM: Glycine max
<220> FEATURE:
<221> NAME/KEY: CDS
<222> LOCATION: (37)...(822)

<400> SEQUENCE: 17

```
atcacgaaaa ctatacgatt cgattccttg ttttca atg gac acc ttc ttc aat         54
                                       Met Asp Thr Phe Phe Asn
                                        1               5 tct caa tct tct tct tct tcg aga agc cgc tgg agt tac gat act ctc        102
Ser Gln Ser Ser Ser Ser Ser Arg Ser Arg Trp Ser Tyr Asp Thr Leu
         10                  15                  20 aag aat ttc cgt gag atc tct ccg ctg gtt cag aat cac atc aaa cgg        150
Lys Asn Phe Arg Glu Ile Ser Pro Leu Val Gln Asn His Ile Lys Arg
     25                  30                  35 gtt tat ttt acg tta tgt tgc gct gtg gtg gct gct gct gtt gga gct        198
Val Tyr Phe Thr Leu Cys Cys Ala Val Val Ala Ala Ala Val Gly Ala
 40                  45                  50 ttt ctt cat gtt ctg tgg aac att ggg ggt ttt ctc acc acg ttg gct        246
Phe Leu His Val Leu Trp Asn Ile Gly Gly Phe Leu Thr Thr Leu Ala
 55                  60                  65                  70 tcc att gga agc atg gtt tgg ttg cta tct aca ccc cct gtt gaa gag        294
Ser Ile Gly Ser Met Val Trp Leu Leu Ser Thr Pro Pro Val Glu Glu
             75                  80                  85 caa aag agg ttg tct ctg ttg atg gct tcg gcc ttg ttt cag ggc gct        342
Gln Lys Arg Leu Ser Leu Leu Met Ala Ser Ala Leu Phe Gln Gly Ala
         90                  95                 100 tcc att gga cct ctg att gat ttg gct att gcc att gat cct agc ctt        390
Ser Ile Gly Pro Leu Ile Asp Leu Ala Ile Ala Ile Asp Pro Ser Leu
        105                 110                 115 att gtt agt gca ttt gtg gca act tct ttg gct ttt gct tgc ttc tct        438
Ile Val Ser Ala Phe Val Ala Thr Ser Leu Ala Phe Ala Cys Phe Ser
    120                 125                 130 gcg gca gct tta gtt gca agg cgt agg gag tac ctc tac ctt ggt ggt        486
```

```
           Ala Ala Ala Leu Val Ala Arg Arg Arg Glu Tyr Leu Tyr Leu Gly Gly
                   135                 140                 145                 150 ttg ctt tct tct ggg ctg tcc att ctt atg tgg ttg cac ttt gct tcc         534
Leu Leu Ser Ser Gly Leu Ser Ile Leu Met Trp Leu His Phe Ala Ser
                155                 160                 165 tct ctc ttt ggg ggc tca att gca ctc ttc aag ttt gag ctg tac ttt         582
Ser Leu Phe Gly Gly Ser Ile Ala Leu Phe Lys Phe Glu Leu Tyr Phe
            170                 175                 180 ggg ctt ttg gtg ttt gtg ggc tac gtt ttt gta gac act caa gaa att         630
Gly Leu Leu Val Phe Val Gly Tyr Val Phe Val Asp Thr Gln Glu Ile
            185                 190                 195 att gaa agg gct cac ttt ggt gac ctg gat tat gtg aag cat gca ttg         678
Ile Glu Arg Ala His Phe Gly Asp Leu Asp Tyr Val Lys His Ala Leu
        200                 205                 210 aca ttg ttc act gat ttg gct gca atc ttt gtg cga att ctt att ata         726
Thr Leu Phe Thr Asp Leu Ala Ala Ile Phe Val Arg Ile Leu Ile Ile
215                 220                 225                 230 atg ttg aag aat tca ttt ggg gga aat ggg aag aag aag aaa agg ggg         774
Met Leu Lys Asn Ser Phe Gly Gly Asn Gly Lys Lys Lys Lys Arg Gly
                235                 240                 245 ggt ttg ttg gct gac cga ccg act cga gct cag gct tct tta ccg taa         822
Gly Leu Leu Ala Asp Arg Pro Thr Arg Ala Gln Ala Ser Leu Pro *
            250                 255                 260 tttagtttgt gggaataca taattagctg tttagatgat gttggtcccc tgtgtagtta        882
gttagctatg tgtttgctgt aatggtaaat gtcggggttt cttttaaaca tcttcgtatg       942
tatttgccaa tatcataatg tgtcgtataa catcataacct tggtttt                    989

<210> SEQ ID NO 18
<211> LENGTH: 261
<212> TYPE: PRT
<213> ORGANISM: Glycine max

<400> SEQUENCE: 18

Met Asp Thr Phe Phe Asn Ser Gln Ser Ser Ser Ser Arg Ser Arg
  1               5                  10                  15

Trp Ser Tyr Asp Thr Leu Lys Asn Phe Arg Glu Ile Ser Pro Leu Val
                 20                  25                  30

Gln Asn His Ile Lys Arg Val Tyr Phe Thr Leu Cys Cys Ala Val Val
             35                  40                  45

Ala Ala Ala Val Gly Ala Phe Leu His Val Leu Trp Asn Ile Gly Gly
         50                  55                  60

Phe Leu Thr Thr Leu Ala Ser Ile Gly Ser Met Val Trp Leu Leu Ser
 65                  70                  75                  80

Thr Pro Pro Val Glu Glu Gln Lys Arg Leu Ser Leu Leu Met Ala Ser
                 85                  90                  95

Ala Leu Phe Gln Gly Ala Ser Ile Gly Pro Leu Ile Asp Leu Ala Ile
                100                 105                 110

Ala Ile Asp Pro Ser Leu Ile Val Ser Ala Phe Val Ala Thr Ser Leu
            115                 120                 125

Ala Phe Ala Cys Phe Ser Ala Ala Leu Val Ala Arg Arg Arg Glu
        130                 135                 140

Tyr Leu Tyr Leu Gly Gly Leu Leu Ser Ser Gly Leu Ser Ile Leu Met
145                 150                 155                 160

Trp Leu His Phe Ala Ser Ser Leu Phe Gly Gly Ser Ile Ala Leu Phe
                165                 170                 175

Lys Phe Glu Leu Tyr Phe Gly Leu Leu Val Phe Val Gly Tyr Val Phe
```

```
                    180                 185                 190
Val Asp Thr Gln Glu Ile Ile Glu Arg Ala His Phe Gly Asp Leu Asp
            195                 200                 205

Tyr Val Lys His Ala Leu Thr Leu Phe Thr Asp Leu Ala Ala Ile Phe
        210                 215                 220

Val Arg Ile Leu Ile Ile Met Leu Lys Asn Ser Phe Gly Gly Asn Gly
225                 230                 235                 240

Lys Lys Lys Lys Arg Gly Gly Leu Leu Ala Asp Arg Pro Thr Arg Ala
                245                 250                 255

Gln Ala Ser Leu Pro
            260

<210> SEQ ID NO 19
<211> LENGTH: 234
<212> TYPE: DNA
<213> ORGANISM: glycine max
<220> FEATURE:
<221> NAME/KEY: CDS
<222> LOCATION: (1)...(234)

<400> SEQUENCE: 19 ggg ggc tca att gca ctc ttc aag ttt gag ctg tac ttt ggg ctt ttg      48
Gly Gly Ser Ile Ala Leu Phe Lys Phe Glu Leu Tyr Phe Gly Leu Leu
  1               5                  10                  15 gtg ttt gtg ggc tac gtt ata gta gac act caa gaa att att gaa agg      96
Val Phe Val Gly Tyr Val Ile Val Asp Thr Gln Glu Ile Ile Glu Arg
                 20                  25                  30 gct cac ttt ggt gac ctg gat tat gtg aag cat gca ttg aca ttg ttc     144
Ala His Phe Gly Asp Leu Asp Tyr Val Lys His Ala Leu Thr Leu Phe
             35                  40                  45 act gat ttg gct gca atc ttt gtg cga att ctt att ata atg ttg aag     192
Thr Asp Leu Ala Ala Ile Phe Val Arg Ile Leu Ile Ile Met Leu Lys
         50                  55                  60 aat tca tct gag aga aat gag aag aag aag aaa agg aga gat             234
Asn Ser Ser Glu Arg Asn Glu Lys Lys Lys Lys Arg Arg Asp
 65                  70                  75

<210> SEQ ID NO 20
<211> LENGTH: 78
<212> TYPE: PRT
<213> ORGANISM: glycine max

<400> SEQUENCE: 20

Gly Gly Ser Ile Ala Leu Phe Lys Phe Glu Leu Tyr Phe Gly Leu Leu
  1               5                  10                  15

Val Phe Val Gly Tyr Val Ile Val Asp Thr Gln Glu Ile Ile Glu Arg
                 20                  25                  30

Ala His Phe Gly Asp Leu Asp Tyr Val Lys His Ala Leu Thr Leu Phe
             35                  40                  45

Thr Asp Leu Ala Ala Ile Phe Val Arg Ile Leu Ile Ile Met Leu Lys
         50                  55                  60

Asn Ser Ser Glu Arg Asn Glu Lys Lys Lys Lys Arg Arg Asp
 65                  70                  75

<210> SEQ ID NO 21
<211> LENGTH: 803
<212> TYPE: DNA
<213> ORGANISM: glycine max
<220> FEATURE:
<221> NAME/KEY: CDS
<222> LOCATION: (2)...(0)
```

-continued

<400> SEQUENCE: 21

| ctcactaaag ggaacaaaag ctggagctcc accgcggtgg cggccgctct agaactagtg | 60 |
| gatccccccgg gctgcaggct attatggtac atatatttgt catgttatat actataacat | 120 |
| atcttccggg ggtacttatt tgcaattctt gcagctgtac tttgggcttt tggtgtttgt | 180 |
| gggctacgtt atagtagaca ctcaagaaat tattgaaagg gctcactttg gtgacctgga | 240 |
| ttatgtgaag catgcattga cattgttcac tgatttggct gcaatctttg tgcgaattct | 300 |
| tattataatg gtgagttgga ccagttctta ttggtgttct ttcttttttg tttcctcccg | 360 |
| ttgaattggt attcacaagg ttcttatcct ttcacagttg aagaattcat ctgagagaaa | 420 |
| tgagaagaag aagaaaagga gagattagta ggctgaccga ccgactcgag ctcaggcttc | 480 |
| tctacagtaa tttagtttgt ggagaataca taattagctg tttagatgat gttggtccct | 540 |
| tgtgtagtta gttagctatg tgtttgctgt aatggtaaat gtcaggattt cttttaaaca | 600 |
| tcttcatatg tatttgccaa tatcataatg tgtcgtataa catcataccct tggtttaagc | 660 |
| agcatgttga cgaaaccttc actaaatttt attttttgggt ttagtttatt ttatacatta | 720 |
| agtggacaat gcagccgaca tatattttga atcaatagga tagccctttc aggatgtgct | 780 |
| attctaatag acttgctttt aac | 803 |

<210> SEQ ID NO 22
<211> LENGTH: 308
<212> TYPE: DNA
<213> ORGANISM: glycine max
<220> FEATURE:
<221> NAME/KEY: misc_feature
<222> LOCATION: (1)...(308)
<223> OTHER INFORMATION: n = A,T,C or G

<400> SEQUENCE: 22

| tgcatttgtg ggaacatcct tggcctttgc atgcttctca ggagcagctt tggttgctag | 60 |
| gcgtagggag tacctgtacc ttggtggctt ggtttcttct ggattgtcca tccttctctg | 120 |
| gttgcacttt gcttcttcca tctttggagg ttcaacagct ctctttaagt ttgagttgta | 180 |
| ctttgggctt ttggtgtttg taggttacat tgtagtagac acccaaagaa atagttgaga | 240 |
| nggcacactt gggcgatctg gactatgtaa agcatgcctt gaccttgttt accgatttgg | 300 |
| ntgcaatt | 308 |

<210> SEQ ID NO 23
<211> LENGTH: 741
<212> TYPE: DNA
<213> ORGANISM: glycine max
<220> FEATURE:
<221> NAME/KEY: misc_feature
<222> LOCATION: (1)...(741)
<223> OTHER INFORMATION: n = A,T,C or G

<400> SEQUENCE: 23

| atgtttgagc cgcagcagct atacactcga gcgaagaccg aggaattcga cctcgaatca | 60 |
| ggggaaaccc tctacccagg gctgagcgtc ggcgagaacc agctccgatg gggcttcatc | 120 |
| cgcaaggtct acggcatcct ctccgcccag atcgtcctca ccaccctcgt ctctgtcacc | 180 |
| accgttttct atactccaat caatgacctc ctcaagggca attccaccct cctcctcatc | 240 |
| ctcctcttcc ttcctttcat cttttttgatt cccctgttga agtaccaagc aagaagcatc | 300 |
| ctcataatta catcttgctt gcactcttca acgtgtctat caagctccaa ccgtccggag | 360 |

| | |
|---|---:|
| tcaacttgcg ccaacaccga cgggaaaatt gtgcttgagg ccttgatttt gacctccgct | 420 |
| ggtgggtttc atctcttaac cgggttatgc cttttgggcg tccaagaagg gcaaggattt | 480 |
| tagcttcctt ggcccaatrt tgttcacctc cctctttact ctcatcctca ctggcatgat | 540 |
| gcagatgttc ttccctcttg gacctactgc ccatgctatc tatggtgcaa ttggtgctat | 600 |
| gattttctct ggctatattg tgtacgacac tgacaacctg atcaagcgnt tcacttatga | 660 |
| tgagtacatt ggagcctcng tnactcttta tcttgacata ctcaacctct tccttttccat | 720 |
| cttraggatc ctcngggang c | 741 |

```
<210> SEQ ID NO 24
<211> LENGTH: 953
<212> TYPE: DNA
<213> ORGANISM: glycine max
<220> FEATURE:
<221> NAME/KEY: CDS
<222> LOCATION: (88)...(879)

<400> SEQUENCE: 24
```

| | |
|---|---:|
| gctaaattac tttctttcca ttttccttcg ttttctctct ctttctcagt ttctcagttt | 60 |
| ctcagtcatc accatcgcag cagcaag atg tgg aac caa cca ttc gga aaa acc<br>                                   Met Trp Asn Gln Pro Phe Gly Lys Thr<br>                                    1                5 | 114 |
| gat ttg gaa agc ggt tct cgg cct ctg tat ccg atg atg ctc gag agc<br>Asp Leu Glu Ser Gly Ser Arg Pro Leu Tyr Pro Met Met Leu Glu Ser<br>10                  15                  20                  25 | 162 |
| cct gaa ctg cgg tgg tcg ttc atc aga aaa gtg tac tcc ata atc gcc<br>Pro Glu Leu Arg Trp Ser Phe Ile Arg Lys Val Tyr Ser Ile Ile Ala<br>                  30                  35                  40 | 210 |
| atc cag ttg ctc gta acc atc gtc gtc ggc gcc gtc gtc gtc acc gtc<br>Ile Gln Leu Leu Val Thr Ile Val Val Gly Ala Val Val Val Thr Val<br>                  45                  50                  55 | 258 |
| cgc cca atc agt gtc ttc ttc gcc acc acc ggc gcc gga ctg gct ctc<br>Arg Pro Ile Ser Val Phe Phe Ala Thr Thr Gly Ala Gly Leu Ala Leu<br>          60                  65                  70 | 306 |
| tac atc gtc ctc att ttt gtt ccc ttt ata acg ttg tgt cca ctt tac<br>Tyr Ile Val Leu Ile Phe Val Pro Phe Ile Thr Leu Cys Pro Leu Tyr<br>75                  80                  85 | 354 |
| tac tat tcc cag aag cat ccc gtc aat tac ttg ctc cta ggg gtt ttc<br>Tyr Tyr Ser Gln Lys His Pro Val Asn Tyr Leu Leu Leu Gly Val Phe<br>90                  95                  100                105 | 402 |
| act gtg tct ctt gga ttt gtc gtt gga ttg agt tgc gcc ttt act agc<br>Thr Val Ser Leu Gly Phe Val Val Gly Leu Ser Cys Ala Phe Thr Ser<br>                  110                  115                120 | 450 |
| gag aaa gtt att ctg gaa gct gtc ata ttg act gct gtg gtg gtg att<br>Glu Lys Val Ile Leu Glu Ala Val Ile Leu Thr Ala Val Val Val Ile<br>                  125                  130                135 | 498 |
| ggt ctg act cta tac aca ttt tgg gct gca agg aga ggc cat gat ttc<br>Gly Leu Thr Leu Tyr Thr Phe Trp Ala Ala Arg Arg Gly His Asp Phe<br>          140                  145                  150 | 546 |
| aac ttc ctt ggc ccc ttc ttg ttt ggt gct gtg cta gtt ctc atg gtc<br>Asn Phe Leu Gly Pro Phe Leu Phe Gly Ala Val Leu Val Leu Met Val<br>155                  160                  165 | 594 |
| ttt gct ctg att cag gtt ctg ttt cca ctg ggt aaa ttg tcc gtg atg<br>Phe Ala Leu Ile Gln Val Leu Phe Pro Leu Gly Lys Leu Ser Val Met<br>170                  175                  180                185 | 642 |
| atc tat ggt tgc ttg gca gcc att ata ttt tgt ggc tac atc atc tat<br>Ile Tyr Gly Cys Leu Ala Ala Ile Ile Phe Cys Gly Tyr Ile Ile Tyr<br>                  190                  195                200 | 690 |

```
gac aca gac aac ctg atc aag aga tac tcg tac gat gaa tac atc tgg      738
Asp Thr Asp Asn Leu Ile Lys Arg Tyr Ser Tyr Asp Glu Tyr Ile Trp
        205                 210                 215 gct tcg atc tcc ttg tat ctg gac atc atc aac ctc ttc ctg tct ctg      786
Ala Ser Ile Ser Leu Tyr Leu Asp Ile Ile Asn Leu Phe Leu Ser Leu
            220                 225                 230 ctc act att ttt aga gcc gct gat agt tag atc att gtg tca tat tca      834
Leu Thr Ile Phe Arg Ala Ala Asp Ser  *  Ile Ile Val Ser Tyr Ser
        235                 240                 245 aat att ccg ttc ctt gcc tgc aca tta ttt gtt ttc tgt gat gag          879
Asn Ile Pro Phe Leu Ala Cys Thr Leu Phe Val Phe Cys Asp Glu
            250                 255                 260 ggtgggttct gaaaacaaa ttcttgtcaa ttaataaatc tttggggctt gctttgtcgc     939
aaggtgtctt gtgt                                                      953

<210> SEQ ID NO 25
<211> LENGTH: 263
<212> TYPE: PRT
<213> ORGANISM: glycine max

<400> SEQUENCE: 25

Met Trp Asn Gln Pro Phe Gly Lys Thr Asp Leu Glu Ser Gly Ser Arg
 1               5                  10                  15

Pro Leu Tyr Pro Met Met Leu Glu Ser Pro Glu Leu Arg Trp Ser Phe
            20                  25                  30

Ile Arg Lys Val Tyr Ser Ile Ile Ala Ile Gln Leu Leu Val Thr Ile
        35                  40                  45

Val Val Gly Ala Val Val Thr Val Arg Pro Ile Ser Val Phe Phe
    50                  55                  60

Ala Thr Thr Gly Ala Gly Leu Ala Leu Tyr Ile Val Leu Ile Phe Val
65                  70                  75                  80

Pro Phe Ile Thr Leu Cys Pro Leu Tyr Tyr Tyr Ser Gln Lys His Pro
                85                  90                  95

Val Asn Tyr Leu Leu Leu Gly Val Phe Thr Val Ser Leu Gly Phe Val
            100                 105                 110

Val Gly Leu Ser Cys Ala Phe Thr Ser Glu Lys Val Ile Leu Glu Ala
        115                 120                 125

Val Ile Leu Thr Ala Val Val Ile Gly Leu Thr Leu Tyr Thr Phe
    130                 135                 140

Trp Ala Ala Arg Arg Gly His Asp Phe Asn Phe Leu Gly Pro Phe Leu
145                 150                 155                 160

Phe Gly Ala Val Leu Val Leu Met Val Phe Ala Leu Ile Gln Val Leu
                165                 170                 175

Phe Pro Leu Gly Lys Leu Ser Val Met Ile Tyr Gly Cys Leu Ala Ala
            180                 185                 190

Ile Ile Phe Cys Gly Tyr Ile Ile Tyr Asp Thr Asp Asn Leu Ile Lys
        195                 200                 205

Arg Tyr Ser Tyr Asp Glu Tyr Ile Trp Ala Ser Ile Ser Leu Tyr Leu
    210                 215                 220

Asp Ile Ile Asn Leu Phe Leu Ser Leu Leu Thr Ile Phe Arg Ala Ala
225                 230                 235                 240

Asp Ser Ile Ile Val Ser Tyr Ser Asn Ile Pro Phe Leu Ala Cys Thr
                245                 250                 255

Leu Phe Val Phe Cys Asp Glu
            260
```

-continued

```
<210> SEQ ID NO 26
<211> LENGTH: 1130
<212> TYPE: DNA
<213> ORGANISM: glycine max
<220> FEATURE:
<221> NAME/KEY: CDS
<222> LOCATION: (109)...(837)

<400> SEQUENCE: 26
ttgggtaacg ccagggtttt cccagtcacg acgttgtaaa acgacggcca gtgagcgcgc         60
gtaatacgac tcactatagg gcgaattggg taccgggccc cccccaag atg tgg aac        117
                                                    Met Trp Asn
                                                      1 caa cca ttg gga aaa acc gat ttg gaa agc ggt tct cgc ccg ctg tat        165
Gln Pro Leu Gly Lys Thr Asp Leu Glu Ser Gly Ser Arg Pro Leu Tyr
  5                  10                  15 ccg atg atg ctt gag agc ccc gaa ctg cgc tgg tct ttc atc aga aaa        213
Pro Met Met Leu Glu Ser Pro Glu Leu Arg Trp Ser Phe Ile Arg Lys
 20                  25                  30                  35 gta tac tcc ata atc gcc ata cag ttg ctc gta acc atc gtc gtc ggc        261
Val Tyr Ser Ile Ile Ala Ile Gln Leu Leu Val Thr Ile Val Val Gly
                 40                  45                  50 gcc gtc gtc gtc acc gtc cgc cca atc agc gtc ttc ttc gcc acc acc        309
Ala Val Val Val Thr Val Arg Pro Ile Ser Val Phe Phe Ala Thr Thr
             55                  60                  65 ggc gcc gga ttg gct ctc tac atc gtc ctc atc ttt gtc ccc ttc atc        357
Gly Ala Gly Leu Ala Leu Tyr Ile Val Leu Ile Phe Val Pro Phe Ile
         70                  75                  80 aca ttg tgt cca ctt tac tac tac tcc cag aag cat ccc gtc aat tac        405
Thr Leu Cys Pro Leu Tyr Tyr Tyr Ser Gln Lys His Pro Val Asn Tyr
 85                  90                  95 ttg ctc cta gca gtt ttc acc gtg tct ctt ggt ttt gtc gtt gga ttg        453
Leu Leu Leu Ala Val Phe Thr Val Ser Leu Gly Phe Val Val Gly Leu
100                 105                 110                 115 agt tgc gcc ttt act agc gag aaa gtt att ctg gaa gct gtc ata ttg        501
Ser Cys Ala Phe Thr Ser Glu Lys Val Ile Leu Glu Ala Val Ile Leu
                120                 125                 130 act gct gtg gtg gtg att gct cta aca ctc tac aca ttt tgg gct gca        549
Thr Ala Val Val Val Ile Ala Leu Thr Leu Tyr Thr Phe Trp Ala Ala
            135                 140                 145 agg aga ggc cat gat ttc aac ttc ctt gga ccc ttc ttg ttt ggt gca        597
Arg Arg Gly His Asp Phe Asn Phe Leu Gly Pro Phe Leu Phe Gly Ala
        150                 155                 160 gtg cta gtt ctt atg gtc ttt gct ctg att cag gtt ctg ttt cca ctg        645
Val Leu Val Leu Met Val Phe Ala Leu Ile Gln Val Leu Phe Pro Leu
165                 170                 175 ggt aaa ttg tcc gtg atg atc tat ggt tgc ttg gca gcc att ata ttt        693
Gly Lys Leu Ser Val Met Ile Tyr Gly Cys Leu Ala Ala Ile Ile Phe
180                 185                 190                 195 tgc ggc tac atc atc tat gac aca gac aac ctg atc aag aga tac tcg        741
Cys Gly Tyr Ile Ile Tyr Asp Thr Asp Asn Leu Ile Lys Arg Tyr Ser
                200                 205                 210 tac gat gaa tac att tgg gct tcg atc tcc ttg tat ctg gac atc att        789
Tyr Asp Glu Tyr Ile Trp Ala Ser Ile Ser Leu Tyr Leu Asp Ile Ile
            215                 220                 225 aac ctc ttc ctg tct ctg ctc act att ttc aga gcc gct gat agt tag        837
Asn Leu Phe Leu Ser Leu Leu Thr Ile Phe Arg Ala Ala Asp Ser *
        230                 235                 240 atcattgtgt catatgcaat tccgttcctt gcctgcacat tatttgtttt ttgtggggga       897
```

| | |
|---|---:|
| cgagagtggg ttccgaaaac aaattcttgt caactagtat atctttgggg cttgctctgt | 957 |
| tgctaggtgt ctagtataca atggattatt gtcaaaagtt gttcataaat agtagattag | 1017 |
| cgatgaaatt ttgtacttga ttataaacac gactttccct ttcttatttg tgttccttat | 1077 |
| tgtttatatt agaatacaag atataatata tggggcattg gctcatgata tgg | 1130 |

<210> SEQ ID NO 27
<211> LENGTH: 242
<212> TYPE: PRT
<213> ORGANISM: glycine max

<400> SEQUENCE: 27

```
Met Trp Asn Gln Pro Leu Gly Lys Thr Asp Leu Glu Ser Gly Ser Arg
 1               5                  10                  15

Pro Leu Tyr Pro Met Met Leu Glu Ser Pro Glu Leu Arg Trp Ser Phe
            20                  25                  30

Ile Arg Lys Val Tyr Ser Ile Ile Ala Ile Gln Leu Leu Val Thr Ile
        35                  40                  45

Val Val Gly Ala Val Val Thr Val Arg Pro Ile Ser Val Phe Phe
    50                  55                  60

Ala Thr Thr Gly Ala Gly Leu Ala Leu Tyr Ile Val Leu Ile Phe Val
65                  70                  75                  80

Pro Phe Ile Thr Leu Cys Pro Leu Tyr Tyr Tyr Ser Gln Lys His Pro
                85                  90                  95

Val Asn Tyr Leu Leu Leu Ala Val Phe Thr Val Ser Leu Gly Phe Val
            100                 105                 110

Val Gly Leu Ser Cys Ala Phe Thr Ser Glu Lys Val Ile Leu Glu Ala
        115                 120                 125

Val Ile Leu Thr Ala Val Val Val Ile Ala Leu Thr Leu Tyr Thr Phe
    130                 135                 140

Trp Ala Ala Arg Arg Gly His Asp Phe Asn Phe Leu Gly Pro Phe Leu
145                 150                 155                 160

Phe Gly Ala Val Leu Val Leu Met Val Phe Ala Leu Ile Gln Val Leu
                165                 170                 175

Phe Pro Leu Gly Lys Leu Ser Val Met Ile Tyr Gly Cys Leu Ala Ala
            180                 185                 190

Ile Ile Phe Cys Gly Tyr Ile Ile Tyr Asp Thr Asp Asn Leu Ile Lys
        195                 200                 205

Arg Tyr Ser Tyr Asp Glu Tyr Ile Trp Ala Ser Ile Ser Leu Tyr Leu
    210                 215                 220

Asp Ile Ile Asn Leu Phe Leu Ser Leu Leu Thr Ile Phe Arg Ala Ala
225                 230                 235                 240

Asp Ser
```

<210> SEQ ID NO 28
<211> LENGTH: 1053
<212> TYPE: DNA
<213> ORGANISM: glycine max
<220> FEATURE:
<221> NAME/KEY: CDS
<222> LOCATION: (103)...(843)

<400> SEQUENCE: 28

| | |
|---|---:|
| gccgctctag aactagtgga tcccccgggc tgcaggaatt cggcaccaga gaagaagaag | 60 |
| gttggttgat tggtcccatt gattccgaag agaaaagaaa ag atg ttt gag cca<br>                                                                            Met Phe Glu Pro<br>                                                                            1 | 114 |

| | | | | | | | | | | | | | | |
|---|---|---|---|---|---|---|---|---|---|---|---|---|---|---|
| caa | cag | cta | tac | act | cgc | gcg | aag | acc | gag | gaa | ttc | gac | ctc | gaa tca | 162 |
| Gln | Gln | Leu | Tyr | Thr | Arg | Ala | Lys | Thr | Glu | Glu | Phe | Asp | Leu | Glu Ser |
| 5 | | | | 10 | | | | | 15 | | | | | 20 |

| | | | | | | | | | | | | | | |
|---|---|---|---|---|---|---|---|---|---|---|---|---|---|---|
| gga | gaa | acc | ctc | tac | cca | ggg | ctg | agc | gtc | ggc | gag | aac | cag | ctc cga | 210 |
| Gly | Glu | Thr | Leu | Tyr | Pro | Gly | Leu | Ser | Val | Gly | Glu | Asn | Gln | Leu Arg |
| | | | 25 | | | | | 30 | | | | | 35 | |

| | | | | | | | | | | | | | | |
|---|---|---|---|---|---|---|---|---|---|---|---|---|---|---|
| tgg | ggt | ttc | atc | cgc | aag | gtc | tac | ggc | atc | ctc | tcc | gcg | cag | atc gtc | 258 |
| Trp | Gly | Phe | Ile | Arg | Lys | Val | Tyr | Gly | Ile | Leu | Ser | Ala | Gln | Ile Val |
| | | | 40 | | | | | 45 | | | | | 50 | |

| | | | | | | | | | | | | | | |
|---|---|---|---|---|---|---|---|---|---|---|---|---|---|---|
| ctc | acc | acc | ctc | gtc | tcc | gtc | acc | acc | gtt | ttc | tat | act | cca | atc aat | 306 |
| Leu | Thr | Thr | Leu | Val | Ser | Val | Thr | Thr | Val | Phe | Tyr | Thr | Pro | Ile Asn |
| | | 55 | | | | | 60 | | | | | 65 | | |

| | | | | | | | | | | | | | | |
|---|---|---|---|---|---|---|---|---|---|---|---|---|---|---|
| gac | ctc | ctc | aag | ggc | aat | tcc | acc | ctc | ctc | ctc | atc | ctc | ctc | ttc ctt | 354 |
| Asp | Leu | Leu | Lys | Gly | Asn | Ser | Thr | Leu | Leu | Leu | Ile | Leu | Leu | Phe Leu |
| | 70 | | | | | 75 | | | | | 80 | | | |

| | | | | | | | | | | | | | | |
|---|---|---|---|---|---|---|---|---|---|---|---|---|---|---|
| ccc | ttc | atc | ttt | ttg | att | ccc | ctg | ttg | aag | tac | cag | cag | aag | cat cct | 402 |
| Pro | Phe | Ile | Phe | Leu | Ile | Pro | Leu | Leu | Lys | Tyr | Gln | Gln | Lys | His Pro |
| 85 | | | | | 90 | | | | | 95 | | | | | 100 |

| | | | | | | | | | | | | | | |
|---|---|---|---|---|---|---|---|---|---|---|---|---|---|---|
| cat | aat | tac | atc | ttg | ctt | gca | ctc | ttc | acc | gtg | tcg | atc | agt | tcc acc | 450 |
| His | Asn | Tyr | Ile | Leu | Leu | Ala | Leu | Phe | Thr | Val | Ser | Ile | Ser | Ser Thr |
| | | | | 105 | | | | | 110 | | | | | 115 |

| | | | | | | | | | | | | | | |
|---|---|---|---|---|---|---|---|---|---|---|---|---|---|---|
| atc | gga | gtc | acc | tgt | gcc | aac | acc | gac | ggg | aaa | att | gtg | ctt | gag gct | 498 |
| Ile | Gly | Val | Thr | Cys | Ala | Asn | Thr | Asp | Gly | Lys | Ile | Val | Leu | Glu Ala |
| | | | 120 | | | | | 125 | | | | | 130 | |

| | | | | | | | | | | | | | | |
|---|---|---|---|---|---|---|---|---|---|---|---|---|---|---|
| ttg | att | ttg | acc | tcc | gct | gtg | gtt | tca | tct | ctt | act | ggc | tat | gcc ttt | 546 |
| Leu | Ile | Leu | Thr | Ser | Ala | Val | Val | Ser | Ser | Leu | Thr | Gly | Tyr | Ala Phe |
| | | 135 | | | | | 140 | | | | | 145 | | |

| | | | | | | | | | | | | | | |
|---|---|---|---|---|---|---|---|---|---|---|---|---|---|---|
| tgg | gcg | tcc | aag | aag | ggc | aag | gat | ttt | agc | ttc | ctt | ggc | cca | ata ttg | 594 |
| Trp | Ala | Ser | Lys | Lys | Gly | Lys | Asp | Phe | Ser | Phe | Leu | Gly | Pro | Ile Leu |
| | 150 | | | | | 155 | | | | | 160 | | | |

| | | | | | | | | | | | | | | |
|---|---|---|---|---|---|---|---|---|---|---|---|---|---|---|
| ttc | acc | tcc | ctc | att | act | ctc | atc | ctc | act | ggc | atg | atg | cag | atg ttc | 642 |
| Phe | Thr | Ser | Leu | Ile | Thr | Leu | Ile | Leu | Thr | Gly | Met | Met | Gln | Met Phe |
| 165 | | | | | 170 | | | | | 175 | | | | | 180 |

| | | | | | | | | | | | | | | |
|---|---|---|---|---|---|---|---|---|---|---|---|---|---|---|
| ttc | cct | ctt | gga | cct | act | gcc | cat | gct | atc | tat | ggt | gca | att | ggt gct | 690 |
| Phe | Pro | Leu | Gly | Pro | Thr | Ala | His | Ala | Ile | Tyr | Gly | Ala | Ile | Gly Ala |
| | | | | 185 | | | | | 190 | | | | | 195 |

| | | | | | | | | | | | | | | |
|---|---|---|---|---|---|---|---|---|---|---|---|---|---|---|
| atg | ata | ttc | tct | ggc | tac | att | gtg | tat | gac | act | gac | aac | ctg | atc aag | 738 |
| Met | Ile | Phe | Ser | Gly | Tyr | Ile | Val | Tyr | Asp | Thr | Asp | Asn | Leu | Ile Lys |
| | | | 200 | | | | | 205 | | | | | 210 | |

| | | | | | | | | | | | | | | |
|---|---|---|---|---|---|---|---|---|---|---|---|---|---|---|
| cgt | ttc | act | tat | gat | gag | tac | att | gga | gcc | tct | gtt | act | ctt | tat ctt | 786 |
| Arg | Phe | Thr | Tyr | Asp | Glu | Tyr | Ile | Gly | Ala | Ser | Val | Thr | Leu | Tyr Leu |
| | | 215 | | | | | 220 | | | | | 225 | | |

| | | | | | | | | | | | | | | |
|---|---|---|---|---|---|---|---|---|---|---|---|---|---|---|
| gac | ata | ctc | aac | ctc | ttc | ctt | tcc | atc | tta | agg | atc | ctc | aga | gag gca | 834 |
| Asp | Ile | Leu | Asn | Leu | Phe | Leu | Ser | Ile | Leu | Arg | Ile | Leu | Arg | Glu Ala |
| | 230 | | | | | 235 | | | | | 240 | | | |

| | | | | | | | | | |
|---|---|---|---|---|---|---|---|---|---|
| aat | aat | tag | tcatatcgag | gttgagtaat | accaaacaaa | ttcaaaaga | | | 883 |
| Asn | Asn | * | | | | | | | |
| 245 | | | | | | | | | | ctatgttgct tctttatttt tatttttgt gactatgttg cttctttata gtataccgta  943 ggaagtattg tgaaacataa taacaccgtg cttctcttgt actcccttac agcttatgat  1003 acttttgatg acatgaaatt taaagcttta caattgtatg tatgcgtgat  1053

<210> SEQ ID NO 29
<211> LENGTH: 246
<212> TYPE: PRT
<213> ORGANISM: glycine max

<400> SEQUENCE: 29

```
Met Phe Glu Pro Gln Gln Leu Tyr Thr Arg Ala Lys Thr Glu Glu Phe
 1               5                  10                  15

Asp Leu Glu Ser Gly Glu Thr Leu Tyr Pro Gly Leu Ser Val Gly Glu
            20                  25                  30

Asn Gln Leu Arg Trp Gly Phe Ile Arg Lys Val Tyr Gly Ile Leu Ser
        35                  40                  45

Ala Gln Ile Val Leu Thr Thr Leu Val Ser Val Thr Thr Val Phe Tyr
 50                  55                  60

Thr Pro Ile Asn Asp Leu Leu Lys Gly Asn Ser Thr Leu Leu Leu Ile
65                  70                  75                  80

Leu Leu Phe Leu Pro Phe Ile Phe Leu Ile Pro Leu Leu Lys Tyr Gln
            85                  90                  95

Gln Lys His Pro His Asn Tyr Ile Leu Leu Ala Leu Phe Thr Val Ser
            100                 105                 110

Ile Ser Ser Thr Ile Gly Val Thr Cys Ala Asn Thr Asp Gly Lys Ile
            115                 120                 125

Val Leu Glu Ala Leu Ile Leu Thr Ser Ala Val Val Ser Ser Leu Thr
130                 135                 140

Gly Tyr Ala Phe Trp Ala Ser Lys Lys Gly Lys Asp Phe Ser Phe Leu
145                 150                 155                 160

Gly Pro Ile Leu Phe Thr Ser Leu Ile Thr Leu Ile Leu Thr Gly Met
                165                 170                 175

Met Gln Met Phe Phe Pro Leu Gly Pro Thr Ala His Ala Ile Tyr Gly
                180                 185                 190

Ala Ile Gly Ala Met Ile Phe Ser Gly Tyr Ile Val Tyr Asp Thr Asp
            195                 200                 205

Asn Leu Ile Lys Arg Phe Thr Tyr Asp Glu Tyr Ile Gly Ala Ser Val
        210                 215                 220

Thr Leu Tyr Leu Asp Ile Leu Asn Leu Phe Leu Ser Ile Leu Arg Ile
225                 230                 235                 240

Leu Arg Glu Ala Asn Asn
                245

<210> SEQ ID NO 30
<211> LENGTH: 403
<212> TYPE: DNA
<213> ORGANISM: glycine max
<220> FEATURE:
<221> NAME/KEY: misc_feature
<222> LOCATION: (1)...(403)
<223> OTHER INFORMATION: n = A,T,C or G

<400> SEQUENCE: 30
atgaaaanag atgttgaaag cggtggggat ggcaatgcca atcccaggcc actctacccc      60
gccatgcttg agaancctca actccgttgg gccttcattc gcaaggncta caccatcctc     120
accattcaag ttgctcctca ccatcgccgt cgcctccgtc gtccgtcttc gttcgcccca     180
tcgctctttt cttccgtttc ctcccccgga ggccttgctc tttacattgt cctcctcant     240
gctccattga taactggtgt gtccgcttta ctattaccac caagaaacac cnnctgaatt     300
acatccttct cttcantttc accgttacgt tagccnttgc nggntggatt ggacttgcgc     360
cnttactaan nggnagaatt aatnctggga atctggtgat aat                       403

<210> SEQ ID NO 31
<211> LENGTH: 1026
<212> TYPE: DNA
<213> ORGANISM: Zea mays
```

```
<220> FEATURE:
<221> NAME/KEY: CDS
<222> LOCATION: (72)...(830)

<400> SEQUENCE: 31
cctcgatcgg cctccctccc ccaagatcct ccactcgatc caaacaaac caacaaatcc        60 atccatcgca c atg gac gcg ttc ttc tcg gcc tcc tcc gcg tcg gcg ccc      110
            Met Asp Ala Phe Phe Ser Ala Ser Ser Ala Ser Ala Pro
             1               5                  10 tac ggc tac ggc gcc ggc gga tgg agc tac gac tcg ctc aag aac ttc        158
Tyr Gly Tyr Gly Ala Gly Gly Trp Ser Tyr Asp Ser Leu Lys Asn Phe
 15                  20                  25 cgc cag atc acc ccc gcc gtc cag acc cac ctc aag ctc gtc tac ctc        206
Arg Gln Ile Thr Pro Ala Val Gln Thr His Leu Lys Leu Val Tyr Leu
 30                  35                  40                  45 acc ctg tgc gcg gcg ctg gcc tcg tcg gcg gtg ggc gct tac ctg cac        254
Thr Leu Cys Ala Ala Leu Ala Ser Ser Ala Val Gly Ala Tyr Leu His
                 50                  55                  60 gtg gtc tgg aac atc ggc ggt acg ctg aca atg ctc ggt tgc gtc ggc        302
Val Val Trp Asn Ile Gly Gly Thr Leu Thr Met Leu Gly Cys Val Gly
         65                  70                  75 agc atc gcc tgg ctc ttc tcg gtg ccc gtc tac gag gag agg aag agg        350
Ser Ile Ala Trp Leu Phe Ser Val Pro Val Tyr Glu Glu Arg Lys Arg
 80                  85                  90 tat ggg ctg ctg atg gcg gct gcc ctc ctg gaa ggc gct tcg gtc gga        398
Tyr Gly Leu Leu Met Ala Ala Ala Leu Leu Glu Gly Ala Ser Val Gly
 95                 100                 105 ccc ctc gtc aag ctc gcc gtg gaa ttt gac cca agc atc ctg gtg acg        446
Pro Leu Val Lys Leu Ala Val Glu Phe Asp Pro Ser Ile Leu Val Thr
110                 115                 120                 125 gcg ttc gtg ggg act gcc atc gcg ttc gcg tgc ttc acc ggc gcg gcc        494
Ala Phe Val Gly Thr Ala Ile Ala Phe Ala Cys Phe Thr Gly Ala Ala
                130                 135                 140 atg gtg gcc agg cgc agg gag tac ctc tac ctg ggt ggg ctg ctc tcg        542
Met Val Ala Arg Arg Arg Glu Tyr Leu Tyr Leu Gly Gly Leu Leu Ser
        145                 150                 155 tcg ggg ctc tcc atc ctg ctc tgg ctg cag cta gcc ggc tcc atc ttc        590
Ser Gly Leu Ser Ile Leu Leu Trp Leu Gln Leu Ala Gly Ser Ile Phe
    160                 165                 170 ggc cac tcc gca acc agc ttc atg ttc gag gtc tac ttc ggg ctg ctc        638
Gly His Ser Ala Thr Ser Phe Met Phe Glu Val Tyr Phe Gly Leu Leu
175                 180                 185 atc ttc ctg ggc tac gtg gtg tac gac acg cag gag atc atc gag agg        686
Ile Phe Leu Gly Tyr Val Val Tyr Asp Thr Gln Glu Ile Ile Glu Arg
190                 195                 200                 205 gcg cac cgc ggc gac atg gac cac gtc aag cac gcc ctc acc ctc ttc        734
Ala His Arg Gly Asp Met Asp His Val Lys His Ala Leu Thr Leu Phe
                210                 215                 220 aca gac ttc gtg gcc gtc ctc gtc cgc gtc ctc gtc atc atg ctc aag        782
Thr Asp Phe Val Ala Val Leu Val Arg Val Leu Val Ile Met Leu Lys
                225                 230                 235 aac ggg gcc gac aag tcg gag gac aag aag agg aag aag agg tcg tga        830
Asn Gly Ala Asp Lys Ser Glu Asp Lys Lys Arg Lys Lys Arg Ser   *
        240                 245                 250 gcgcgtccag aagggaagct cttccacttc cacatatgca taggagtaac tgctggggtt       890
ccttcctggg gtggaagtgt ggaactgagc tgagtgttca aaagtgttc ctttgttcgg        950 caactttgtt ctccttcctc tcttgaagag tctgtaaata actatgtcaa tctgggttaa      1010
gcttggtttg ggtgcc                                                      1026
```

<210> SEQ ID NO 32
<211> LENGTH: 252
<212> TYPE: PRT
<213> ORGANISM: Zea mays

<400> SEQUENCE: 32

```
Met Asp Ala Phe Phe Ser Ala Ser Ser Ala Pro Tyr Gly Tyr
 1               5                  10                  15
Gly Ala Gly Gly Trp Ser Tyr Asp Ser Leu Lys Asn Phe Arg Gln Ile
                20                  25                  30
Thr Pro Ala Val Gln Thr His Leu Lys Leu Val Tyr Leu Thr Leu Cys
            35                  40                  45
Ala Ala Leu Ala Ser Ser Ala Val Gly Ala Tyr Leu His Val Val Trp
 50                  55                  60
Asn Ile Gly Gly Thr Leu Thr Met Leu Gly Cys Val Gly Ser Ile Ala
 65                  70                  75                  80
Trp Leu Phe Ser Val Pro Val Tyr Glu Glu Arg Lys Arg Tyr Gly Leu
                85                  90                  95
Leu Met Ala Ala Ala Leu Leu Glu Gly Ala Ser Val Gly Pro Leu Val
                100                 105                 110
Lys Leu Ala Val Glu Phe Asp Pro Ser Ile Leu Val Thr Ala Phe Val
            115                 120                 125
Gly Thr Ala Ile Ala Phe Ala Cys Phe Thr Gly Ala Ala Met Val Ala
130                 135                 140
Arg Arg Arg Glu Tyr Leu Tyr Leu Gly Gly Leu Leu Ser Ser Gly Leu
145                 150                 155                 160
Ser Ile Leu Leu Trp Leu Gln Leu Ala Gly Ser Ile Phe Gly His Ser
                165                 170                 175
Ala Thr Ser Phe Met Phe Glu Val Tyr Phe Gly Leu Leu Ile Phe Leu
                180                 185                 190
Gly Tyr Val Val Tyr Asp Thr Gln Glu Ile Ile Glu Arg Ala His Arg
            195                 200                 205
Gly Asp Met Asp His Val Lys His Ala Leu Thr Leu Phe Thr Asp Phe
    210                 215                 220
Val Ala Val Leu Val Arg Val Leu Val Ile Met Leu Lys Asn Gly Ala
225                 230                 235                 240
Asp Lys Ser Glu Asp Lys Lys Arg Lys Lys Arg Ser
                245                 250
```

<210> SEQ ID NO 33
<211> LENGTH: 1138
<212> TYPE: DNA
<213> ORGANISM: Zea mays
<220> FEATURE:
<221> NAME/KEY: CDS
<222> LOCATION: (136)...(912)

<400> SEQUENCE: 33

```
cccacgcgtc cgcccacgcg tccgaagcca tagccacgac acgactccat tcccagattc      60
aaatccatcc atcccatcca tccatccatc catccgcagc gggcaggcac acacacaggc     120
tttgcgttgg caggg atg gac gcg ttc tac tcg acc acc gcc tcc tcc tcc     171
               Met Asp Ala Phe Tyr Ser Thr Thr Ala Ser Ser Ser
                 1               5                  10 acg tcg tcg gcg ccg tac ggc ggc ggc gaa ggc tgg ggc tac gac          219
Thr Ser Ser Ala Pro Tyr Gly Gly Gly Glu Gly Trp Gly Tyr Asp
        15                  20                  25
```

```
tcg atg aag aac ttc cgc cag atc agc ccc gcc gtc cag acc cac ctc      267
Ser Met Lys Asn Phe Arg Gln Ile Ser Pro Ala Val Gln Thr His Leu
     30                  35                  40 aag ctc gtt tac ctc acc cta tgc gtg gcg ctg gcc tcg tcg gcg gtg      315
Lys Leu Val Tyr Leu Thr Leu Cys Val Ala Leu Ala Ser Ser Ala Val
 45                  50                  55                  60 ggc gcg tac ctg cac gtc gtc tgg aac atc ggc ggg atg ctg acc atg      363
Gly Ala Tyr Leu His Val Val Trp Asn Ile Gly Gly Met Leu Thr Met
                 65                  70                  75 ctc ggc tgc gtc ggc agc atc gcc tgg ctc ttc tcg gtg ccc gtc tac      411
Leu Gly Cys Val Gly Ser Ile Ala Trp Leu Phe Ser Val Pro Val Tyr
             80                  85                  90 gag gag agg aag agg tac tgg ctg ctg atg gcg gct gcc ctc ctg gaa      459
Glu Glu Arg Lys Arg Tyr Trp Leu Leu Met Ala Ala Ala Leu Leu Glu
         95                 100                 105 ggg gcg tcg gtt gga ccc ctc atc aag ctc gcc gtg gaa ttt gac cca      507
Gly Ala Ser Val Gly Pro Leu Ile Lys Leu Ala Val Glu Phe Asp Pro
     110                 115                 120 agc atc ctg gtg aca gcg ttc gtg ggg act gcc att gcg ttc gcg tgc      555
Ser Ile Leu Val Thr Ala Phe Val Gly Thr Ala Ile Ala Phe Ala Cys
125                 130                 135                 140 ttc tct tgc gcg gcc atg gtg gcc aag cgc agg gag tac ctc tac ctg      603
Phe Ser Cys Ala Ala Met Val Ala Lys Arg Arg Glu Tyr Leu Tyr Leu
                145                 150                 155 ggc ggg ctg ctc tct tct ggc ctc tcc atc ctg ctc tgg ctg cag ttc      651
Gly Gly Leu Leu Ser Ser Gly Leu Ser Ile Leu Leu Trp Leu Gln Phe
            160                 165                 170 gcc gcc tcc atc ttc ggc cac caa tcc act agc agc ttc atg ttt gag      699
Ala Ala Ser Ile Phe Gly His Gln Ser Thr Ser Ser Phe Met Phe Glu
        175                 180                 185 gtc tac ttt ggg ctg ctc atc ttc ctg ggc tac atg gtg tac gac acg      747
Val Tyr Phe Gly Leu Leu Ile Phe Leu Gly Tyr Met Val Tyr Asp Thr
    190                 195                 200 cag gag gtc atc gag agg gcg cac cac ggc gac atg gac tac atc aag      795
Gln Glu Val Ile Glu Arg Ala His His Gly Asp Met Asp Tyr Ile Lys
205                 210                 215                 220 cac gcc ctc acc ctc ttc acc gac ttc gtg gct gtc ctt gtc cgc atc      843
His Ala Leu Thr Leu Phe Thr Asp Phe Val Ala Val Leu Val Arg Ile
                225                 230                 235 ctt gtc atc atg ctc aag aac gcg gct gac aag tcg gag gac aag agg      891
Leu Val Ile Met Leu Lys Asn Ala Ala Asp Lys Ser Glu Asp Lys Arg
            240                 245                 250 agg aag agg agg agt tgg tga aaatctgtgt gcgaacacag cactcaaggg aa      944
Arg Lys Arg Arg Ser Trp *
        255 gggaaggaag gcactggtgc gtctgaaatg aagctcccac ataactaggt gtatacatat     1004 ataggagcga ggagttactt tggggtggaa ctgacctgtg caagtgtcgt tcctttgttt     1064 tctcttgatc tgtcatcagt gagcctgttg atagttttgt cctgtcctgt gaatgaatat     1124 gacaaatctc cccc                                                       1138

<210> SEQ ID NO 34
<211> LENGTH: 258
<212> TYPE: PRT
<213> ORGANISM: Zea mays

<400> SEQUENCE: 34

Met Asp Ala Phe Tyr Ser Thr Thr Ala Ser Ser Thr Ser Ser Ala
 1               5                  10                  15
```

-continued

```
Pro Tyr Gly Gly Gly Glu Gly Trp Gly Tyr Asp Ser Met Lys Asn
            20              25              30

Phe Arg Gln Ile Ser Pro Ala Val Gln Thr His Leu Lys Leu Val Tyr
        35              40              45

Leu Thr Leu Cys Val Ala Leu Ala Ser Ser Ala Val Gly Ala Tyr Leu
    50              55              60

His Val Val Trp Asn Ile Gly Gly Met Leu Thr Met Leu Gly Cys Val
65              70              75              80

Gly Ser Ile Ala Trp Leu Phe Ser Val Pro Val Tyr Glu Glu Arg Lys
            85              90              95

Arg Tyr Trp Leu Leu Met Ala Ala Leu Leu Glu Gly Ala Ser Val
            100             105             110

Gly Pro Leu Ile Lys Leu Ala Val Glu Phe Asp Pro Ser Ile Leu Val
            115             120             125

Thr Ala Phe Val Gly Thr Ala Ile Ala Phe Ala Cys Phe Ser Cys Ala
    130             135             140

Ala Met Val Ala Lys Arg Arg Glu Tyr Leu Tyr Leu Gly Gly Leu Leu
145             150             155             160

Ser Ser Gly Leu Ser Ile Leu Leu Trp Leu Gln Phe Ala Ala Ser Ile
            165             170             175

Phe Gly His Gln Ser Thr Ser Ser Phe Met Phe Glu Val Tyr Phe Gly
            180             185             190

Leu Leu Ile Phe Leu Gly Tyr Met Val Tyr Asp Thr Gln Glu Val Ile
            195             200             205

Glu Arg Ala His His Gly Asp Met Asp Tyr Ile Lys His Ala Leu Thr
    210             215             220

Leu Phe Thr Asp Phe Val Ala Val Leu Val Arg Ile Leu Val Ile Met
225             230             235             240

Leu Lys Asn Ala Ala Asp Lys Ser Glu Asp Lys Arg Arg Lys Arg Arg
            245             250             255

Ser Trp
    258
```

ANTI-APOPTOSIS GENES AND METHODS OF USE THEREOF

CROSS REFERENCE TO RELATED APPLICATIONS

This application claims priority to U.S. application Ser. No. 60/297,478 filed Jun. 12, 2001, the disclosure of which is incorporated herein by reference.

TECHNICAL FIELD

The present invention relates generally to plant molecular biology. More specifically, it relates to nucleic acids and methods for modulating their expression in plants.

BACKGROUND OF THE INVENTION

Cell division plays a crucial role during all phases of plant development. The continuation of organogenesis and growth responses to a changing environment requires precise spatial, temporal and developmental regulation of cell division activity in meristems (and in cells with the capability to form new meristems such as in lateral root formation). Such control of cell division is also important in organs themselves (i.e. separate from meristems per se), for example, in leaf expansion, secondary growth, and endoreduplication.

A complex network controls cell proliferation in eukaryotes. Various regulatory pathways communicate environmental constraints, such as nutrient availability, mitogenic signals such as growth factors or hormones, or developmental cues such as the transition from vegetative to reproductive stages. Ultimately, these regulatory pathways control the timing, frequency (rate), plane and position of cell divisions.

Plants have unique developmental features that distinguish them from other eukaryotes. Plant cells do not migrate, and thus only cell division, expansion and programmed cell death determine morphogenesis. Organs are formed throughout the entire life span of the plant from specialized regions called meristems. In addition, many differentiated cells have the potential to both dedifferentiate and to reenter the cell cycle. There are also numerous examples of plant cell types that undergo endoreduplication, a process involving nuclear multiplication without cytokinesis. The study of plant cell cycle control genes is expected to contribute to the understanding of these unique phenomena. O. Shaul et al., Regulation of Cell Division in Arabidopsis, *Critical Reviews in Plant Sciences* 15 (2):97–112 (1996).

Current transformation technology provides an opportunity to engineer plants with desired traits. Major advances in plant transformation have occurred over the last few years. However, in many major crop plants, serious genotype limitations still exist. Transformation of some agronomically important crop plants continues to be both difficult and time consuming. For example, it is difficult to obtain a culture response from some maize varieties. Typically, a suitable culture response has been obtained by optimizing medium components and/or explant material and source. This has led to success in some, but not all, genotypes. While, transformation of model genotypes is efficient, the process of introgressing transgenes into production inbreds is laborious, expensive and time consuming. It would save considerable time and money if genes could be introduced into and evaluated directly in commercial hybrids.

Current methods for genetic engineering in maize require a specific cell type as the recipient of new DNA. These cells are found in relatively undifferentiated, rapidly growing callus cells or on the scutellar surface of the immature embryo (which gives rise to callus). Irrespective of the delivery method currently used, DNA is introduced into literally thousands of cells, yet transformants are recovered at frequencies of $10^{-5}$ relative to transiently-expressing cells. Exacerbating this problem, the trauma that accompanies DNA introduction directs recipient cells into cell cycle arrest and accumulating evidence suggests that many of these cells are directed into apoptosis or programmed cell death. (Reference Bowen et al., Tucson International Mol. Biol. Meetings). Therefore, it would be desirable to provide improved methods capable of increasing transformation efficiency by reducing cell death in a number of cell types.

Despite the number of identified plant diseases and stresses, the understanding of the molecular and cellular events that are responsible for plant disease and stress resistance remains rudimentary. This is especially true of the events controlling the earliest steps of active plant defense, recognition of a potential pathogen and transfer of the cognitive signal throughout the cell, surrounding tissue and cell death within that tissue.

Diseases are particularly destructive processes resulting from specific causes and characterized by specific symptoms. Generally the symptoms can be related to a specific cause, usually a pathogenic organism. In plants, a variety of pathogenic organisms cause a wide variety of disease symptoms. It would therefore be valuable to develop new methods that contribute to the increase in crop yield to protect plants against cell death associated with pathogen and stress.

In spite of increases in yield and harvested area worldwide, it is predicted that over the next ten years, meeting the demand for corn will require an additional 20% increase over current production (Dowswell, C. R., Paliwal, R. L., Cantrell, R. P. (1996) Maize in the Third World, Westview Press, Boulder, Colo.).

The components most often associated with maize productivity are grain yield or whole-plant harvest for animal feed (in the forms of silage, fodder, or stover). Thus the relative growth of the vegetative or reproductive organs might be increased or decreased, depending on the ultimate use of the crop. Whether the whole plant or the ear are harvested, overall yield will depend strongly on vigor and growth rate. It would therefore be valuable to develop new methods that contribute to the increase in crop yield.

SUMMARY OF THE INVENTION

The invention provides isolated BI nucleic acids and their encoded proteins that act as cell death inhibitors and methods of using to improve transformation, improve stress resistance, disease resistance, change the architecture of a plant and affect male sterility. The invention further provides expression cassettes, transformed host cells, transgenic plants and plant parts, and antibody compositions.

DETAILED DESCRIPTION OF THE INVENTION

Apoptosis is an evolutionarily conserved form of cell death that plays crucial roles in the development and homeostasis of multicellular animals. It is brought about by the action of a group of cysteine proteases, called caspases.

Modulation of the BI gene may affect apoptosis. Introducing BI into plants can improve transformation, increase disease and stress resistance and increase agronomic advantage.

Definitions

The term "isolated" refers to material, such as a nucleic acid or a protein, which is: (1) substantially or essentially free from components which normally accompany or interact with the material as found in its naturally occurring environment or (2) if the material is in its natural environment, the material has been altered by deliberate human intervention to a composition and/or placed at a locus in the cell other than the locus native to the material.

As used herein, "nucleic acid" means a polynucleotide and includes single or double-stranded polymer of deoxyribonucleotide or ribonucleotide bases. Nucleic acids may also include fragments and modified nucleotides.

As used herein, "polynucleotide" includes reference to a deoxyribopolynucleotide, ribopolynucleotide, or analogs thereof, that have the essential nature of a natural ribonucleotide in that they hybridize to nucleic acids in a manner similar to naturally occurring nucleotides. A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art.

As used herein, "BI polynucleotide" means a nucleic acid sequence of BI.

As used herein, "polypeptide" means proteins, protein fragments, proteins, amino acid sequences and synthetic amino acid sequences. The polypeptide may be glycosylated or not.

As used herein, "BI polypeptide" means a polypeptide comprising at least 200 bp of the BI amino acid coding sequence, including fusions with other polypeptides such as VirE. The BI polypeptide may inhibit Bax-induced cell death or not.

As used herein, "BI activity" or "Bax inhibitor activity" means the BI polypeptides or fragments or fusions thereof that inhibit Bax-induced cell death and may be measurable by standard methods such as DNA fragmentation, visual necrosis or genetic assays. "Bax inhibitor activity" may be measurable or detectable through increased transformation efficiency, increased co- or re-transformation efficiency, increased identification of transgenic events, improved disease resistance, improved stress resistance, modulation of plant architecture, and/or modulation of sterility.

As used herein, "plant" includes plants and plant parts including but not limited to plant cells, plant tissue such as leaves, stems, roots, flowers, and seeds.

As used herein, "promoter" includes reference to a region of DNA upstream from the start of transcription and involved in recognition and binding of RNA polymerase and other proteins to initiate transcription.

By "fragment" is intended a portion of the nucleotide sequence or a portion of the amino acid sequence and hence protein encoded thereby. Fragments of a nucleotide sequence may encode protein fragments that retain the biological activity of the native nucleic acid. Alternatively, fragments of a nucleotide sequence that are useful as hybridization probes may not encode fragment proteins retaining biological activity. Thus, fragments of a nucleotide sequence are generally greater than 25, 50, 100, 200, 300, 400, 500, 600, or 700 nucleotides and up to and including the entire nucleotide sequence encoding the proteins of the invention. Generally the probes are less than 1000 nucleotides and preferably less than 500 nucleotides. Fragments of the invention include antisense sequences used to decrease expression of the inventive polynucleotides. Such antisense fragments may vary in length ranging from greater than 25, 50, 100, 200, 300, 400, 500, 600, or 700 nucleotides and up to and including the entire coding sequence.

By "functional equivalent" as applied to a polynucleotide or a protein is intended a polynucleotide or a protein of sufficient length to modulate the level of BI activity in a plant cell. A polynucleotide functional equivalent can be in sense or antisense orientation.

By "variants" is intended substantially similar sequences. Generally, nucleic acid sequence variants of the invention will have at least 51%, 55%, 57%, 60%, 63%, 65%, 67%, 69%, 70%, 72%, 73%, 75%, 77%, 78%, 80%, 81%, 83%, 84%, 87%, 88%, 90%, 91%, 92%, 93%, 94%, 95%, 96%, 97%, 98% or 99% sequence identity to the native nucleotide sequence, wherein the % sequence identity is based on the amino acid coding region available for the inventive sequence and is determined by GAP 10 analysis using default parameters. Generally, polypeptide sequence variants of the invention will have at least about 60%, 63%, 65%, 67%, 70%, 73%, 75%, 78%, 80%, 83%, 85%, 87%, 88%, 90%, 93%, 95%, 98% or 99% sequence identity to the native protein, wherein the % sequence identity is based on the entire sequence and is determined by GAP 10 analysis using default parameters and is any integer. GAP uses the algorithm of Needleman and Wunsch (J. Mol. Biol. 48:443–453, 1970) to find the alignment of two complete sequences that maximizes the number of matches and minimizes the number of gaps.

The public databases were searched by BLAST using default parameters for the closest related sequences to each of the seven maize or ten soybean BI homolog genes in question. The comparison was done, wherever possible, using the nucleotide coding regions of the maize or soybean BI genes in a global alignment (GAP) with the closest public counterpart. The closest 'hit' was determined by a combination of the percent identity between the two sequences times the ratio of the amino acid coding region that that public sequences represented relative to the BI genes of the present invention. So, for example if a public BI EST is 100% identical at the nucleotide level, but it only represents 30% of the coding region of the proprietary BI gene, then it is expressed as 30% related. Conversely, if a public full-length cDNA represents 100% of the coding region, but is only 70% identical at the nucleotide level, then it is expressed as only 70% related. In this way the closest public relative to each of the seven maize and ten soybean BI genes was determined.

As used herein a "responsive cell" refers to a cell that exhibits a positive response to the introduction of BI polypeptide or BI polynucleotide compared to a cell that has not been introduced with BI polypeptide or BI polynucleotide. The response can be to enhance tissue culture response, induce somatic embryogenesis, increase transformation efficiency or increase recovery of regenerated plants.

As used herein a "recalcitrant plant cell" is a plant cell that exhibits unsatisfactory tissue culture response, transformation efficiency or recovery of regenerated plants compared to model systems. In maize such a model system is Hi-II. Elite maize inbreds are typically recalcitrant. In soybeans such model systems are Peking or Jack.

As used herein "Transformation" includes stable transformation and transient transformation unless indicated otherwise.

As used herein "Stable Transformation" refers to the transfer of a nucleic acid fragment into a genome of a host organism (this includes both nuclear and organelle genomes) resulting in genetically stable and heritable inheritance. In addition to traditional methods, stable transformation includes the alteration of gene expression by any means including chimerplasty or transposon insertion.

As used herein "Transient Transformation" refers to the transfer of a nucleic acid fragment or protein into the nucleus (or DNA-containing organelle) of a host organism resulting in gene expression without integration and stable inheritance.

As used herein "Transformation Efficiency" refers to parameters involved in improving transformation favorably, that influence transformation and/or regeneration and thus result in an increased recovery of transformed resultants (i.e. callus, shoots, plants) from a transformation attempt. Transformation efficiency may be calculated as the number of transformed resultants divided by the number of targets having DNA introduced times 100. For a review related to callus formation see, for example, Duncan et al, (*Planta* 165:322–332, 1985).

As used herein, "Co-introduced" refers to situations where 2 or more nucleic acids, proteins or combinations thereof, are introduced into the target at the same time.

As used herein, a "BI-DR" (BI-Down Regulated) construct as an expression cassette whose transcribed mRNA or translated protein will diminish the functional expression of active BI in the cell. Such silencing can be achieved through expression of an antisense construct targeted against the BI structural gene, a vector in which the BI structural gene or a portion of this sequence is used to make a silencing hairpin (or where silencing hairpin is conjoined to the BI sequence in some fashion), or where a BI-overexpression cassette is used to co-suppress endogenous BI levels. Reducing activity of endogenous BI protein can also be achieved through expression of a transgene encoding an antibody (including single chain antibodies) directed against a functional domain within the BI molecule, introduction of such an antibody or through introduction of an "aptamer".

As used herein, "aptamers" are DNA or RNA molecules that have been artificially evolved and selected to bind other proteins (such as BI), molecules, viruses, etc. They have many potential uses in medicine and technology. For example see J. Feigon, T. Dieckmann, and F. W. Smith: "Aptamer structures from A to zeta", *Chem. and Biol.* 3:611–617 (1996).

As used herin, "architecture" refers to the structural organization, placement, relative shape and/or relative size (e.g. organ placement/presence/size, such as ear).

Seq. ID No. 1-ZmBI-1 nucleotide sequence
Seq. ID No. 2-ZmBI-1 protein sequence
Seq. ID No. 3-ZmBI-2 nucleotide sequence
Seq. ID No. 4-ZmBI-2 protein sequence
Seq. ID No. 5-ZmBI-3 nucleotide sequence
Seq. ID No. 6-ZmBI-3 protein sequence
Seq. ID No. 7-ZmBI-4 nucleotide sequence
Seq. ID No. 8-ZmBI-4 protein sequence
Seq. ID No. 9-ZmBI-5 nucleotide sequence
Seq. ID No. 10-ZmBI-5 protein sequence
Seq. ID No. 11-ZmBI-6 nucleotide sequence
Seq. ID No. 12-ZmBI-6 protein sequence
Seq. ID No. 13-ZmBI-7 nucleotide sequence
Seq. ID No. 14-ZmBI-7 protein sequence
Seq. ID No. 15-GmBI-1 nucleotide sequence
Seq. ID No. 16-GmBI-1 protein sequence
Seq. ID No. 17-GmBI-2 nucleotide sequence
Seq. ID No. 18-GmBI-2 protein sequence
Seq. ID No. 19-GmBI-3 nucleotide sequence
Seq. ID No. 20-GmBI-3 protein sequence
Seq. ID No. 21-GmBI-4 nucleotide sequence
Seq. ID No. 22-GmBI-5 nucleotide sequence
Seq. ID No. 23-GmBI-6 nucleotide sequence
Seq. ID No. 24-GmBI-7 nucleotide sequence
Seq. ID No. 25-GmBI-7 protein sequence
Seq. ID No. 26-GmBI-8 nucleotide sequence
Seq. ID No. 27-GmBI-8 protein sequence
Seq. ID No. 28-GmBI-9 nucleotide sequence
Seq. ID No. 29-GmBI-9 protein sequence
Seq. ID No. 30-GmBI-10 nucleotide sequence
Seq. ID No. 31-ZmBI-2 amended nucleotide sequence
Seq. ID No. 32-ZmBI-2 amended protein sequence
Seq. ID No. 33-ZmBI-3 amended nucleotide sequence
Seq. ID No. 34-ZmBI-3 amended protein sequence Nucleic Acids Plant cell death occurs through the course of normal plant development, and helps sculpt the plants life-cycle, from embryo development, to scutellum and aleurone degeneration during germination, to leaf and fruit abscission, to plant senescence, as in annual crop plants. In addition plant cell death can occur in stressful situations such as mechanical wounding, as from wind-blown sand, hail, and insect foraging, and from other biotic stresses such as fungal, bacterial and viral infection. Methods of introducing DNA into cells, cell culture and selection techniques involved in transformation can also increase cell death.

Crop plants are vulnerable to various abiotic stresses, which can cause tissue damage and necrosis. These stresses include water stress, temperature stress, light stress, and mechanical stress. Water stress can be insufficient water or drought stress, but also flooding or stress. Temperature stress can be excessive or prolonged heat or cold. Light stress can occur as well, and can be exasperated by temperature and water stress. For example, light reflected off standing water can cause hyper-exposure to light, as on the underside of leaves, and 'burn' the crop plants. This is more commonly a problem for young soybean and maize plants where foliage cover between the rows has not yet occurred. Mechanical stress can be caused by factors such as wind and hail, the former causing aggravated damage should wind-blown particles, such as sand, pock the plant tissues. Because the BI genes are inhibitors of cell death, their appropriate (usually ectopic) expression, as in a transgenic plant, could cause suppression of death brought by these abiotic stresses. As death is a primary adverse symptom of these stresses, this suppression of the death response would reduce the severity of the abiotic stress symptoms, and thus the crop plants would be more 'tolerant' to these stresses.

The BI genes of this invention then may find a number of applications for agronomic advantages and transformation improvement of a plant via methods to control plant cell death. In general ectopic expression of BI would retard cell death and promote viable tissue. Conversely reducing BI expression would promote cell death. By "expression" we mean ultimately the capacity of the function of the gene product, a protein, that may be controlled via a number of means, including mRNA levels, protein levels, and modifications of amino acids sites on the protein to effect altered functional capacity of the protein itself.

Increasingly various genetic engineering strategies are being put forth to create enhanced disease resistance using recombinant DNA technology and transgenic plants. Sometimes this involves isolation of a resistance gene and then discreetly inserting it into a susceptible plant by transformation. For example, this was done for the Xa21 gene of rice. Other strategies involve engineering elevated expression of antimicrobial compounds or genes, such as PR or pathogenesis-related proteins like chitinase and beta-glucanase, or genes which alter reactive oxygen species, which are known to be antimicrobial and/or stimulators of plant defense systems. Other strategies are also being tried.

These genetic engineering strategies are meeting with varied success. No one strategy or gene has proven to be a panacea, although some show limited promise. Successful broad improvement of crop resistance will likely require multiple strategies. This is so for several reasons. One is that no one strategy seems to work for every pathogen; in fact, often the resistance created is either specific for particular pathogens or small groups of pathogens. Another reason is that the resistance created is often not robust enough or limited to tissue or genetic background. Yet another reason is that given the continuing evolution of the pathogen, no one strategy is likely to work for long.

This invention provides novel genes and novel descriptions of how they can be used, as in a transgenic plant, to effect enhancement transformation, and disease or stress resistance of that crop plant.

This invention overcomes the limitations of previous related genetic engineering strategies for crop plants by providing seven novel maize genes and ten novel soybean genes for such purposes. These genes are called *Zea mays* and *Glycine max* BI genes, or Zm-BI and Gm-BI for short, based on their structural similarity to the bax inhibitor genes of animals, and likewise based on their presumed related function to these animal bax inhibitor genes. It is recognized that no single gene will work in all crops against all pathogens. This invention can complement conventional breeding strategies and other genetic engineering methods to enhance disease/stress resistance and increase transformation frequencies in plants.

Other Possible Applications for these BI Genes

While the examples described herewithin are limited to the areas of plant transformation and disease/stress resistance and agronomic traits, other applications can be envisioned.

First, plants can be wounded abiotically, as by drought stress, wind stress (which includes damage by wind-blown soil particles), and chemical and nutrient stress. Such stresses can precipitate cell death that can affect plant yield. To the extent that BI may retard cell death, they may be able to retard the symptom development of necrosis results from these stresses, for example with a death-inducible promoter. As such, BI might prove agronomically advantageous.

Second, the BI genes may have application in the development and implementation of herbicide resistance mechanisms in crop plants. Ectopic expression of the BI genes, as in leaves, may result in a retardation of cell death that could occur following application of herbicides. We recognize that this would be subject of the kind of herbicide and its mode of action, but it is a possible area of use for these genes. Herbicides and herbicide resistance systems are often used as selectable markers in plant transformation experiments. So in a way similar to the herbicide resistance application, these BI genes could figure in as selectable markers—only cells expressing the BI genes (sic ectopically) would grow or stay alive in the face of an antibiotic/herbicide medium. This application of course starts to overlap with the examples given above for improving plant transformation.

Third, the BI genes might be useful for affecting the architecture (organ placement/presence and/or structural organization) of a plant. This may be accomplished, for example, by controlling the senescence of crop plants, whole plants or special tissues. It is recognized that maturity and dry-down are important agronomic traits in maize and other crop plants. While the biology is undoubtedly complex in senescence, in the extent of their ability to control cell death, BI may be able to control the timing and onset of senescence. For certain crops particular tissue or organs are desired to senesce. This includes controlled dropping of cotton leaves to facilitate cotton ball harvesting. Sometimes organs are desired not to senesce, as in the petioles of fruit; premature fruit drop can cause loss of yield. Modulation of BI may provide agronomic advantages by promoting or delaying senescence and other developmental signals.

The isolated nucleic acids of the present invention can be made using (a) standard recombinant methods, (b) synthetic techniques, or combinations thereof. In some embodiments, the polynucleotides of the present invention will be cloned, amplified, or otherwise constructed from a monocot or dicot. Typical examples of monocots are corn, sorghum, barley, wheat, millet, rice, or turf grass. Typical dicots include soybeans, sunflower, canola, alfalfa, potato, or cassava.

Functional fragments included in the invention can be obtained using primers that selectively hybridize under stringent conditions or through enzyme restriction. Primers are generally at least 12 bases in length and can be as high as 200 bases, but will generally be from 15 to 75, preferably from 15 to 50 bases. Functional fragments can be identified using a variety of techniques such as restriction analysis, Southern analysis, primer extension analysis, and DNA sequence analysis.

The present invention includes a plurality of polynucleotides that encode for the identical amino acid sequence. The degeneracy of the genetic code allows for such "silent variations" which can be used, for example, to selectively hybridize and detect allelic variants of polynucleotides of the present invention. Additionally, the present invention includes isolated nucleic acids comprising allelic variants. The term "allele" as used herein refers to a related nucleic acid of the same gene.

Variants of nucleic acids included in the invention can be obtained, for example, by oligonucleotide-directed mutagenesis, linker-scanning mutagenesis, mutagenesis using the polymerase chain reaction, and the like. See, for example, Ausubel, pages 8.0.3–8.5.9. Also, see generally, McPherson (ed.), *DIRECTED MUTAGENESIS: A Practical Approach*, (IRL Press, 1991). Thus, the present invention also encompasses DNA molecules comprising nucleotide sequences that have substantial sequence similarity with the inventive sequences.

Variants included in the invention may contain individual substitutions, deletions or additions to the nucleic acid or polypeptide sequences which alters, adds or deletes a single amino acid or a small percentage of amino acids in the encoded sequence is a "conservatively modified variant" where the alteration results in the substitution of an amino acid with a chemically similar amino acid. When the nucleic acid is prepared or altered synthetically, advantage can be taken of known codon preferences of the intended host.

The present invention also includes "shufflents" produced by sequence shuffling of the inventive polynucleotides to obtain a desired characteristic. Sequence shuffling is described in PCT publication No. 96/19256. See also, Zhang, J. H., et al., *Proc. Natl. Acad. Sci. USA* 94:4504–4509 (1997).

The present invention also includes the use of 5' and/or 3' UTR regions for modulation of translation of heterologous coding sequences. Positive sequence motifs include translational initiation consensus sequences (Kozak, *Nucleic Acids Res.*15:8125 (1987)) and the 7-methylguanosine cap structure (Drummond et al., *Nucleic Acids Res.* 13:7375 (1985)). Negative elements include stable intramolecular 5' UTR stem-loop structures (Muesing et al., *Cell* 48:691 (1987)) and AUG sequences or short open reading frames preceded by an appropriate AUG in the 5' UTR (Kozak, supra, Rao et al., *Mol. and Cell. Biol.* 8:284 (1988)).

Further, the polypeptide-encoding segments of the polynucleotides of the present invention can be modified to alter codon usage. Altered codon usage can be employed to alter translational efficiency. Codon usage in the coding regions of the polynucleotides of the present invention can be analyzed statistically using commercially available software packages such as "Codon Preference" available from the University of Wisconsin Genetics Computer Group (see Devereaux et al., *Nucleic Acids Res.* 12:387–395 (1984)) or MacVector 4.1 (Eastman Kodak Co., New Haven, Conn.).

For example, the inventive nucleic acids can be optimized for enhanced expression in plants of interest. See, for example, EPA0359472; WO 91/16432; Perlak et al. (1991) *Proc. Natl. Acad. Sci. USA* 88:3324–3328; and Murray et al. (1989) *Nucleic Acids Res.* 17:477–498. In this manner, the polynucleotides can be synthesized utilizing plant-preferred codons. See, for example, Murray et al. (1989) *Nucleic Acids Res.* 17:477–498, the disclosure of which is incorporated herein by reference.

The present invention provides subsequences comprising isolated nucleic acids containing at least 20 contiguous bases of the inventive sequences. For example the isolated nucleic acid includes those comprising at least 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 220, 225, 230, 235, 240, 245, 250, 255, 260, 265, 270, 275, 280, 285, 290, 295, 300, 305, 310, 315, 320, 330, 335, 340, 345, 350, 355, 360, 365, 370, 375, 380, 385, 390, 395, 400, 405, 410, 415, 420, 425, 430, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, or 600 contiguous nucleotides of the inventive sequences. Subsequences of the isolated nucleic acid can be used to modulate or detect gene expression by introducing into the subsequences compounds which bind, intercalate, cleave and/or crosslink to nucleic acids.

The nucleic acids of the invention may conveniently comprise a multi-cloning site comprising one or more endonuclease restriction sites inserted into the nucleic acid to aid in isolation of the polynucleotide. Also, translatable sequences may be inserted to aid in the isolation of the translated polynucleotide of the present invention. For example, a hexa-histidine marker sequence provides a convenient means to purify the proteins of the present invention.

A polynucleotide of the present invention can be attached to a vector, adapter, promoter, transit peptide or linker for cloning and/or expression of a polynucleotide of the present invention. Additional sequences may be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers is well known and extensively described in the art. For a description of such nucleic acids see, for example, Stratagene Cloning Systems, Catalogs 1995, 1996, 1997 (La Jolla, Calif.); and, Amersham Life Sciences, Inc, Catalog '97 (Arlington Heights, Ill.).

The isolated nucleic acid compositions of this invention, such as RNA, cDNA, genomic DNA, or a hybrid thereof, can be obtained from plant biological sources using any number of cloning methodologies known to those of skill in the art. In some embodiments, oligonucleotide probes that selectively hybridize, under stringent conditions, to the polynucleotides of the present invention are used to identify the desired sequence in a cDNA or genomic DNA library.

Exemplary total RNA and mRNA isolation protocols are described in *Plant Molecular biology: A Laboratory Manual*, Clark, Ed., Springer-Verlag, Berlin (1997); and, *Current Protocols in Molecular Biology*, Ausubel et al., Eds., Greene Publishing and Wiley-Interscience, New York (1995). Total RNA and mRNA isolation kits are commercially available from vendors such as Stratagene (La Jolla, Calif.), Clonetech (Palo Alto, Calif.), Pharmacia (Piscataway, N.J.), and 5'–3' (Paoli, Pa.). See also, U.S. Pat. Nos. 5,614,391; and, 5,459,253.

Typical cDNA synthesis protocols are well known to the skilled artisan and are described in such standard references as: *Plant Molecular Biology: A Laboratory Manual*, Clark, Ed., Springer-Verlag, Berlin (1997); and, *Current Protocols in Molecular Biology*, Ausubel et al., Eds., Greene Publishing and Wiley-Interscience, New York (1995). cDNA synthesis kits are available from a variety of commercial vendors such as Stratagene or Pharmacia.

An exemplary method of constructing a greater than 95% pure full-length cDNA library is described by Carninci et al., *Genomics* 37:327–336 (1996). Other methods for producing full-length libraries are known in the art. See, e.g., Edery et al., *Mol. Cell Biol.* 15(6):3363–3371 (1995); and PCT Application WO 96/34981.

It is often convenient to normalize a cDNA library to create a library in which each clone is more equally represented. A number of approaches to normalize cDNA libraries are known in the art. Construction of normalized libraries is described in Ko, *Nucl. Acids. Res.* 18(19):5705–5711 (1990); Patanjali et al., *Proc. Natl. Acad. U.S.A.* 88:1943–1947 (1991); U.S. Pat. Nos. 5,482,685 and 5,637,685; and Soares et al., *Proc. Natl. Acad. Sci. USA* 91:9228–9232 (1994).

Subtracted cDNA libraries are another means to increase the proportion of less abundant cDNA species. See, Foote et al. in, *Plant Molecular Biology: A Laboratory Manual*, Clark, Ed., Springer-Verlag, Berlin (1997); Kho and Zarbl, *Technique* 3(2):58–63 (1991); Sive and St. John, *Nucl. Acids Res.* 16(22):10937 (1988); *Current Protocols in Molecular Biology*, Ausubel et al., Eds., Greene Publishing and Wiley-Interscience, New York (1995); and, Swaroop et al., *Nucl. Acids Res.* 19(8):1954 (1991). cDNA subtraction kits are commercially available. See, e.g., PCR-Select (Clontech).

To construct genomic libraries, large segments of genomic DNA are generated by random fragmentation. Examples of appropriate molecular biological techniques and instructions are found in Sambrook et al., *Molecular Cloning: A Laboratory Manual*, 2nd Ed., Cold Spring Harbor Laboratory, Vols. 1–3 (1989), Methods in Enzymology, Vol. 152: *Guide to Molecular Cloning Techniques*, Berger and Kimmel, Eds., San Diego: Academic Press, Inc. (1987),

*Current Protocols in Molecular Biology*, Ausubel et al., Eds., Greene Publishing and Wiley-Interscience, New York (1995); *Plant Molecular Biology: A Laboratory Manual*, Clark, Ed., Springer-Verlag, Berlin (1997). Kits for construction of genomic libraries are also commercially available.

The cDNA or genomic library can be screened using a probe based upon the sequence of a nucleic acid of the present invention such as those disclosed herein. Probes may be used to hybridize with genomic DNA or cDNA sequences to isolate homologous polynucleotides in the same or different plant species. Those of skill in the art will appreciate that various degrees of stringency of hybridization can be employed in the assay; and either the hybridization or the wash medium can be stringent. The degree of stringency can be controlled by temperature, ionic strength, pH and the presence of a partially denaturing solvent such as formamide.

Typically, stringent hybridization conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide.

Exemplary low stringency conditions include hybridization with a buffer solution of 30 to 35% formamide, 1 M NaCl, 1% SDS (sodium dodecyl sulfate) at 37° C., and a wash in 1× to 2×SSC (20×SSC=3.0 M NaCl/0.3 M trisodium citrate) at 50° C. Exemplary moderate stringency conditions include hybridization in 40 to 45% formamide, 1 M NaCl, 1% SDS at 37° C., and a wash in 0.5× to 1×SSC at 55° C. Exemplary high stringency conditions include hybridization in 50% formamide, 1 M NaCl, 1% SDS at 37° C., and a wash in 0.1×SSC at 60° C. Typically the time of hybridization is from 4 to 16 hours.

An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, New York (1993); and *Current Protocols in Molecular Biology*, Chapter 2, Ausubel et al., Eds., Greene Publishing and Wiley-Interscience, New York (1995). Often, cDNA libraries will be normalized to increase the representation of relatively rare cDNAs.

The nucleic acids of the invention can be amplified from nucleic acid samples using amplification techniques. For instance, polymerase chain reaction (PCR) technology can be used to amplify the sequences of polynucleotides of the present invention and related polynucleotides directly from genomic DNA or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes.

Examples of techniques useful for in vitro amplification methods are found in Berger, Sambrook, and Ausubel, as well as Mullis et al., U.S. Pat. No. 4,683,202 (1987); and, *PCR Protocols A Guide to Methods and Applications*, Innis et al., Eds., Academic Press Inc., San Diego, Calif. (1990). Commercially available kits for genomic PCR amplification are known in the art. See, e.g., Advantage-GC Genomic PCR Kit (Clontech). The T4 gene 32 protein (Boehringer Mannheim) can be used to improve yield of long PCR products. PCR-based screening methods have also been described. Wilfinger et al. describe a PCR-based method in which the longest cDNA is identified in the first step so that incomplete clones can be eliminated from study. *BioTechniques* 22(3): 481–486 (1997).

In one aspect of the invention, nucleic acids can be amplified from a plant nucleic acid library. The nucleic acid library may be a cDNA library, a genomic library, or a library generally constructed from nuclear transcripts at any stage of intron processing. Libraries can be made from a variety of plant tissues. Good results have been obtained using mitotically active tissues such as shoot meristems, shoot meristem cultures, embryos, callus and suspension cultures, immature ears and tassels, and young seedlings. The cDNAs of the present invention were obtained from immature zygotic embryo and regenerating callus libraries.

Alternatively, the sequences of the invention can be used to isolate corresponding sequences in other organisms, particularly other plants, more particularly, other monocots. In this manner, methods such as PCR, hybridization, and the like can be used to identify such sequences having substantial sequence similarity to the sequences of the invention. See, for example, Sambrook et al. (1989) *Molecular Cloning: A Laboratory Manual* (2d ed., Cold Spring Harbor Laboratory Press, Plainview, N.Y.). and Innis et al. (1990), *PCR Protocols: A Guide to Methods and Applications* (Academic Press, New York). Coding sequences isolated based on their sequence identity to the entire inventive coding sequences set forth herein or to fragments thereof are encompassed by the present invention.

The isolated nucleic acids of the present invention can also be prepared by direct chemical synthesis by methods such as the phosphotriester method of Narang et al., *Meth. Enzymol.* 68:90–99 (1979); the phosphodiester method of Brown et al., *Meth. Enzymol.* 68:109–151 (1979); the diethylphosphoramidite method of Beaucage et al., *Tetra. Lett* 22:1859–1862 (1981); the solid phase phosphoramidite triester method described by Beaucage and Caruthers, *Tetra. Letts.* 22(20):1859–1862 (1981), e.g., using an automated synthesizer, e.g., as described in Needham-VanDevanter et al., *Nucleic Acids Res.* 12:6159–6168 (1984); and, the solid support method of U.S. Pat. No. 4,458,066. Chemical synthesis generally produces a single stranded oligonucleotide. This may be converted into double stranded DNA by hybridization with a complementary sequence, or by polymerization with a DNA polymerase using the single strand as a template. One of skill will recognize that while chemical synthesis of DNA is limited to sequences of about 100 bases, longer sequences may be obtained by the ligation of shorter sequences.

Expression Cassettes

In another embodiment expression cassettes comprising isolated nucleic acids of the present invention are provided. An expression cassette will typically comprise a polynucleotide of the present invention operably linked to transcriptional initiation regulatory sequences which will direct the transcription of the polynucleotide in the intended host cell, such as tissues of a transformed plant.

The construction of such expression cassettes which can be employed in conjunction with the present invention is well known to those of skill in the art in light of the present disclosure. See, e.g., Sambrook et al.; *Molecular Cloning: A Laboratory Manual*; Cold Spring Harbor, N.Y.; (1989); Gelvin et al.; *Plant Molecular Biology Manual* (1990); *Plant Biotechnology: Commercial Prospects and Problems*, eds.

Prakash et al.; Oxford & IBH Publishing Co.; New Delhi, India; (1993); and Heslot et al.; *Molecular Biology and Genetic Engineering of Yeasts*; CRC Press, Inc., USA; (1992); each incorporated herein in its entirety by reference.

For example, plant expression vectors may include (1) a cloned plant gene under the transcriptional control of 5' and 3' regulatory sequences and (2) a dominant selectable marker. Such plant expression vectors may also contain, if desired, a promoter regulatory region (e.g., one conferring inducible, constitutive, environmentally- or developmentally-regulated, or cell- or tissue-specific/selective expression), a transcription initiation start site, a ribosome binding site, an RNA processing signal, a transcription termination site, and/or a polyadenylation signal.

Constitutive, tissue-preferred or inducible promoters can be employed. Examples of constitutive promoters include the cauliflower mosaic virus (CaMV) 35S transcription initiation region, the 1'- or 2'-promoter derived from T-DNA of *Agrobacterium tumefaciens*, the actin promoter, the ubiquitin promoter, the histone H2B promoter (Nakayama et al., 1992, FEBS Left 30:167–170), the Smas promoter, the cinnamyl alcohol dehydrogenase promoter (U.S. Pat. No. 5,683,439), the Nos promoter, the pEmu promoter, the rubisco promoter, the GRP1-8 promoter, and other transcription initiation regions from various plant genes known in the art.

Examples of inducible promoters are the Adh1 promoter which is inducible by hypoxia or cold stress, the Hsp70 promoter which is inducible by heat stress, the PPDK promoter which is inducible by light, the In2 promoter which is safener induced, the ERE promoter which is estrogen induced and the Pepcarboxylase promoter which is light induced.

Examples of promoters under developmental control include promoters that initiate transcription preferentially in certain tissues, such as leaves, roots, fruit, seeds, or flowers. An exemplary promoter is the anther specific promoter 5126 (U.S. Pat. Nos. 5,689,049 and 5,689,051). Examples of seed-preferred promoters include, but are not limited to, 27 kD gamma zein promoter and waxy promoter, Boronat, A., Martinez, M. C., Reina, M., Puigdomenech, P. and Palau, J.; Isolation and sequencing of a 28 kD glutelin-2 gene from maize: Common elements in the 5' flanking regions among zein and glutelin genes; *Plant Sci.* 47:95–102 (1986) and Reina, M., Ponte, I., Guillen, P., Boronat, A. and Palau, J., Sequence analysis of a genomic clone encoding a Zc2 protein from *Zea mays* W64 A, *Nucleic Acids Res.* 18(21): 6426 (1990). See the following site relating to the waxy promoter: Kloesgen, R. B., Gierl, A., Schwarz-Sommer, Z. S. and Saedler, H., Molecular analysis of the waxy locus of *Zea mays*, *Mol. Gen. Genet.* 203:237–244 (1986). The disclosures of each of these are incorporated herein by reference in their entirety.

The barley or maize Nuc1 promoter, the maize Cim 1 promoter or the maize LTP2 promoter can be used to preferentially express in the nucellus. See for example WO00/11177 and U.S. Pat. No. 6,225,529, issued May 1, 2001, the disclosures of which are incorporated herein by reference.

Either heterologous or non-heterologous (i.e., endogenous) promoters can be employed to direct expression of the nucleic acids of the present invention. These promoters can also be used, for example, in expression cassettes to drive expression of antisense nucleic acids to reduce, increase, or alter concentration and/or composition of the proteins of the present invention in a desired tissue.

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added can be derived from, for example, the nopaline synthase or octopine synthase genes, or alternatively from another plant gene, or less preferably from any other eukaryotic gene.

An intron sequence can be added to the 5' untranslated region or the coding sequence of the partial coding sequence to increase the amount of the mature message that accumulates. See for example Buchman and Berg, *Mol. Cell Biol.* 8:4395–4405 (1988); Callis et al., *Genes Dev.* 1:1183–1200 (1987). Use of maize introns Adh1-S intron 1, 2, and 6, the Bronze-1 intron are known in the art. See generally, *The Maize Handbook*, Chapter 116, Freeling and Walbot, Eds., Springer, New York (1994).

The vector comprising the sequences from a polynucleotide of the present invention will typically comprise a marker gene which confers a selectable phenotype on plant cells. Usually, the selectable marker gene will encode antibiotic or herbicide resistance. Suitable genes include those coding for resistance to the antibiotics spectinomycin and streptomycin (e.g., the aada gene), the streptomycin phosphotransferase (SPT) gene coding for streptomycin resistance, the neomycin phosphotransferase (NPTII) gene encoding kanamycin or geneticin resistance, the hygromycin phosphotransferase (HPT) gene coding for hygromycin resistance.

Suitable genes coding for resistance to herbicides include those which act to inhibit the action of acetolactate synthase (ALS), in particular the sulfonylurea-type herbicides (e.g., the acetolactate synthase (ALS) gene containing mutations leading to such resistance in particular the S4 and/or Hra mutations), those which act to inhibit action of glutamine synthase, such as phosphinothricin or basta (e.g., the bar gene), or other such genes known in the art. The bar gene encodes resistance to the herbicide basta and the ALS gene encodes resistance to the herbicide chlorsulfuron.

While useful in conjunction with the above antibiotic and herbicide-resistance selective markers (i.e. use of the BI gene can increase transformation frequencies when using chemical selection), use of the BI gene confers a growth advantage to transformed cells without the need for inhibitory compounds to retard non-transformed growth. Thus, BI transformants are recovered based solely on their differential growth advantage.

Typical vectors useful for expression of genes in higher plants are well known in the art and include vectors derived from the tumor-inducing (Ti) plasmid of *Agrobacterium tumefaciens* described by Rogers et al., *Meth. In Enzymol.* 153:253–277 (1987). Exemplary *A. tumefaciens* vectors useful herein are plasmids pKYLX6 and pKYLX7 of Schardl et al., *Gene* 61:1–11 (1987) and Berger et al., *Proc. Natl. Acad. Sci. USA* 86:8402–8406 (1989). Another useful vector herein is plasmid pBI101.2 that is available from Clontech Laboratories, Inc. (Palo Alto, Calif.).

A variety of plant viruses that can be employed as vectors are known in the art and include cauliflower mosaic virus (CaMV), geminivirus, brome mosaic virus, and tobacco mosaic virus.

A polynucleotide of the present invention can be expressed in either sense or anti-sense orientation as desired. In plant cells, it has been shown that antisense RNA inhibits gene expression by preventing the accumulation of mRNA which encodes the enzyme of interest, see, e.g., Sheehy et al., *Proc. Natl. Acad. Sci. USA* 85:8805–8809 (1988); and Hiatt et al., U.S. Pat. No. 4,801,340.

Another method of suppression is sense suppression. Introduction of nucleic acid configured in the sense orientation has been shown to be an effective means by which to block the transcription of target genes. For an example of the use of this method to modulate expression of endogenous genes see, Napoli et al., *The Plant Cell* 2:279–289 (1990) and U.S. Pat. No. 5,034,323. Recent work has shown suppression with the use of double stranded RNA. Such work is described in Tabara et al., *Science* 282:5388:430–431 (1998). Hairpin approaches of gene suppression are disclosed in WO 98/53083 and WO 99/53050.

Catalytic RNA molecules or ribozymes can also be used to inhibit expression of plant genes. The inclusion of ribozyme sequences within antisense RNAs confers RNA-cleaving activity upon them, thereby increasing the activity of the constructs. The design and use of target RNA-specific ribozymes is described in Haseloff et al., *Nature* 334: 585–591 (1988).

A variety of cross-linking agents, alkylating agents and radical generating species as pendant groups on polynucleotides of the present invention can be used to bind, label, detect, and/or cleave nucleic acids. For example, Vlassov, V. V., et al., *Nucleic Acids Res* (1986) 14:4065–4076, describe covalent bonding of a single-stranded DNA fragment with alkylating derivatives of nucleotides complementary to target sequences. A report of similar work by the same group is that by Knorre, D. G., et al., *Biochimie* (1985) 67:785–789. Iverson and Dervan also showed sequence-specific cleavage of single-stranded DNA mediated by incorporation of a modified nucleotide which was capable of activating cleavage (*J. Am. Chem. Soc.* (1987) 109:1241–1243). Meyer, R. B., et al., *J. Am. Chem. Soc.* (1989) 111:8517–8519, effect covalent crosslinking to a target nucleotide using an alkylating agent complementary to the single-stranded target nucleotide sequence. A photo-activated crosslinking to single-stranded oligonucleotides mediated by psoralen was disclosed by Lee, B. L., et al., *Biochemistry* (1988) 27:3197–3203. Use of crosslinking in triple-helix forming probes was also disclosed by Home et al., *J. Am. Chem. Soc.* (1990) 112:2435–2437. Use of N4, N4-ethanocytosine as an alkylating agent to crosslink to single-stranded oligonucleotides has also been described by Webb and Matteucci, *J. Am. Chem. Soc.* (1986) 108:2764–2765; *Nucleic Acids Res* (1986) 14:7661–7674; Feteritz et al., *J. Am. Chem. Soc.* 113:4000 (1991). Various compounds to bind, detect, label, and/or cleave nucleic acids are known in the art. See, for example, U.S. Pat. Nos. 5,543,507; 5,672,593; 5,484,908; 5,256,648; and, 5,681941.

Proteins

Proteins of the present invention include proteins having the disclosed sequences as well as proteins coded by the disclosed polynucleotides. In addition proteins of the present invention include proteins derived from the native protein by deletion (so-called truncation), addition or substitution of one or more amino acids at one or more sites in the native protein. Such variants may result from, for example, genetic polymorphism or from human manipulation. Methods for such manipulations are generally known in the art.

For example, amino acid sequence variants of the polypeptide can be prepared by mutations in the cloned DNA sequence encoding the native protein of interest. Methods for mutagenesis and nucleotide sequence alterations are well known in the art. See, for example, Walker and Gaastra, eds. (1983) *Techniques in Molecular Biology* (MacMillan Publishing Company, New York); Kunkel (1985) *Proc. Natl. Acad. Sci. USA* 82:488–492; Kunkel et al. (1987) *Methods Enzymol.* 154:367–382; Sambrook et al. (1989) *Molecular Cloning: A Laboratory Manual* (Cold Spring Harbor, N.Y.); U.S. Pat. No. 4,873,192; and the references cited therein; herein incorporated by reference. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be preferred.

In constructing variants of the proteins of interest, modifications to the nucleotide sequences encoding the variants will generally be made such that variants continue to possess the desired activity.

The *Zea mays* Bax inhibitor proteins of the instant invention are aligned below (see Table 4). The seven genes appear to be divided into two groups; BI-1, -2, -3 and -4 and BI-5, -6 and -7. Areas of homology are indicated and a consensus sequence is also shown.

The *Glycine max* Bax inhibitor proteins of the instant invention are aligned below (see Table 5). The ten genes appear to be divided into several groups; one of Gm-BI-1 and -5; Gm-BI-2 and -3; and another containing closely related Gm-BI-6, -9, -7 and -8. Gm-BI-4 and and Gm-BI-10 appear to be in between the -1, 2, 3, 5 and -6, 9, 7, 8 groupings. Areas of homology are indicated and a consensus sequence is also shown.

TABLE 4

Protein alignment of Maize Bax Inhibitor genes

```
                                    1                                                50
(SeqIDNo2)  BI-1    (1)  --------------MESLFG--------QSQRRRAGGSGFESLKRLG--
(SeqIDNo32) BI-2    (1)  --------------MDAFFS----ASSASAPYGYGAGGWSYDSLKNFR--
(SeqIDNo34) BI-3    (1)  --------------MDAFYSTTASSSTSSAPYGGGGEGWGYDSMKNFR--
(SeqIDNo8)  BI-4    (1)  --------------------------------------------------
(SeqIDNo10) BI-5    (1)  -----------MFGYRKADP----------DLEAGGSSLLYPGMTESPE-
(SeqIDNo12) BI-6    (1)  MASVAEMQPLAPAGYRRAPEMKEKVEASVVDLEAGTGETLYPGISRGESA
(SeqIDNo14) BI-7    (1)  -----------MFGYQKGLDVEAGTSG---AAATGGARQLYPGMQESPE-
Consensus           (1)                               GGG    Y    M 51                                               100
            BI-1    (27)  ---HISPAVQSHLKHVYLTLCSALAFSALGAYLH---ILLNVGGALTTVG
            BI-2    (31)  ---QITPAVQTHLKLVYLTLCAALASSAVGAYLH---VVWNIGGTLTMLG
```

TABLE 4-continued

Protein alignment of Maize Bax Inhibitor genes

```
            BI-3    (35)  ---QISPAVQTHLKLVYLTLCVALASSAVGAYLH---VVWNIGGMLTMLG
            BI-4     (1)  --------------------------------------------------
            BI-5    (29)  LRWAFVRKIYVILAVQLAMTAAVSAFVVKVPAVSNFFVFSNAGVALYIFL
            BI-6    (51)  LRWGFVRKVYGILAAQLLLTTAVSALTVLHPTLN---ATLSDSPGLALVL
            BI-7    (36)  LRWALIRKIYVILSLQLLLTAVVAAVVVKVRAIPHFFTTTSAGLGLYIFL
Consensus           (51)      I   V   LL  L   A   ASL    L    V  NG AL IL 101                                              150
            BI-1    (71)  CVASIAFLISLPASRDQERNRLALLMSAALLQGASVGPLVDLVIDLDSRI
            BI-2    (75)  CVGSIAWLFSVPVYEE--RKRYGLLMAAALLEGASVGPLVKLAVEFDPSI
            BI-3    (79)  CVGSIAWLFSVPVYEE--RKRYWLLMAAALLEGASVGPLIKLAVEFDPSI
            BI-4     (1)  --------------------------------------MTNGCFFSLSI
            BI-5    (79)  IILPFLVLCPLRYYHQKHPVNLLLLGLFTVAISFAVG---MTCAFTSGKI
            BI-6    (98)  AVLPFILMIPLYHYQHKHPHNFVFLGLFTLCLSFSIG---VAC-ANTQGKI
            BI-7    (86)  IILPFIVLCPLYFHEKHPVNLILLGLFTVAISFAVG---MTCAFTSGKV
Consensus          (101)   V      L   LYE       LL   L     SVG  V         KI 151                                              200
            BI-1   (121)  LVTAFVGTAVAFACFSGAAIIAKRR--EYLYLGGLLSSGLSILLWLQFAT
            BI-2   (123)  LVTAFVGTAIAFACFTGAAMVARRR--EYLYLGGLLSSGLSILLWLQLAG
            BI-3   (127)  LVTAFVGTAIAFACFSCAAMVAKRR--EYLYLGGLLSSGLSILLWLQFAA
            BI-4    (12)  LVTAFVGTAIAFACFTGAAMVARRR--EYLYLGGLLSSGLSILLWLQLAG
            BI-5   (126)  ILEAAILTAVVVISLTAYTFWAAKRGHDFNFLGPFLFAAIMVLMVFSLIQ
            BI-6   (145)  VLEALVLTAGVVVSLTAYAFWASKKGKEFGYLGPILSSALTILVLTSFLQ
            BI-7   (133)  ILESAILTTVVVLSLTAYTFWAVNRGKDFSFLGPFLFAAIIVLLVFALIQ
Consensus          (151)  LVTAFVGTAIAFACFTAAAMVAKRR--EYLYLGGLLSSGLSILLWLQLA 201                                              250
            BI-1   (169)  SIFGHTSAT-FMFELYFGLLVFLGYMVFDTQEIIERAHRGDMDYIKHALT
            BI-2   (171)  SIFGHSATS-FMFEVYFGLLIFLGYVVYDTQEIIERAHRGDMDHVKHALT
            BI-3   (175)  SIFGHQSTSSFMFEVYFGLLIFLGYMVYDTQEVIERAHHGDMDYIKHALT
            BI-4    (60)  SIFGHSATS-FMFEVYFGLLIFLGYVVYDTQEIIERAHRGDMDHVKHALT
            BI-5   (176)  IFFPLGKIS-VMIYGGLASLIFCGYIIYDTDNVIKRYTY--DEYIWAAVS
            BI-6   (195)  VFFPLGPVS-VGLFGGLGALVFSGFILYDTENLIKRHTY--DEYIWASVG
            BI-7   (183)  ILFPLGKLS-QMIYGGLASLIFSGYIVYDTNNIIKRYTY--DQYVWAAVS
Consensus          (201)  SIFGH A S  FMFEVYFGLLIFLGYIVYDTQEIIERAHYGDMDYIKHALT 251                                              300
            BI-1   (218)  LFTDFVAVLVRILVIMMKNAQEKSQDEKKRKKR-----------------
            BI-2   (220)  LFTDFVAVLVRVLVIMLKNGADKSEDKKRKKRS-----------------
            BI-3   (225)  LFTDFVAVLVRILVIMLKNAADKSEDKRRKRRSW----------------
            BI-4   (109)  LFTDFVAVLVRVLVIMLKNGADKSEDKKRKKRS-----------------
            BI-5   (223)  LYLDVINLFLSLLQLLRAADS-----------------------------
            BI-6   (242)  LYLDILNLFLSILNMLRSMQSDN---------------------------
            BI-7   (230)  LYLDVINLFLSLMTLFRAAD------------------------------
Consensus          (251)  LFTDFVAVLVRILVIMLK  ADKSEDKKRKKRS
                           301        311
```

TABLE 5

Protein alignment of Glycine max Bax Inhibitor genes

```
                                         1                                          50
(SeqIDno16)      Gm-BI1-1    (1)  ---ARAFNSFFDSRNRWNYDTLKNFRQISPVVQNHLKQVYFTLCFAVVAA
(SeqIDno18)      Gm-BI1-2    (1)  MDTFFNSQSSSSSRSRWSYDTLKNFREISPLVQNHIKRVYFTLCCAVVAA
(SeqIDno20)      Gm-BI1-3    (1)  --------------------------------------------------
(trnslofSeqIDno21) Gm-BI1-4  (1)  --------------------------------------------------
(trnslofSeqIDno22) Gm-BI1-5  (1)  --------------------------------------------------
(trnslofSeqIDno23) Gm-BI1-6  (1)  ---------MFEPQQLYTRAKTEEFDLESG-------ETLYPGLSVGENQ
(SeqIDno25)      Gm-BI1-7    (1)  ----------------MWNQPFGKTDLESG------SRPLYPMMLESP-E
(SeqIDno27)      Gm-BI1-8    (1)  ----------------MWNQPLGKTDLESG------SRPLYPMMLESP-E
(SeqIDno29)      Gm-BI1-9    (1)  ---------MFEPQQLYTRAKTEEFDLESG-------ETLYPGLSVGENQ
(trnslofSeqIDno30) Gm-1-10   (1)  -----------------------KXDVESGGDGNANPRPLYPAMLEXP-Q
Consensus                    (1)                          DLESG         LYP M 51                                         100
                 Gm-BI1-1   (48)  AVGAYLHVLLNIGGFLTTVACMGSSFWLLSTPPFEERKRVT-----LLMA
                 Gm-BI1-2   (51)  AVGAFLHVLWNIGGFLTTLASIGSMVWLLSTPPVEEQKRLS-----LLMA
                 Gm-BI1-3    (1)  --------------------------------------------------
                 Gm-BI1-4    (1)  --------------------------------------------------
                 Gm-BI1-5    (1)  ----------------TTVACVGSSVWLLSTPPFEERKRVT-----LLMA
                 Gm-BI1-6   (35)  LRWGFIRKVYGILSAQIVLTTLVSVTTVFYTPINDLLKGNS----TLLLI
                 Gm-BI1-7   (28)  LRWSFIRKVYSIIAIQLLVTIVVGAVVVTVRPISVFFATTG-AGLALYIV
                 Gm-BI1-8   (28)  LRWSFIRKVYSIIAIQLLVTIVVGAVVVTVRPISVFFATTG-AGLALYIV
```

TABLE 5-continued

Protein alignment of Glycine max Bax Inhibitor genes

```
            Gm-BI1-9   (35)  LRWGFIRKVYGILSAQIVLTTLVSVTTVFYTPINDLLKGNS----TLLLI
            Gm-BI1-10  (27)  LRWAFIRKXYTILTIQLLLTIAVASVVRLRSAPSLFSSVSSPGGLALYIV
Consensus              (51)  LRWAFIRKVY IL  QLLLT VVSSV V  TP  E  K  S    LLIV 101                                              150
            Gm-BI1-1   (93)  ASLFQGSSIGPLIDLAIHIDPSLIFSAFVGTALAFACFS-----------
            Gm-BI1-2   (96)  SALFQGASIGPLIDLAIAIDPSLIVSAFVATSLAFACFS-----------
            Gm-BI1-3   (1)   --------------------------------------------------
            Gm-BI1-4   (1)   --------------------------------------------------
            Gm-BI1-5   (30)  ASLFQGASIGPLIDLAIQIDPSLIFSAFVGTSLAFACFS-----------
            Gm-BI1-6   (81)  LLFLPFIFLIPLLKYQQKHPHNYILLALFTVSISSTVRSQLAPTPTGKLC
            Gm-BI1-7   (77)  LIFVPFITLCPLYYYSQKHPVNYLLLGVFTVSLGFVVG------------
            Gm-BI1-8   (77)  LIFVPFITLCPLYYYSQKHPVNYLLLAVFTVSLGFVVG------------
            Gm-BI1-9   (81)  LLFLPFIFLIPLLKYQQKHPHNYILLALFTVSISSTIG------------
            Gm-BI1-10  (77)  LLXAPLILVCPLYYYHQETPLNYILLFXFTVTLAXA--------------
Consensus              (101) LL  P ISL PLI YAQ  P NYILLA FTVSLAF 151                                              200
            Gm-BI1-1   (132) ---------------------------GAALVARRREYLYLGGLVSSGL
            Gm-BI1-2   (135) ---------------------------AAALVARRREYLYLGGLLSSGL
            Gm-BI1-3   (1)   --------------------------------------------------
            Gm-BI1-4   (1)   --------------------------------------------------
            Gm-BI1-5   (69)  ---------------------------GAALVARRREYLYLGGLVSSGL
            Gm-BI1-6   (131) LTCANTDGKIVLEALILTSAVVSSLTGYAFWASKKGKDFSFLGPXLFTSL
            Gm-BI1-7   (115) LSCAFTSEKVILEAVILTAVVVIGLTLYTFWAARRGHDFNFLGPFLFGAV
            Gm-BI1-8   (115) LSCAFTSEKVILEAVILTAVVVIALTLYTFWAARRGHDFNFLGPFLFGAV
            Gm-BI1-9   (119) VTCANTDGKIVLEALILTSAVVSSLTGYAFWASKKGKDFSFLGPILFTSL
            Gm-BI1-10  (113) --------------------------------------------------
Consensus              (151)                            A    R RDF FLG   L SGL 201                                              250
            Gm-BI1-1   (154) SILLWLHFASSIFGGSTALFKFELYFGLLVFVGYIVVDTQEIVERAHLGD
            Gm-BI1-2   (157) SILMWLHFASSLFGGSIALFKFELYFGLLVFVGYVFVDTQEIIERAHFGD
            Gm-BI1-3   (1)   -------------GGSIALFKFELYFGLLVFVGYIVVDTQEIIERAHFGD
            Gm-BI1-4   (1)   ----------NISSGGTYLQFLQLYFGLLVFVGYIVVDTQEIIERAHFGD
            Gm-BI1-5   (91)  SILLWLHFASSIFGGSTALFKFELYFGLLVFVGYIVVDTQEIVEXAHLGD
            Gm-BI1-6   (181) FTLILTGMMQMFFPLGPTAHAIYGAIGAMIFSGYIVYDTDNLIKRFTY--
            Gm-BI1-7   (165) LVLMVFALIQVLFPLGKLSVMIYGCLAAIIFCGYIIYDTDNLIKRYSY--
            Gm-BI1-8   (165) LVLMVFALIQVLFPLGKLSVMIYGCLAAIIFCGYIIYDTDNLIKRYSY--
            Gm-BI1-9   (169) ITLILTGMMQMFFPLGPTAHAIYGAIGAMIFSGYIVYDTDNLIKRFTY--
            Gm-BI1-10  (113)
Consensus              (201)    ILM      IF GG  L  I LYFGLLVFVGYIIVDTQEIIERAHYGD 251                                              300
            Gm-BI1-1   (204) LDYVKHALTLFTDLVAVFVRILVIMLKNSTE-------------------
            Gm-BI1-2   (207) LDYVKHALTLFTDLAAIFVRILIIMLKNSFG-------------------
            Gm-BI1-3   (38)  LDYVKHALTLFTDLAAIFVRILIIMLK-----------------------
            Gm-BI1-4   (41)  LDYVKHALTLFTDLAAIFVRILIIMVSWTSSYWCSFFFVSSR-IGIHKVL
            Gm-BI1-5   (141) LDYVKHALTLFTDLXAI---------------------------------
            Gm-BI1-6   (229) DEYIGASVTLYLDILNLFLSILRILREA----------------------
            Gm-BI1-7   (213) DEYIWASISLYLDIINLFLSLLTIFRAADS--------------------
            Gm-BI1-8   (213) DEYIWASISLYLDIINLFLSLLTIFRAADS--------------------
            Gm-BI1-9   (217) DEYIGASVTLYLDILNLFLSILRILREANN--------------------
            Gm-BI1-10  (113) --------------------------------------------------
Consensus              (251) LDYVKHALTLFTDLIAIFL IL IM 301                       334
            Gm-BI1-1   (235) ----------RNEKKKKRRD--------------
            Gm-BI1-2   (238) ----------GNGKKKKRGGLLADRPTRAQASLP
            Gm-BI1-3   (65)  -------NSSERNEKKKKRRD-------------
            Gm-BI1-4   (90)  ILSQLKNSSERNEKKKKRRD--------------
            Gm-BI1-5   (158) ----------------------------------
            Gm-BI1-6   (257) ----------------------------------
            Gm-BI1-7   (243) ----------------------------------
            Gm-BI1-8   (243) ----------------------------------
            Gm-BI1-9   (247) ----------------------------------
            Gm-BI1-10  (113) ----------------------------------
Consensus              (301)
```

The consensus sequence of each of the *Zea mays* and *Glycine max* BI polypeptide describes polypeptides of the invention and illustrates more conserved amino acid residues of the genus.

The isolated proteins of the present invention include a polypeptide comprising at least 30 contiguous amino acids encoded by any one of the nucleic acids of the present invention, or polypeptides that are conservatively modified variants thereof. The proteins of the present invention or variants thereof can comprise any number of contiguous amino acid residues from a polypeptide of the present invention, wherein that number is selected from the group of integers consisting of from 30 to the number of residues in a full-length polypeptide of the present invention. Optionally, this subsequence of contiguous amino acids is at least 30, 35, 40, 45, 50, 55, 60, 65, 70, 75, 80, 85, 90, 95, 100, 105, 110, 120, 125, 130, 135, 140, 145, 150, 160, 170, 180, 190, 200, 220, 240, 250, 270, 290, 300, 320, 340, 350, 370, 390, 400, 420, 440, 450, 470, 490 or 500 amino acids in length.

The present invention includes catalytically active polypeptides (i.e., enzymes). Catalytically active polypeptides will generally have a specific activity of at least about 20%, 30%, 40%, 50%, 60%, 70%, 80%, 90%, or 95% that of the native (non-synthetic), endogenous polypeptide. Further, the substrate specificity ($k_{cat}/K_m$) is optionally substantially similar to the native (non-synthetic), endogenous polypeptide. Typically, the $K_m$ will be at least about 30%, 40%, 50%, 60%, 70%, 80%, 90%, or 95% that of the native (non-synthetic), endogenous polypeptide. Methods of assaying and quantifying measures of enzymatic activity and substrate specificity ($k_{cat}/K_m$), are well known to those of skill in the art.

The present invention includes modifications that can be made to an inventive protein. In particular, it may be desirable to diminish the activity of the gene. Other modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

Using the nucleic acids of the present invention, one may express a protein of the present invention in recombinantly engineered cells such as bacteria, yeast, insect, mammalian, or plant cells. The cells produce the protein in a non-natural condition (e.g., in quantity, composition, location, and/or time), because they have been genetically altered through human intervention to do so.

Typically, an intermediate host cell will be used in the practice of this invention to increase the copy number of the cloning vector. With an increased copy number, the vector containing the gene of interest can be isolated in significant quantities for introduction into the desired plant cells.

Host cells that can be used in the practice of this invention include prokaryotes and eukaryotes. Prokaryotes include bacterial hosts such as *Eschericia coli*, *Salmonella typhimurium*, and *Serratia marcescens*. Eukaryotic hosts such as yeast or filamentous fungi may also be used in this invention. Since these hosts are also microorganisms, it will be essential to ensure that plant promoters which do not cause expression of the polypeptide in bacteria are used in the vector.

Commonly used prokaryotic control sequences include such commonly used promoters as the beta lactamase (penicillinase) and lactose (lac) promoter systems (Chang et al., *Nature* 198:1056 (1977)), the tryptophan (trp) promoter system (Goeddel et al., *Nucleic Acids Res.* 8:4057 (1980)) and the lambda derived P L promoter and N-gene ribosome binding site (Shimatake et al., *Nature* 292:128 (1981)). The inclusion of selection markers in DNA vectors transfected in *E. coli* is also useful. Examples of such markers include genes specifying resistance to ampicillin, tetracycline, or chloramphenicol.

The vector is selected to allow introduction into the appropriate host cell. Bacterial vectors are typically of plasmid or phage origin. Expression systems for expressing a protein of the present invention are available using *Bacillus* sp. and *Salmonella* (Palva et al., *Gene* 22:229–235 (1983); Mosbach et al., *Nature* 302:543–545 (1983)).

Synthesis of heterologous proteins in yeast is well known. See Sherman, F., et al., *Methods in Yeast Genetics*, Cold Spring Harbor Laboratory (1982). Two widely utilized yeast for production of eukaryotic proteins are *Saccharomyces cerevisiae* and *Pichia pastoris*. Vectors, strains, and protocols for expression in *Saccharomyces* and *Pichia* are known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like as desired.

A protein of the present invention, once expressed, can be isolated from yeast by lysing the cells and applying standard protein isolation techniques to the lysates. The monitoring of the purification process can be accomplished by using Western blot techniques or radioimmunoassay of other standard immunoassay techniques.

The proteins of the present invention can also be constructed using non-cellular synthetic methods. Solid phase synthesis of proteins of less than about 50 amino acids in length may be accomplished by attaching the C-terminal amino acid of the sequence to an insoluble support followed by sequential addition of the remaining amino acids in the sequence. Techniques for solid phase synthesis are described by Barany and Merrifield, Solid-Phase Peptide Synthesis, pp. 3–284 in *The Peptides: Analysis, Synthesis, Biology. Vol. 2: Special Methods in Peptide Synthesis, Part A.*; Merrifield et al., *J. Am. Chem. Soc.* 85:2149–2156 (1963), and Stewart et al., *Solid Phase Peptide Synthesis*, 2nd ed., Pierce Chem. Co., Rockford, Ill. (1984). Proteins of greater length may be synthesized by condensation of the amino and carboxy termini of shorter fragments. Methods of forming peptide bonds by activation of a carboxy terminal end (e.g., by the use of the coupling reagent N,N'-dicycylohexylcarbodiimide)) is known to those of skill.

The proteins of this invention, recombinant or synthetic, may be purified to substantial purity by standard techniques well known in the art, including detergent solubilization, selective precipitation with such substances as ammonium sulfate, column chromatography, immunopurification methods, and others. See, for instance, R. Scopes, *Protein Purification: Principles and Practice*, Springer-Verlag: New York (1982); Deutscher, *Guide to Protein Purification*, Academic Press (1990). For example, antibodies may be raised to the proteins as described herein. Purification from *E. coli* can be achieved following procedures described in U.S. Pat. No. 4,511,503. Detection of the expressed protein is achieved by methods known in the art and include, for example, radioimmunoassays, Western blotting techniques or immunoprecipitation.

The present invention further provides a method for modulating (i.e., increasing or decreasing) the concentration or composition of the polypeptides of the present invention in a plant or part thereof. Modulation can be effected by increasing or decreasing the concentration and/or the composition (i.e., the ratio of the polypeptides of the present invention) in a plant.

The method comprises transforming a plant cell with an expression cassette comprising a polynucleotide of the present invention to obtain a transformed plant cell, growing the transformed plant cell under conditions allowing expression of the polynucleotide in the plant cell in an amount sufficient to modulate concentration and/or composition in the plant cell.

In some embodiments, the content and/or composition of polypeptides of the present invention in a plant may be modulated by altering, in vivo or in vitro, the promoter of a non-isolated gene of the present invention to up- or down-regulate gene expression. In some embodiments, the coding regions of native genes of the present invention can be altered via substitution, addition, insertion, or deletion to decrease activity of the encoded enzyme. See, e.g., Kmiec, U.S. Pat. No. 5,565,350; Zarling et al., PCT/US93/03868. One method of down-regulation of the protein involves using PEST sequences that provide a target for degradation of the protein.

In some embodiments, an isolated nucleic acid (e.g., a vector) comprising a promoter sequence is transfected into a plant cell. Subsequently, a plant cell comprising the promoter operably linked to a polynucleotide of the present invention is selected for by means known to those of skill in the art such as, but not limited to, Southern blot, DNA sequencing, or PCR analysis using primers specific to the promoter and to the gene and detecting amplicons produced therefrom. A plant or plant part altered or modified by the foregoing embodiments is grown under plant forming conditions for a time sufficient to modulate the concentration and/or composition of polypeptides of the present invention in the plant. Plant forming conditions are well known in the art.

In general, content of the polypeptide is increased or decreased by at least 5%, 10%, 20%, 30%, 40%, 50%, 60%, 70%, 80%, or 90% relative to a native control plant, plant part, or cell lacking the aforementioned expression cassette. Modulation in the present invention may occur during and/or subsequent to growth of the plant to the desired stage of development. Modulating nucleic acid expression temporally and/or in particular tissues can be controlled by employing the appropriate promoter operably linked to a polynucleotide of the present invention in, for example, sense or antisense orientation as discussed in greater detail, supra. Induction of expression of a polynucleotide of the present invention can also be controlled by exogenous administration of an effective amount of inducing compound. Inducible promoters and inducing compounds which activate expression from these promoters are well known in the art. In another embodiment, the polypeptides of the present invention are modulated in monocots or dicots, preferably maize, soybeans, sunflower, sorghum, canola, wheat, alfalfa, rice, barley and millet.

Means of detecting the proteins of the present invention are not critical aspects of the present invention. In another embodiment, the proteins are detected and/or quantified using any of a number of well recognized immunological binding assays (see, e.g., U.S. Pat. Nos. 4,366,241; 4,376,110; 4,517,288; and 4,837,168). For a review of the general immunoassays, see also Methods in Cell Biology, Vol. 37: *Antibodies in Cell Biology*, Asai, Ed., Academic Press, Inc. New York (1993); *Basic and Clinical Immunology* 7th Edition, Stites & Terr, Eds. (1991). Moreover, the immunoassays of the present invention can be performed in any of several configurations, e.g., those reviewed in *Enzyme Immunoassay*, Maggio, Ed., CRC Press, Boca Raton, Fla. (1980); Tijan, Practice and Theory of Enzyme Immunoassays, *Laboratory Techniques in Biochemistry and Molecular Biology*, Elsevier Science Publishers B. V., Amsterdam (1985); Harlow and Lane, supra; *Immunoassay: A Practical Guide*, Chan, Ed., Academic Press, Orlando, Fla. (1987); *Principles and Practice of Immunoassays*, Price and Newman Eds., Stockton Press, NY (1991); and *Non-isotopic Immunoassays*, Ngo, Ed., Plenum Press, NY (1988).

Typical methods include Western blot (immunoblot) analysis, analytic biochemical methods such as electrophoresis, capillary electrophoresis, high performance liquid chromatography (HPLC), thin layer chromatography (TLC), hyperdiffusion chromatography, and the like, and various immunological methods such as fluid or gel precipitin reactions, immunodiffusion (single or double), immunoelectrophoresis, radioimmunoassays (RIAs), enzyme-linked immunosorbent assays (ELISAs), immunofluorescent assays, and the like.

Non-radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with the labeled, naturally occurring anti-ligands. Alternatively, any haptenic or antigenic compound can be used in combination with an antibody.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems which may be used, see, U.S. Pat. No. 4,391,904, which is incorporated herein by reference.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

The proteins of the present invention can be used for identifying compounds that bind to (e.g., substrates), and/or increase or decrease (i.e., modulate) the enzymatic activity of, catalytically active polypeptides of the present invention. The method comprises contacting a polypeptide of the present invention with a compound whose ability to bind to or modulate enzyme activity is to be determined. The polypeptide employed will have at least 20%, 30%, 40%, 50%, 60%, 70%, 80%, 90% or 95% of the specific activity of the native, full-length polypeptide of the present invention (e.g., enzyme). Methods of measuring enzyme kinetics are well known in the art. See, e.g., Segel, *Biochemical Calculations*, $2^{nd}$ ed., John Wiley and Sons, New York (1976).

Antibodies can be raised to a protein of the present invention, including individual, allelic, strain, or species variants, and fragments thereof, both in their naturally occurring (full-length) forms and in recombinant forms. Additionally, antibodies are raised to these proteins in either their native configurations or in non-native configurations. Anti-idiotypic antibodies can also be generated. Many methods of making antibodies are known to persons of skill.

In some instances, it is desirable to prepare monoclonal antibodies from various mammalian hosts, such as mice, rodents, primates, humans, etc. Description of techniques for preparing such monoclonal antibodies are found in, e.g., *Basic and Clinical Immunology*, 4th ed., Stites et al., Eds., Lange Medical Publications, Los Altos, Calif., and references cited therein; Harlow and Lane, Supra; Goding, *Monoclonal Antibodies: Principles and Practice*, 2nd ed., Academic Press, New York, N.Y. (1986); and Kohler and Milstein, *Nature* 256:495–497 (1975).

Other suitable techniques involve selection of libraries of recombinant antibodies in phage or similar vectors (see, e.g., Huse et al., *Science* 246:1275–1281 (1989); and Ward et al., *Nature* 341:544–546 (1989); and Vaughan et al. *Nature Biotechnology*, 14:309–314 (1996)). Alternatively, high avidity human monoclonal antibodies can be obtained from transgenic mice comprising fragments of the unrearranged human heavy and light chain Ig loci (i.e., minilocus transgenic mice). Fishwild et al., *Nature Biotech.* 14:845–851 (1996). Also, recombinant immunoglobulins may be produced. See, Cabilly, U.S. Pat. No. 4,816,567; and Queen et al., *Proc. Natl. Acad. Sci.* 86:10029–10033 (1989).

The antibodies of this invention can be used for affinity chromatography in isolating proteins of the present invention, for screening expression libraries for particular expression products such as normal or abnormal protein or for raising anti-idiotypic antibodies which are useful for detecting or diagnosing various pathological conditions related to the presence of the respective antigens.

Frequently, the proteins and antibodies of the present invention will be labeled by joining, either covalently or non-covalently, a substance which provides for a detectable signal. A wide variety of labels and conjugation techniques are known and are reported extensively in both the scientific and patent literature. Suitable labels include radionucleotides, enzymes, substrates, cofactors, inhibitors, fluorescent moieties, chemiluminescent moieties, magnetic particles, and the like.

Transformation of Cells

The method of transformation is not critical to the present invention; various methods of transformation are currently available. As newer methods are available to transform crops or other host cells they may be directly applied. Accordingly, a wide variety of methods have been developed to insert a DNA sequence into the genome of a host cell to obtain the transcription and/or translation of the sequence to effect phenotypic changes in the organism. Thus, any method which provides for efficient transformation/transfection may be employed.

A DNA sequence coding for the desired polynucleotide of the present invention, for example a cDNA or a genomic sequence encoding a full length protein, can be used to construct an expression cassette which can be introduced into the desired plant. Isolated nucleic acid acids of the present invention can be introduced into plants according techniques known in the art. Generally, expression cassettes as described above and suitable for transformation of plant cells are prepared.

Techniques for transforming a wide variety of higher plant species are well known and described in the technical, scientific, and patent literature. See, for example, Weising et al., *Ann. Rev. Genet.* 22:421–477 (1988). For example, the DNA construct may be introduced directly into the genomic DNA of the plant cell using techniques such as electroporation, PEG poration, particle bombardment, silicon fiber delivery, or microinjection of plant cell protoplasts or embryogenic callus. See, e.g., Tomes et al., Direct DNA Transfer into Intact Plant Cells Via Microprojectile Bombardment. pp. 197–213 in Plant Cell, Tissue and Organ Culture, Fundamental Methods. eds. O. L. Gamborg and G. C. Phillips. Springer-Verlag Berlin Heidelberg New York, 1995. Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. See, U.S. Pat. No. 5,591,616.

The introduction of DNA constructs using polyethylene glycol precipitation is described in Paszkowski et al., *Embo J.* 3:2717–2722 (1984). Electroporation techniques are described in Fromm et al., *Proc. Natl. Acad. Sci.* 82:5824 (1985). Ballistic transformation techniques are described in Klein et al., *Nature* 327:70–73 (1987).

*Agrobacterium tumefaciens*—meditated transformation techniques are well described in the scientific literature. See, for example Horsch et al., *Science* 233:496–498 (1984), and Fraley et al., *Proc. Natl. Acad. Sci.* 80:4803 (1983). For instance, *Agrobacterium* transformation of maize is described in U.S. Pat. No. 5,981,840. *Agrobacterium* transformation of soybean is described in U.S. Pat. No. 5,563,055.

Other methods of transformation include (1) *Agrobacterium rhizogenes*—mediated transformation (see, e.g., Lichtenstein and Fuller In: Genetic Engineering, Vol. 6, P W J Rigby, Ed., London, Academic Press, 1987; and Lichtenstein, C. P., and Draper, J,. In: DNA Cloning, Vol. II, D. M. Glover, Ed., Oxford, IRI Press, 1985), Application PCT/US87/02512 (WO 88/02405 published Apr. 7, 1988) describes the use of *A. rhizogenes* strain A4 and its Ri plasmid along with *A. tumefaciens* vectors pARC8 or pARC16 (2) liposome-mediated DNA uptake (see, e.g., Freeman et al., *Plant Cell Physiol.* 25:1353, (1984)), (3) the vortexing method (see, e.g., Kindle, *Proc. Natl. Acad. Sci. USA* 87:1228, (1990)).

DNA can also be introduced into plants by direct DNA transfer into pollen as described by Zhou et al., *Methods in Enzymology* 101:433 (1983); D. Hess, *Intern Rev. Cytol.* 107:367 (1987); Luo et al., *Plane Mol. Biol. Reporter* 6:165 (1988). Expression of polypeptide coding polynucleotides can be obtained by injection of the DNA into reproductive organs of a plant as described by Pena et al., *Nature* 325:274 (1987). DNA can also be injected directly into the cells of immature embryos and the rehydration of desiccated embryos as described by Neuhaus et al., *Theor. Appl. Genet.* 75:30 (1987); and Benbrook et al., in Proceedings Bio Expo 1986, Butterworth, Stoneham, Mass., pp. 27–54 (1986).

Animal and lower eukaryotic (e.g., yeast) host cells are competent or rendered competent for transformation by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextran, electroporation, biolistics, and micro-injection of the DNA directly into the cells. The transfected cells are cultured by means well known in the art. Kuchler, R. J., *Biochemical Methods in Cell Culture and Virology*, Dowden, Hutchinson and Ross, Inc. (1977).

Transgenic Plant Regeneration

Transformed plant cells which are derived by any of the above transformation techniques can be cultured to regenerate a whole plant which possesses the transformed genotype. Such regeneration techniques often rely on manipulation of certain phytohormones in a tissue culture growth medium, typically relying on a biocide and/or herbicide marker that has been introduced together with a polynucleotide of the present invention. For transformation and regeneration of maize see, Gordon-Kamm et al., *The Plant Cell* 2:603–618 (1990).

Plants cells transformed with a plant expression vector can be regenerated, e.g., from single cells, callus tissue or leaf discs according to standard plant tissue culture techniques. It is well known in the art that various cells, tissues, and organs from almost any plant can be successfully cultured to regenerate an entire plant. Plant regeneration from cultured protoplasts is described in Evans et al., *Protoplasts Isolation and Culture, Handbook of Plant Cell Culture*, Macmillan Publishing Company, New York, pp. 124–176 (1983); and Binding, *Regeneration of Plants, Plant Protoplasts*, CRC Press, Boca Raton, pp. 21–73 (1985).

The regeneration of plants containing the foreign gene introduced by *Agrobacterium* can be achieved as described by Horsch et al., *Science* 227:1229–1231 (1985) and Fraley et al., *Proc. Natl. Acad. Sci. U. S. A.* 80:4803 (1983). This procedure typically produces shoots within two to four weeks and these transformant shoots are then transferred to an appropriate root-inducing medium containing the selective agent and an antibiotic to prevent bacterial growth. Transgenic plants of the present invention may be fertile or sterile.

Regeneration can also be obtained from plant callus, explants, organs, or parts thereof. Such regeneration techniques are described generally in Klee et al., *Ann. Rev. of Plant Phys.* 38:467–486 (1987). The regeneration of plants from either single plant protoplasts or various explants is well known in the art. See, for example, Methods for Plant Molecular Biology, A. Weissbach and H. Weissbach, eds., Academic Press, Inc., San Diego, Calif. (1988). For maize cell culture and regeneration see generally, *The Maize Handbook*, Freeling and Walbot, Eds., Springer, New York (1994); *Corn and Corn Improvement*, $3^{rd}$ edition, Sprague and Dudley Eds., American Society of Agronomy, Madison, Wis. (1988).

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

In vegetatively propagated crops, mature transgenic plants can be propagated by the taking of cuttings, via production of apomictic seed, or by tissue culture techniques to produce multiple identical plants. Selection of desirable transgenics is made and new varieties are obtained and propagated vegetatively for commercial use. In seed propagated crops, mature transgenic plants can be self crossed to produce a homozygous inbred plant. The inbred plant produces seed containing the newly introduced heterologous nucleic acid. These seeds can be grown to produce plants that would produce the selected phenotype.

Parts obtained from the regenerated plant, such as flowers, seeds, leaves, branches, fruit, and the like are included in the invention, provided that these parts comprise cells comprising the isolated nucleic acid of the present invention. Progeny and variants, and mutants of the regenerated plants are also included within the scope of the invention, provided that these parts comprise the introduced nucleic acid sequences.

Transgenic plants expressing a selectable marker can be screened for transmission of the nucleic acid of the present invention by, for example, standard immunoblot and DNA detection techniques. Transgenic lines are also typically evaluated on levels of expression of the heterologous nucleic acid. Expression at the RNA level can be determined initially to identify and quantitate expression-positive plants. Standard techniques for RNA analysis can be employed and include PCR amplification assays using oligonucleotide primers designed to amplify only the heterologous RNA templates and solution hybridization assays using heterologous nucleic acid-specific probes. The RNA-positive plants can then be analyzed for protein expression by Western immunoblot analysis using the specifically reactive antibodies of the present invention. In addition, in situ hybridization and immunocytochemistry according to standard protocols can be done using heterologous nucleic acid specific polynucleotide probes and antibodies, respectively, to localize sites of expression within transgenic tissue. Generally, a number of transgenic lines are usually screened for the incorporated nucleic acid to identify and select plants with the most appropriate expression profiles.

Another embodiment is a transgenic plant that is homozygous for the added heterologous nucleic acid; i.e., a transgenic plant that contains two added nucleic acid sequences, one gene at the same locus on each chromosome of a chromosome pair. A homozygous transgenic plant can be obtained by sexually mating (selfing) a heterozygous transgenic plant that contains a single added heterologous nucleic acid, germinating some of the seed produced and analyzing the resulting plants produced for altered expression of a polynucleotide of the present invention relative to a control plant (i.e., native, non-transgenic). Still another embodiment involves back-crossing to a parental plant and/or out-crossing with a non-transgenic plant.

Seeds derived from plants regenerated from transformed plant cells, plant parts or plant tissues, or progeny derived from the regenerated transformed plants, may be used directly as feed or food, or further processing may occur.

The present invention may be used for transformation of any plant species, monocotyledonous and dicotyledonous, including, but not limited to, corn (*Zea mays*), Brassica sp. (e.g., *B. napus, B. rapa, B. juncea*), particularly those Brassica species useful as sources of seed oil, alfalfa (*Medicago sativa*), rice (*Oryza sativa*), rye (*Secale cereale*), sorghum (*Sorghum bicolor, Sorghum vulgare*), sunflower (*Helianthus annuus*), safflower (*Carthamus tinctorius*), millet (*Pennisetum glaucum, Panicum miliaceum, Eleusine coracana, Setaria italica*), wheat (*Triticum aestivum*), soybean (*Glycine max*), tobacco (*Nicotiana tabacum*), potato (*Solanum tuberosum*), peanuts (*Arachis hypogaea*), cotton (*Gossypium hirsutum*), sweet potato (*Ipomoea batatus*), cassava (*Manihot esculenta*), coffee (Cofea spp.), coconut (*Cocos nucifera*), pineapple (*Ananas comosus*), citrus trees (Citrus spp.), cocoa (*Theobroma cacao*), tea (*Camellia sin-* ensis), banana (Musa spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), oats, barley (*Hordeum vulgare*), vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (Lathyrus spp.), and members of the genus Cucumis such as cucumber (*C. sativus*), cantaloupe (*C. cantalupensis*), and musk melon (*C. melo*). Ornamentals include azalea (Rhododendron spp.), hydrangea (*Macrophylla hydrangea*), hibiscus (*Hibiscus rosasanensis*), roses (Rosa spp.), tulips (Tulipa spp.), daffodils (Narcissus spp.), petunias (*Petunia hybrida*), carnation (*Dianthus caryophyllus*), poinsettia (*Euphorbia pulcherrima*), and chrysanthemum. Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*).

Plants of the present invention include crop plants (for example, corn, alfalfa, sunflower, safflower, canola, soybean, casava, cotton, peanut, sorghum, rice, wheat, millet, tobacco, rye, oats, barley, turf grass, etc.). In one embodiment plants of the present invention include corn, soybean, canola, rice, sunflower, wheat and sorghum plants, and in another corn and soybean plants.

Insect Pests

The compositions of the present invention may be effective against a variety of plant pests including but not limited to insects of the order Lepidoptera, e.g. *Achoroia grisella, Acleris gloverana, Acleris variana, Adoxophyes orana, Agrotis ipsilon, Alabama argillacea, Alsophila pometaria, Amyelois transitella, Anagasta kuehniella, Anarsia lineatella, Anisota senatoria, Antheraea pernyi, Anticarsia gemmatalis*, Archips sp., Argyrotaenia sp., *Athetis mindara, Bombyx mori, Bucculatrix thurberiella, Cadra cautella*, Choristoneura sp., *Cochylls hospes, Colias eurytheme, Corcyra cephalonica, Cydia latiferreanus, Cydia pomonella, Datana integeffima, Dendrolimus sibericus, Desmia feneralis, Diaphania hyalinata, Diaphania nitidalis, Diatraea grandiosella, Diatraea saccharalis, Ennomos subsignaria, Eoreuma loffini, Esphestia elutella, Erannis tilaria, Estigmene acrea, Eulia salubricola, Eupocoellia ambiguella, Eupoecilia ambiguella, Euproctis chrysorrhoea, Euxoa messoria, Galleria mellonella, Grapholita molesta, Harrisina americana, Helicoverpa subflexa, Helicoverpa zea, Heliothis virescens, Hemileuca oliviae, Homoeosoma electellum, Hyphantia cunea, Keiferia lycopersicella, Lambdina fiscellaria fiscellaria, Lambdina fiscellaria lugubrosa, Leucoma salicis, Lobesia botrana, Loxostege sticticalis, Lymantria dispar, Macalla thyrisalis*, Malacosoma sp., *Mamestra brassicae, Mamestra configurata, Manduca quinquemaculata, Manduca sexta, Maruca testulalis, Melanchra picta, Operophtera brumata*, Orgyia sp., *Ostrinia nubilalis, Paleacrita vemata, Papilio cresphontes, Pectinophora gossypiella, Phryganidia californica, Phyllonorycter blancardella, Pieris napi, Pieris rapae, Plathypena scabra, Platynota flouendana, Platynota stultana, Platyptilia carduidactyla, Plodia interpunctella, Plutella xylostella, Pontia protodice, Pseudaletia unipuncta, Pseudoplasia includens, Sabulodes aegrotata, Schizura concinna, Sitotroga cerealella, Spilonta ocellana*, Spodoptera sp., *Thaurnstopoea pityocampa, Tinsola bisselliella, Trichoplusia hi, Udea rubigalis, Xylomyges curiails*, and *Yponomeuta padella*.

Also, the compositions of the present invention may be effective against insect pests including insects selected from the orders Diptera, Hymenoptera, Lepidoptera, Mallophaga, Homoptera, Hemiptera, Orthroptera, Thysanoptera, Dermaptera, Isoptera, Anoplura, Siphonaptera, Trichoptera, etc., particularly Coleoptera, especially *Diabrotica virgifera* and Lepidoptera. Insect pests of the invention for the major crops include: Maize: *Ostrinia nubilalis*, European corn borer; *Agrotis ipsilon*, black cutworm; *Helicoverpa zea*, corn earworm; *Spodoptera frugiperda*, fall armyworm; *Diatraea grandiosella*, southwestern corn borer; *Elasmopalpus lignosellus*, lesser cornstalk borer; *Diatraea saccharalis*, surgarcane borer; *Diabrotica virgifera*, western corn rootworm; *Diabrotica longicornis barberi*, northern corn rootworm; *Diabrotica undecimpunctata howardi*, southern corn rootworm; Melanotus spp., wireworms; *Cyclocephala borealis*, northern masked chafer (white grub); *Cyclocephala immaculata*, southern masked chafer (white grub); *Popillia japonica*, Japanese beetle; *Chaetocnema pulicaria*, corn flea beetle; *Sphenophorus maidis*, maize billbug; *Rhopalosiphum maidis*, corn leaf aphid; *Anuraphis maidiradicis*, corn root aphid; *Blissus leucopterus leucopterus*, chinch bug; *Melanoplus femurrubrum*, redlegged grasshopper; *Melanoplus sanguinipes*, migratory grasshopper; *Hylemya platura*, seedcorn maggot; *Agromyza parvicomis*, corn bloth leafminer; *Anaphothrips obscrurus*, grass thrips; *Solenopsis milesta*, thief ant; *Tetranychus urticae*, two spotted spider mite; Sorghum: *Chilo partellus*, sorghum borer; *Spodoptera frugiperda*, fall armyworm; *Helicoverpa zea*, corn earworm; *Elasmopalpus lignosellus*, leser cornstalk borer; *Feltia subterranea*, granulate cutworm; *Phyllophaga crinita*, white grub; Eleodes, Conoderus, and Aeolus spp., wireworms; *Oulema melanopus*, cereal leaf beetle; *Chaetocnema pulicaria*, corn flea beetle; *Sphenophorus maidis*, maize billbug; *Rhopalosiphum maidis*; corn leaf aphid; *Sipha flava*, yellow sugarcane aphid; *Blissus leucopterus leucopterus*, chinch bug; *Contarinia sorghicola*, sorghum midge; *Tetranychus cinnabarinus*, carmine spider mite; *Tetranychus urticae*, twospotted spider mite; Wheat: *Pseudaletia unipunctata*, army worm; *Spodoptera frugiperda*, fall armyworm; *Elasmopalpus lignosellus*, lesser cornstalk borer; *Agrotis orthogonia*, plae western cutworm; *Elasmopalpus lignosellus*, lesser cornstalk borer; *Oulema melanopus*, cereal leaf beetle; *Hypera punctata*, clover leaf weevil; *Diabrotica undecimpunctata howardi*, southern corn rootworm; Russian wheat aphid; *Schizaphis graminum*, greenbug; *Macrosiphum avenae*, English grain aphid; *Melanoplus femurrubrum*, redlegged grasshopper; *Melanoplus differentialis*, differential grasshopper; *Melanoplus sanguinipes*, migratory grasshopper; *Mayetiola destructor*, Hessian fly; *Sitodiplosis mosellana*, wheat midge; *Meromyza americana*, wheat stem maggot; *Hylemya coarctata*, wheat bulb fly; *Frankliniella fusca*, tobacco thrips; *Cephus cinctus*, wheat stem sawfly; *Aceria tulipae*, wheat curl mite; Sunflower: *Suleima helianthana*, sunflower bud moth; *Homoeosoma electellum*, sunflower moth; *zygogramma exclamationis*, sunflower beetle; *Bothyrus gibbosus*, carrot beetle; *Neolasioptera murtfeldtiana*, sunflower seed midge; Cotton: *Heliothis virescens*, cotton boll worm; *Helicoverpa zea*, cotton bollworm;

*Spodoptera exigua*, beet armyworm; *Pectinophora gossypiella*, pink bollworm; *Anthonomus grandis*, bool weevil; *Aphis gossypii*, cotton aphid; *Pseudatomoscelis seriatus*, cotton fleahopper; *Trialeurodes abutilonea*, bandedwinged whitefly; *Lygus lineolaris*, tarnished plant bug; *Melanoplus femurrubrum*, redlegged grasshopper; *Melanoplus differentialis*, differential grasshopper; *Thrips tabaci*, onion thrips; *Franklinkiella fusca*, tobacco thrips; *Tetranychus cinnabarinus*, carmine spider mite; *Tetranychus urticae*, twospotted spider mite; Rice: *Diatraea saccharalis*, sugarcane borer; *Spodoptera frugiperda*, fall armyworm; *Helicoverpa zea*, corn earworm; *Colaspis brunnea*, grape colaspis; *Lissorhoptrus oryzophilus*, rice water weevil; *Sitophilus oryzae*, rice weevil; *Nephotettix nigropictus*, rice leafhoper; *Blissus leucopterus leucopterus*, chinch bug; *Acrosternum hilare*, green stink bug; Soybean: *Pseudoplusia includens*, soybean looper; *Anticarsia gemmatalis*, velvetbean caterpillar; *Plathypena scabra*, green cloverworm; *Ostrinia nubilalis*, European corn borer; *Agrotis ipsilon*, black cutworm; *Spodoptera exigua*, beet armyworm; *Heliothis virescens*, cotton boll worm; *Helicoverpa zea*, cotton bollworm; *Epilachna varivestis*, Mexican bean beetle; *Myzus persicae*, green peach aphid; *Empoasca fabae*, potato leafhopper; *Acrosternum hilare*, green stink bug; *Melanoplus femurrubrum*, redlegged grasshopper; *Melanoplus differentialis*, differential grasshopper; *Hylemya platura*, seedcorn maggot; *Sericothrips variabilis*, soybean thrips; *Thrips tabaci*, onion thrips; *Tetranychus turkestani*, strawberry spider mite; *Tetranychus urticae*, twospotted spider mite; Barley: *Ostrinia nubilalis*, European corn borer; *Agrotis ipsilon*, black cutworm; *Schizaphis graminum*, greenbug; *Blissus leucopterus leucopterus*, chinch bug; *Acrosternum hilare*, green stink bug; *Euschistus servus*, brown stink bug; *Jylemya platura*, seedcorn maggot; *Mayetiola destructor*, Hessian fly; *Petrobia latens*, brown wheat mite; Oil Seed Rape: *Vrevicoryne brassicae*, cabbage aphid.

Furthermore, compositions of the present invention may be effective against Hemiptera such as *Lygus hesperus, Lygus lineolaris, Lygus pratensis, Lygus rugulipennis* Popp, *Lygus pabulinus, Calocoris norvegicus, Orthops compestris, Plesiocoris rugicollis, Cyrtopeltis modestus, Cyrtopeltis notatus, Spanagonicus albofasciatus, Diaphnocoris chlorinonis, Labopidicola allii, Pseudatomoscelis seriatus, Adelphocoris rapidus, Poecilocapsus lineatus, Blissus leucopterus, Nysius ericae, Nysiusraphanus, Euschistus servus, Nezara viridula*, Eurygaster, Coreidae, Pyrrhocoridae, Tinidae, Blostomatidae, Reduviidae, and Cimicidae.

The preferred stage of experimental organism for testing for pesticidal activity is larvae or immature forms of these above mentioned insect pest. Experimental organisms may be reared in total darkness at from about 20° C. to about 30° C. and from about 30% to about 70% relative humidity. Bioassays may be performed as described in Czapla T. H. and Lang B. A. Effect of Plant Lectins on the Larval Development of European Corn Borer (Lepidoptera: Pyralidae) and Southern Corn Rootworm (Coleoptera: Chrysomelidae), J. Econ. Entomol. 83(6): 2480–2485 (1990). Methods of rearing insect pest larvae and performing bioassays are well known to one skilled in the art.

A wide variety of bioassay techniques are known to one skilled in the art. General procedures include addition of experimental compound to the diet source in an enclosed container. Pesticidal activity can be measured by, but is not limited to, mortality, weight loss, attraction, repellency and other behavioral and physical changes after feeding and exposure for an appropriate length of time. Bioassays described herein, can be used with any feeding insect pest in the larval or adult stage.

Disease

The methods of the invention can be used with other methods available in the art for enhancing disease resistance in plants. Similarly, the plant defense mechanisms described herein may be used alone or in combination with other proteins or agents to protect against plant diseases and pathogens.

Pathogens of the invention include, but are not limited to, viruses or viroids, bacteria, insects, nematodes, fungi, and the like. Viruses include any plant virus, for example, tobacco or cucumber mosaic virus, ringspot virus, necrosis virus, maize dwarf mosaic virus, etc. Specific fungal and viral pathogens for the major crops include: Soybeans: *Phytophthora megasperma* f.sp. *glycinea*, *Macrophomina phaseolina, Rhizoctonia solani, Sclerotinia sclerotiorum, Fusarium oxysporum, Diaporthe phaseolorum* var. *sojae* (*Phomopsis sojae*), *Diaporthe phaseolorum* var. *caulivora, Sclerotium rolfsii, Cercospora kikuchiil, Cercospora sojina, Peronospora manshurica, Colletotrichum dematium* (*Colletotichum truncatum*), *Corynespora cassiicola, Septoria glycines, Phyllosticta sojicola, Alternaria alternata, Pseudomonas syringae* p.v. *glycinea, Xanthomonas campestris* p.v. *phaseoli, Microsphaera diffusa, Fusarium semitectum, Phialophora gregata*, Soybean mosaic virus, *Glomerella glycines*, Tobacco Ring spot virus, Tobacco Streak virus, *Phakopsora pachyrhizi, Pythium aphanidermatum, Pythium ultimum, Pythium debaryanum*, Tomato spotted wilt virus, *Heterodera glycines Fusarium solani*; Canola: *Albugo candida, Alternaria brassicae, Leptosphaeria maculans, Rhizoctonia solani, Scierotinia scierotiorum, Mycosphaerella brassiccola, Pythium ultimum, Peronospora parasitica, Fusarium roseum, Alternaria alternata*; Alfalfa: *Clavibater michiganese* subsp. *insidiosum, Pythium ultimum, Pythium irregulare, Pythium splendens, Pythium debaryanum, Pythium aphanidermatum, Phytophthora megasperma, Peronospora trifoliorum, Phoma medicaginis* var. *medicaginis, Cercospora medicaginis, Pseudopeziza medicaginis, Leptotrochila medicaginis, Fusarium, Xanthomonas campestris* p.v. *alfalfae, Aphanomyces euteiches, Stemphylium herbarum, Stemphylium alfalfae*; Wheat: *Pseudomonas syringae* p.v. *atrofaciens, Urocystis agropyri, Xanthomonas campestris* p.v. *translucens, Pseudomonas syringae* p.v. *syringae, Alternaria alternata, Cladosporium herbarum, Fusarium graminearum, Fusarium avenaceum, Fusarium culmorum, Ustilago tritici, Ascochyta tritici, Cephalosporium gramineum, Collotetrichum graminicola, Erysiphe graminis* f.sp. *tritici, Puccinia graminis* f.sp. *tritici, Puccinia recondita* f.sp. *tritici, Puccinia striiformis, Pyrenophora tritici-repentis, Septoria nodorum, Septoria tritici, Septoria avenae, Pseudocercosporella herpotrichoides, Rhizoctonia solani, Rhizoctonia cerealis, Gaeumannomyces graminis* var. *tritici, Pythium aphanidermatum, Pythium arrhenomanes, Pythium ultimum, Bipolaris sorokiniana*, Barley Yellow Dwarf Virus, Brome Mosaic Virus, Soil Borne Wheat Mosaic Virus, Wheat Streak Mosaic Virus, Wheat Spindle Streak Virus, American Wheat Striate Virus, *Claviceps purpurea, Tilletia tritici, Tilletia laevis, Ustilago tritici, Tilletia indica, Rhizoctonia solani, Pythium arrhenomannes, Pythium gramicola, Pythium aphanidermatum*, High Plains Virus, European wheat striate virus; Sunflower: Orobanche, *Plasmophora halstedii, Sclerotinia sclerotiorum*, Aster Yellows, *Septoria helianthi, Phomopsis helianthi*,

*Alternaria helianthi, Alternaria zinniae, Botrytis cinerea, Phoma macdonaldii, Macrophomina phaseolina, Erysiphe cichoracearum, Rhizopus oryzae, Rhizopus arrhizus, Rhizopus stolonifer, Puccinia helianthi, Verticillium dahliae, Erwinia carotovorum* pv. *carotovora, Cephalosporium acremonium, Phytophthora cryptogea, Albugo tragopogonis*; Corn: *Fusarium moniliforme* var. *subglutinans, Erwinia stewartii, Fusarium moniliforme, Gibberella zeae (Fusarium graminearum), Stenocarpella maydi (Diplodia maydis), Pythium irregulare, Pythium debaryanum, Pythium graminicola, Pythium splendens, Pythium ultimum, Pythium aphanidermatum, Aspergillus flavus, Bipolaris maydis* O,T (*Cochliobolus heterostrophus*), *Helminthosporium carbonum* I, II & III (*Cochliobolus carbonum*), *Exserohilum turcicum* I, II & III, *Helminthosporium pedicellatum, Physoderma maydis, Phyllosticta maydis, Kabatiella-maydis, Cercospora sorghi, Ustilago maydis, Puccinia sorghi, Puccinia polysora, Macrophomina phaseolina, Penicillium oxalicum, Nigrospora oryzae, Cladosporium herbarum, Curvularia lunata, Curvularia inaequalis, Curvularia pallescens, Clavibacter michiganense* subsp. *nebraskense, Trichoderma viride*, Maize Dwarf Mosaic Virus A & B, Wheat Streak Mosaic Virus, Maize Chlorotic Dwarf Virus, *Claviceps sorghi, Pseudonomas avenae, Erwinia chrysanthemi* pv. *zea, Erwinia carotovora*, Com stunt spiroplasma, *Diplodia macrospora, Sclerophthora macrospora, Peronosclerospora sorghi, Peronosclerospora philippinensis, Peronosclerospora maydis, Peronosclerospora sacchari, Sphacelotheca reiliana, Physopella zeae, Cephalosporium maydis, Cephalosporium acremonium*, Maize Chlorotic Mottle Virus, High Plains Virus, Maize Mosaic Virus, Maize Rayado Fino Virus, Maize Streak Virus, Maize Stripe Virus, Maize Rough Dwarf Virus; Sorghum: *Exserohilum turcicum, Colletotrichum graminicola (Glomerella graminicola), Cercospora sorghi, Gloeocercospora sorghi, Ascochyta sorghina, Pseudomonas syringae* p.v. *syringae, Xanthomonas campestris* p.v. *holcicola, Pseudomonas andropogonis, Puccinia purpurea, Macrophomina phaseolina, Perconia circinata, Fusarium moniliforme, Alternaria alternata, Bipolaris sorghicola, Helminthosporium sorghicola, Curvularia lunata, Phoma insidiosa, Pseudomonas avenae (Pseudomonas alboprecipitans), Ramulispora sorghi, Ramulispora sorghicola, Phyllachara sacchari, Sporisorium reilianum (Sphacelotheca reiliana), Sphacelotheca cruenta, Sporisorium sorghi, Sugarcane mosaic H*, Maize Dwarf Mosaic Virus A & B, *Claviceps sorghi, Rhizoctonia solani, Acremonium strictum, Sclerophthona macrospora, Peronoscierospora sorghi, Peronosclerospora philippinensis, Sclerospora graminicola, Fusarium graminearum, Fusarium oxysporum, Pythium arrhenomanes, Pythium graminicola*, etc.

Nematodes include parasitic nematodes such as root-knot, cyst, lesion, and renniform nematodes, etc.

All publications cited in this application are herein incorporated by reference to the same extent as if each individual publication or patent application was specifically and individually indicated to be incorporated by reference.

The present invention will be further described by reference to the following detailed examples. It is understood, however, that there are many extensions, variations, and modifications on the basic theme of the present invention beyond that shown in the examples and description, which are within the spirit and scope of the present invention.

EXAMPLES

Example 1

Library Construction used for Maize and Soybean BI EST's

A. Total RNA Isolation

Total RNA was isolated from various maize or soybean tissues with TRIzol Reagent (Life Technology Inc. Gaithersburg, Md.) using a modification of the guanidine isothiocyanate/acid-phenol procedure described by Chomczynski and Sacchi (Chomczynski, P., and Sacchi, N. *Anal. Biochem.* 162, 156 (1987)). In brief, plant tissue samples were pulverized in liquid nitrogen before the addition of the TRIzol Reagent, and then were further homogenized with a mortar and pestle.

Addition of chloroform followed by centrifugation was conducted for separation of an aqueous phase and an organic phase. The total RNA was recovered by precipitation with isopropyl alcohol from the aqueous phase.

B. Poly(A)+ RNA Isolation

The selection of poly(A)+ RNA from total RNA was performed using PolyATact system (Promega Corporation. Madison, Wis.). In brief, biotinylated oligo(dT) primers were used to hybridize to the 3' poly(A) tails on mRNA. The hybrids were captured using streptavidin coupled to paramagnetic particles and a magnetic separation stand. The mRNA was washed at high stringent condition and eluted by RNase-free deionized water.

C. cDNA Library Construction cDNA synthesis was performed and unidirectional cDNA libraries were constructed using the SuperScript Plasmid System (Life Technology Inc. Gaithersburg, Md.). The first stand of cDNA was synthesized by priming an oligo(dT) primer containing a Not I site. The reaction was catalyzed by SuperScript Reverse Transcriptase II at 45° C. The second strand of cDNA was labeled with alpha-$^{32}$P-dCTP and a portion of the reaction was analyzed by agarose gel electrophoresis to determine cDNA sizes. cDNA molecules smaller than 500 base pairs and unligated adapters were removed by Sephacryl-S400 chromatography. The selected cDNA molecules were ligated into pSPORT1 vector in between of Not I and Sal I sites.

Example 2

Sequencing and cDNA Subtraction Procedures used for Maize and Soybean BI EST's

A. Sequencing Template Preparation

Individual colonies were picked and DNA was prepared either by PCR with M13 forward primers and M13 reverse primers, or by plasmid isolation. All the cDNA clones were sequenced using M13 reverse primers.

B. Q-bot Subtraction Procedure cDNA libraries subjected to the subtraction procedure were plated out on 22×22 cm² agar plate at density of about 3,000 colonies per plate. The plates were incubated in a 37° C. incubator for 12–24 hours. Colonies were picked into 384-well plates by a robot colony picker, Q-bot (GENETIX Limited). These plates were incubated overnight at 37° C.

Once sufficient colonies were picked, they were pinned onto 22×22 cm² nylon membranes using Q-bot. Each membrane contained 9,216 colonies or 36,864 colonies. These membranes were placed onto agar plate with appropriate antibiotic. The plates were incubated at 37° C. for overnight.

After colonies were recovered on the second day, these filters were placed on filter paper prewetted with denaturing solution for four minutes, then were incubated on top of a boiling water bath for additional four minutes. The filters were then placed on filter paper prewetted with neutralizing solution for four minutes. After excess solution was removed by placing the filters on dry filter papers for one minute, the colony side of the filters were place into Proteinase K solution, incubated at 37° C. for 40–50 minutes. The filters were placed on dry filter papers to dry overnight. DNA was then cross-linked to nylon membrane by UV light treatment.

Colony hybridization was conducted as described by Sambrook, J., Fritsch, E. F. and Maniatis, T., (in Molecular Cloning: A laboratory Manual, 2$^{nd}$ Edition). The following probes were used in colony hybridization:
1. First strand cDNA from the same tissue from which the library was made to remove the most redundant clones.
2. 48–192 most redundant cDNA clones from the same library based on previous sequencing data.
3. 192 most redundant cDNA clones in the entire corn sequence database.
4. A Sal-A20 oligo nucleotide: TCG ACC CAC GCG TCC GM AAA AAA AAA AAA AAA AAA, removes clones containing a poly A tail but no cDNA.
5. cDNA clones derived from rRNA.

The image of the autoradiography was scanned into computer and the signal intensity and cold colony addresses of each colony was analyzed. Re-arraying of cold-colonies from 384 well plates to 96 well plates was conducted using Q-bot.

Example 3

Identification of Maize and Soybean BI EST's from a Computer Homology Search

Gene identities were determined by conducting BLAST (Basic Local Alignment Search Tool; Altschul, S. F., et al., (1993) *J. Mol. Biol.* 215:403–410; see also www.ncbi.nlm.nih.gov/BLAST/) searches under default parameters for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases. For the NCBI Nonredundant (NR) database last release of which was Feb. 17, 2001 at 4:52 AM, containing 197,782,823 letters and 625,274 sequences. For the NCBI Nucleotide (NT) database last release of which was Feb. 17, 2001 at 4:52 AM, containing 2,752,804,350 letters and 775,058 sequences. The cDNA sequences were analyzed for similarity to all publicly available DNA sequences contained in the "nr" database using the BLASTN algorithm. The DNA sequences were translated in all reading frames and compared for similarity to all publicly available protein sequences contained in the "nr" database using the BLASTX algorithm (Gish, W. and States, D. J. (1993) *Nature Genetics* 3:266–272) provided by the NCBI. In some cases, the sequencing data from two or more clones containing overlapping segments of DNA were used to construct contiguous DNA sequences.

Example 4

Composition of cDNA Libraries Used to Isolate and Sequence Additional cDNA Clones cDNA libraries representing mRNAs from various maize (genotype B73) tissues were generated Based on the distribution of BI EST's, the tissue sources from which the various maize BI genes can be derived are presented in Table 1 below.

TABLE 1

Maize tissues used for RNA extraction and construction of cDNA libraries, from which the indicated ZmBI-related ESTs (and ultimately the full-length genes) can be derived (as indicated).

| Tissue source for library* | ZmBI Gene | | | | | | |
|---|---|---|---|---|---|---|---|
| | 1-1 | 1-2 | 1-3 | 1-4 | 1-5 | 1-6 | 1-7 |
| leaf[1] | X | | X | | X | | |
| stress[2] | | X | | | | | |
| kernel | | | | X | | | |
| embryo | | | | X | | | |
| stalk (stem) | | | | | | | X |
| whorl | | | | | | | X |
| seedling | | | | | X | | |

[1]= RNA extracted from seedling leaves
[2]= RNA extracted from stress-induced seedlings
*These libraries were normalized essentially as described in U.S. Pat. No. 5,482,845, incorporated herein by reference.

In a similar fashion, cDNA libraries representing mRNAs from various soybean tissues were generated, and used to identify soybean BI genes.

TABLE 2

Identity of Glycine max soybean clone, reference EST, line and tissue from which genes were identified.

| Gene | Reference EST | Line | Tissue |
|---|---|---|---|
| Gm-BI1-1 | sls1c.pk024.d8 or sls1c.pk011.p17 | Wye genotype | Embryo |
| Gm-BI1-2 | ses4d.pk0036.d1 | Wye genotype | Cells, culture |
| Gm-BI1-3 | sl2.pk0091.d2 | Wye genotype | Pods |
| Gm-BI1-4 | sdp4c.pk036.m11 | Wye genotype | Pods |
| Gm-BI1-5 | sgs4c.pk002.g3 | Wye genotype | Seeds, flower |
| Gm-BI1-6 | sdp2c.pk032.l20 | Wye genotype | Pods |
| Gm-BI1-7 | sfl1n.pk0001.b6 | Wye genotype | Pods |
| Gm-BI1-8 | sl2.pk0031.c3 | Williams 82 genotype | Seedling, shoot, leaf |
| Gm-BI1-9 | sls2c.pk010.d12 | Wye genotype | Pods |
| Gm-BI1-10 | src2c.pk015.h4 | Soy/437654 | Root | cDNA libraries were prepared in Uni-ZAP™ XR vectors according to the manufacturer's protocol (Stratagene Cloning Systems, La Jolla, Calif.). Conversion of the Uni-ZAP™ libraries into plasmid libraries was accomplished according to the protocol provided by Stratagene. Upon conversion, cDNA inserts were contained in the plasmid vector pBluescript. cDNA inserts from randomly picked bacterial colonies containing recombinant pBluescript plasmids were amplified via polymerase chain reaction using primers specific for vector sequences flanking the inserted cDNA sequences or plasmid DNA was prepared from cultured bacterial cells. Amplified insert DNAs or plasmid DNAs were sequenced in dye-primer sequencing reactions to generate partial cDNA sequences (expressed sequence tags or "ESTs"; see Adams, M. D. et al., (1991) *Science* 252:1651).

Example 5

Transformation and Regeneration of Maize Callus

Immature maize embryos from greenhouse or field grown High type 11 donor plants are bombarded with a plasmid containing a polynucleotide of the invention (BI). The BI polynucleotide is operably linked to a constitutive promoter such as nos, or an inducible promoter, such as In2, plus a plasmid containing the selectable marker gene PAT (Wohileben et al. (1988) Gene 70:25–37) that confers resistance to the herbicide Bialaphos, fused to the Green Fluorescence protein. Transformation is performed as follows.

The ears are surface sterilized in 50% Chlorox bleach plus 0.5% Micro detergent for 20 minutes, and rinsed two times with sterile water. The immature embryos are excised and placed embryo axis side down (scutellum side up), 25 embryos per plate. These were cultured on 560 L medium 4 days prior to bombardment in the dark. Medium 560 L is an N6-based medium containing Eriksson's vitamins, thiamine, sucrose, 2,4-D, and silver nitrate. The day of bombardment, the embryos are transferred to 560 Y medium for 4 hours and are arranged within the 2.5-cm target zone. Medium 560Y is a high osmoticum medium (560L with high sucrose concentration).

TABLE 3

|  | (560L) | (560Y) | (560P) |
| --- | --- | --- | --- |
| CHU(N6) BASAL SALTS | 4.0 g/l | 4.0 g/l | 4.0 g/l |
| ERIKSSON'S VITAMIN MIX (1000X) | 1.0 ml/l | 1.0 ml/l | 1.0 ml/l |
| THIAMINE HCL | 0.5 mg/l | 0.5 mg/l | 0.5 mg/l |
| 2,4-D | 1.0 mg/l | 2.0 mg/l | 2.0 mg/l |
| L-PROLINE | 2.88 g/l | 0.69 g/l | 0.69 g/l |
| SILVER NITRATE | 4.25 mg/l | 0.85 mg/l | 0.85 mg/l |
| SUCROSE | 20.0 g/l | 120.0 g/l | 30.0 g/l |
| GELRITE | 2.0 g/l | 3.0 g/l | 3.0 g/l |
| pH 5.8 |  |  |  |

A plasmid vector comprising a polynucleotide of the invention operably linked to the selected promoter is constructed. This plasmid DNA plus plasmid DNA containing a PAT selectable marker is precipitated onto 1.1 μm (average diameter) tungsten pellets using a $CaCl_2$ precipitation procedure as follows: 100 μl prepared tungsten particles (0.6 mg) in water, 20 μl (2 μg) DNA in Tris-EDTA buffer (1 μg total), 100 μl 2.5 M $CaCl_2$, 40 μl 0.1 M spermidine.

Each reagent is added sequentially to the tungsten particle suspension. The final mixture is sonicated briefly. After the precipitation period, the tubes are centrifuged briefly, liquid removed, washed with 500 μl 100% ethanol, and centrifuged again for 30 seconds. Again the liquid is removed, and 60 μl 100% ethanol is added to the final tungsten particle pellet. For particle gun bombardment, the tungsten/DNA particles are briefly sonicated and 5 μl spotted onto the center of each macrocarrier and allowed to dry about 2 minutes before bombardment.

The sample plates are bombarded at a distance of 8 cm from the stopping screen to the tissue, using a Dupont biolistics helium particle gun. All samples receive a single shot at 650 PSI, with a total of ten aliquots taken from each tube of prepared particles/DNA.

Four to twelve hours post bombardment, the embryos are moved to 560P (a low osmoticum callus initiation medium similar to 560L but with lower silver nitrate), for 3–7 days, then transferred to 560R selection medium, an N6 based medium similar to 560P containing 3 mg/liter Bialaphos, and subcultured every 2 weeks. Multicellular GFP cell clusters become visible after two weeks and their numbers are periodically recorded. After approximately 10 weeks of selection, selection-resistant GFP positive callus clones are sampled for PCR and activity of the polynucleotide of interest (see example 7). Positive lines are transferred to 288J medium, an MS-based medium with lower sucrose and hormone levels (0.5 mg/l zeatin, 1.0 mg/l IAA, 0.1 mg/l ABA, 0.6% sucrose and 3 mg/l bialophos, to initiate plant regeneration. Following somatic embryo maturation (2–4 weeks), well-developed somatic embryos are transferred to medium for germination and transferred to the lighted culture room. Approximately 7–10 days later, developing plantlets are transferred to medium in tubes for 7–10 days until plantlets were well established. Plants are then transferred to inserts in flats (equivalent to 2.5" pot) containing potting soil and grown for 1 week in a growth chamber, subsequently grown an additional 1–2 weeks in the greenhouse, then transferred to Classic™ 600 pots (1.6 gallon) (#14–9674–9; Hummert International, Earth City, Mo.) and grown to maturity. Plants are monitored for expression of the polynucleotide of interest.

It is noted that any suitable method of transformation can be used, such as sonication, electroporation, microinjection, and others, as well as the more established methods for maize which include particle delivery (described above) and Agrobacterium-mediated transformation. Numerous varieties of maize germplasm including publicly-available and proprietary hybrids and inbreds can be transformed using the Agrobacterium mediated DNA delivery method, as described by U.S. Pat. No. 5,981,840, which we follow for this example with the following modifications. Agrobacteria are grown to the log phase in liquid minimal A medium containing 100 μM spectinomycin. Embryos are immersed in a log phase suspension of Agrobacteria adjusted to obtain an effective concentration of $5 \times 10^8$ cfu/ml. Embryos are infected for 5 minutes and then co-cultured on culture medium containing acetosyringone for 7 days at 20° C. in the dark. After 7 days, the embryos are transferred to standard culture medium (MS salts with N6 macronutrients, 1 mg/L 2,4-D, 1 mg/L Dicamba, 20 g/L sucrose, 0.6 g/L glucose, 1 mg/L silver nitrate, and 100 mg/L carbenicillin) with 3 mg/L Bialaphos® as the selective agent. Plates are maintained at 28° C. in the dark and are observed for colony recovery with transfers to fresh medium every two to three weeks.

The problem of inefficient production of transgenic crop plants, especially, but not limited to maize and soybean, is addressed in the three examples below. These examples illustrate how the BI genes can be used to improve plant transformation efficiency.

Example 6

Transient Zm-BI Expression Stimulates DNA Replication and Enhances Transgene Integration Regardless of the method of DNA delivery, cells competent for the integration of foreign DNA must be actively dividing. There is a growing body of evidence suggesting that integration of foreign DNA occurs in dividing cells (this includes both Agrobacterium and direct DNA delivery methods). It has long been observed that dividing transformed cells represent only a fraction of cells that transiently express a transgene. It is well known (in non-plant systems) that the delivery of damaged DNA, (similar to what we introduce by particle gun delivery methods) induces an immediate cell cycle arrest and often triggers events leading to apoptosis. This cessation of the cell cycle and stimulation of apoptosis can be reversed by ectopic transient over-expression of positive cell cycle regulators, or by inhibitors of apoptosis. The overall result will be a stimulation of the cell cycle which will increase integration frequencies.

To demonstrate this, a Zm-BI or Gm-BI gene is cloned into a cassette with a constitutive promoter (i.e. either a strong maize promoter such as the ubiquitin promoter including the first ubiquitin intron, or a weak constitutive promoter such as nos). Delivery of the BI gene in an appropriate plant expression cassette (for example, in a UBI::BI::pinII-containing plasmid) along with UBI::bar::pinII can be accomplished through particle bombardment or Agrobacterium-mediated transformation. DNA is introduced into maize cells capable of growth on suitable maize culture medium. Such competent cells can be from maize suspension culture, callus culture on solid medium, freshly isolated immature embryos or meristem cells. Immature embryos of the PHP38 genotype are used as the target for co-delivery of these two plasmids. Transient expression of the BI gene inhibits apoptosis and increases the proportion of cells that can progress through the cell cycle, thus increasing the proportion of recipient-cells (i.e. into which DNA was introduced) that enter S-phase.

This stimulation through the G1/S transition in cells harboring transgenic plasmid DNA provides an optimal cellular environment for integration of the introduced genes. Cytological methods can be used to verify increased frequencies of progression through S-phase and mitosis (i.e. for cells in which a visual marker such as GFP was transformed alongside BI, the green fluorescent cells will exhibit a higher mitotic index). Cells in S-phase (undergoing DNA replication) can be monitored by detecting nucleotide analog incorporation. For example, following incubation of cells with bromodeoxyuridine (BrdU) incorporation of this thymadine analog can be detected by methods such as antiBrdU immunocytochemistry or through enhancement of Topro3 fluorescence following BrdU labeling. BI expression will increase the proportion of cells incorporating BrdU (i.e. a higher percentage of transformed cells will incorporate BrdU relative to untransformed cells). Increased DNA synthesis can also be monitored using such methods as fluorescence activated cell sorting (FACS) of protoplasts (or nuclei), in conjunction with appropriate BrdU-insensitive fluorescent DNA labels such as propidium iodide and DAPI or BrdU-detecting methods described above. For example, tissue is homogenized to release nuclei that are analyzed using the FACS for both green fluorescence (from our accompanying GFP marker) and DNA content. Such analysis can not only determine stages of the cell cycle but can be used to quantify the proportion of the cell population undergoing apoptosis. Such FACS analysis demonstrates that expression of a co-transformed GFP reporter correlates with BI induced reduction in the proportion of cells exhibiting signs of apoptosis such as chromosomal DNA fragmentation and changes in mitochondrial permeability. Similar experiments can be run using the fluorescently labeled anti-BrdU antisera to demonstrate that BI expression increased the percentage of cells in S-phase. Cell cycle stage-specific probes can also be used to monitor cell cycle progression. For example, numerous spindle-associated proteins are expressed during a fairly narrow window during mitosis, and antibodies or nucleic acid probes to cyclins, histones, or DNA synthesis enzymes can be used as positive markers for the G1/S transition. For cells that have received the BI gene cassette, changes in the cell population receiving DNA is manifested in a decrease in apoptotic cells (which can be verified by flow cytometry) and an increased mitotic index (detected by staining for mitotic figures using a DNA dye such as DAPI or Hoechst 33258).

To assess the effect on transgene integration, growth of bialaphos-resistant colonies on selective medium is a reliable assay. Within 1–7 days after DNA introduction, the embryos are moved onto culture medium containing 3 mg/l of the selective agent bialaphos. Embryos, and later callus, are transferred to fresh selection plates every 2 weeks. After 6–8 weeks, transformed calli are recovered. Transgenic callus containing the introduced genes can be verified using PCR and Southern analysis. Northern analysis can also be used to verify which calli are expressing the bar gene, and whether the BI gene is being expressed at levels above normal wild-type cells (based on hybridization of probes to freshly isolated mRNA population from the cells). In immature embryos that had transient, elevated BI expression, higher numbers of stable transformants are recovered (likely a direct result of increased integration frequencies). Increased transgene intregration frequency can also be assessed using such well-established labeling methods such as in situ hybridization.

For this specific application (using transient BI-mediated cell cycle stimulation to increase transient integration frequencies), it may be desirable to reduce the likelihood of ectopic stable expression of the BI gene. Strategies for transient-only expression can be used. This includes delivery of RNA (transcribed from the BI gene) or BI protein along with the transgene cassettes to be integrated to enhance transgene integration by transient stimulation of cell division. Using well-established methods to produce in vitro BI-RNA, this can then be purified and introduced into maize cells using physical methods such as microinjection, bombardment, electroporation or silica fiber methods. For protein delivery, the gene is first expressed in a bacterial or baculoviral system, the protein purified and then introduced into maize cells using physical methods such as microinjection, bombardment, electroporation or silica fiber methods. Alternatively, BI proteins are delivered from Agrobacterium tumefaciens into plant cells in the form of fusions to Agrobacterium virulence proteins. Fusions are constructed between BI and bacterial virulence proteins such as VirE2, VirD2, or VirF which are known to be delivered directly into plant cells. Fusions are constructed to retain both those properties of bacterial virulence proteins required to mediate delivery into plant cells and the BI activity required for enhancing transgene integration. This method ensures a high frequency of simultaneous co-delivery of T-DNA and functional BI protein into the same host cell. The methods above represent various means of using the BI gene or its encoded product to transiently stimulate DNA replication and cell division, which in turn enhances transgene integration by providing an improved cellular/molecular environment for this event to occur.

Example 7

Altering BI Expression Stimulates the Cell Cycle and Growth

Based on results in other eukaryotes, expression of BI genes inhibits apoptosis and thus increases the proportion of cells that can continue to divide. This increase in division rate is assessed in a number of different manners, being reflected in smaller cell size, more rapid incorporation of radiolabeled nucleotides, and faster growth (i.e. more biomass accumulation). Delivery of the BI in an appropriate plant expression cassette is accomplished through particle bombardment or *Agrobacterium*-mediated transformation. Through inhibition of apoptosis, BI gene expression improves the cellular environment for integration of introduced genes (as per Example 1). This will trigger a tissue culture response (cell divisions) in genotypes that typically do not respond to conventional culture techniques, or stimulate growth of transgenic tissue beyond the normal rates observed in wild-type (non-transgenic) tissues. This will also improve the culture response during selection protocols (i.e. the application of chemical selection to favor growth of transformants). The inhibition of apoptosis during this stressful period will stimulate growth beyond levels normally observed during the selection process.

To demonstrate this, the BI gene is cloned into a cassette with a constitutive promoter (i.e. either a strong maize promoter such as the ubiquitin promoter including the first ubiquitin intron, or a weak constitutive promoter such as nos). Either particle-mediated 93 DNA delivery or *Agrobacterium*-mediated delivery are used to introduce the UBI:: BI::pinII-containing plasmid along with a UBI::bar::pinII-containing plasmid into maize cells capable of growth on suitable maize culture medium. Such competent cells can be from maize suspension culture, callus culture on solid medium, freshly isolated immature embryos or meristem cells. Immature embryos of the PHP38 genotype are used as the target for co-delivery of these two plasmids, and within 1–7 days the embryos are moved onto culture medium containing 3 mg/l of the selective agent bialaphos. Alternately, instead of using chemical selection to identify transformants, a more vigorous growth pattern identifies the transformants (see Example 9).

Embryos, and later callus, are transferred to fresh selection plates every 2 weeks. After 6–8 weeks, transformed calli are recovered. In treatments where both the bargene and BI gene have been transformed into immature embryos, a higher number of growing calli are recovered on the selective medium and callus growth is stimulated (relative to treatments with the bar gene alone). Transgenic callus can be verified using PCR and Southern analysis. Northern analysis can also be used to verify which calli are expressing the bar gene, and which are expressing the BI gene at levels above normal wild-type cells (based on hybridization of probes to freshly isolated mRNA population from the cells).

Inducible Expression Variation. The BI gene can also be cloned into a cassette with an inducible promoter such as the benzenesulfonamide-inducible promoter. The BI expression vector is co-introduced into plant cells with a marker containing vector and after selection on bialaphos, the transformed cells are exposed to the safener (inducer). This chemical induction of BI expression results in decreased apoptosis and a overall stimulation of growth. The cells are screened for the presence of BI RNA by northern, or RT-PCR (using transgene specific probes/oligo pairs), for BI-encoded protein using BI-specific antibodies in Westerns or using hybridization. Increased DNA replication is detected using BrdU labeling followed by antibody detection of cells that incorporated this thymidine analogue. Likewise, other cell cycle division assays could be employed, as described above.

Example 8

BI Expression Resulted in Increased Growth Rates, Which Could be used as a Screening Criterion for Positive Selection of Transformants Using two promoters of increasing strength to drive BI expression in maize, BI stimulates more rapid callus growth over control treatments, and the stronger promoter driving BI results in faster growth than with the low-level promoter. For example, an experiment is performed to compare the nos and UBI promoters. As noted above, based on our experience with these two promoters driving other genes, the In2 promoter (in the absence of an inducer other than auxin from the medium) would drive expression at very low levels. The nos promoter has been shown to drive moderately-low levels of transgene expression (approximately 10- to 30-fold lower than the maize ubiquitin promoter). One control treatment is used in this experiment, the UBI:PAT~GFPmo:pinII construct by itself (with no BI). PHP38 immature embryos are bombarded as previously described, and transgenic, growing events are scored at 3 and 6 weeks. The control treatment results in a transformation frequency of 0.5 to 3.0%. In2: BI, nos:BI and UBI:BI treatments result in substantially higher transformation frequencies, with the improvement (relative to the control) being greatest in the treatment with the stronger promoter (UBI).

Within these treatments we also expect there to be an increase in the overall frequency of vigorously growing calli, relative to the control treatment, again with the stronger promoter results in the greatest increase in growth rate.

Example 9

Re-transformation of BI-transgenic Progeny Results in Elevated Transformation Frequency of PHP38

*Agrobacterium* mediated transformation As the starting point for Agrobacterium-mediated re-transformation experiments, regenerated PHP38 T0 transformants are produced containing maize BI-1 expression cassettes and UBI:: moPAT~GFP::pinII. The BI-1 expression cassette with the nopaline synthase promoter from *Agrobacterium tumefaciens* (Shaw et al., *Nucl. Acids Res.* 12:7831–7846, 1984) or modified nos promoters is described below. The PAT~GFP cassette contains a maize-optimized gene encoding phosphinothricin acetyltransferase (moPAT, see WO 98/30701) followed by a sequence encoding 4×(GSSS), a flexible polypeptide linker of GLY-SER-SER-SER, and then a maize-optimized nucleic acid sequence encoding Green Fluorescence Protein (GFP; see WO 98/01575). This PAT~GFP fusion construct is driven by the maize ubiquitin promoter (Christensen et al., *Plant Mol. Biol.* 18:675–689, 1992) and contains a potato proteinase inhibitor II3' sequence (An et al., *Plant Cell* 1:115–122, 1989).

Transgenic PHP38 plants containing a co-segregating BI-1 expression cassette and the UBI::PAT~GFP expression cassette are crossed to wild-type (non-transformed) PHP38 plants (using the non-transformed parent as the pollen donor). As expected from such a cross, the developing embryos on these ears segregate either for transgene expression or wild-type. Immature embryos are harvested 12 days after pollination and transformed with an *Agrobacterium* binary plasmid containing UBI::moCAH::pinII (moCAH is a maize optimized [for codon usage] gene that encodes for the *Myrothecium verrucaria* cyanamide hydratase protein [CAH] that can hydrate cyanamide to non-toxic urea). A standard *Agrobacterium*-mediated transformation protocol (U.S. Pat. No. 5,981,840) adapted for cyanamide selection (see WO 98/30701) is used, with additional modifications listed below. *Agrobacterium* is grown to log phase in liquid minimal-A medium containing 100 μM acetosyringone and spectinomycin. Embryos are immersed in a log phase suspension of *Agrobacterium* adjusted to obtain $3\times10^8$ CFU's/ml. Embryos are then co-cultured on culture medium with acetosyringone for 3 days at 20° C. After 3 days the embryos are returned to standard culture medium with 100 mg/l carbenicillin added to kill residual *Agrobacterium*. After an additional 4 days the segregating embryos are divided into GFP positive and GFP negative populations and moved to fresh culture medium with 50 mg/l cyanamide for selection. After 8 weeks the numbers of transformed colonies are determined.

Since the PAT~GFP and BI-1 expression cassettes are co-segregating, GFP expression is used to separate segregating transgenic (PAT~GFP+/BI-1+) and non-transgenic (wild-type) embryos after *Agrobacterium*-mediated transformation, and then these separate populations are cultured and selected as independent groups. Using embryos from different ears co-segregating for GFP and BI-1, we expect the BI-1-containing embryos to exhibit a much higher transformation frequency demonstrating that ectopic BI-1 expression improves re-transformation frequencies. For ears from which the wild-type embryos (non-transgenic segregants) produce very low levels (or no) transformants, we expect the GFP+/BI-1-containing embryos from the same ears to produce cyanamide-resistant transformants at approximately a 5–10% frequency. In ears in which the wild-type, non-transformed embryos produce higher levels of transformants (for example, upwards of 10%), we expect the transformation frequencies from the BI-1 expressing embryos to be elevated to even greater levels, i.e. upwards of 30–40%.

Particle gun transformation re-transformations. As the starting point for particle gun-mediated re-transformation experiments, regenerated PHP38 T0 transformants are produced containing maize BI-1 expression cassettes and UBI::moPAT~GFP::pinII. Transformants containing UBI::moPAT~GFP::pinII and BI-1 expression cassettes are tested; with BI-1 being driven by a nos promoter. As a control, a non-functional version of BI-1 is used, in which the BI-1 coding sequence is frame-shifted by 1 position after the START codon, resulting in essentially the same mRNA species but producing a non-functional protein. Expression of this frame-shifted sequence (abbreviated "f-shift" below) is driven by the nos promoter. As mentioned above for the functional BI-1 genes, this f-shift BI-1 cassette co-segregates with GFP in the T1 progeny embryos.

Transgenic PHP38 plants containing a co-segregating BI-1 expression cassette and the UBI::PAT~GFP expression cassette are crossed to wild-type (non-transformed) PHP38 plants (using the non-transformed parent as the pollen donor). As expected from such a cross, the developing embryos on these ears segregate either for transgene expression or wild-type. Embryos co-segregating for GFP and BI-1 (functional and frame-shift (fs) versions) are transformed using a particle gun using the standard immature embryo bombardment transformation protocol (Songstad D. D. et al., In Vitro Cell Dev. Biol. Plant 32:179–183, 1996). Cells are transformed by culturing maize immature embryos (approximately 1–1.5 mm in length) onto 560P medium containing N6 salts, Erikksson's vitamins, 0,69 g/l proline, 2 mg/l 2,4-D and 3% sucrose. After 4–5 days of incubation in the dark at 28° C., embryos are removed from 560P medium and cultured, scutellum up, onto 560Y medium which is equivalent to 560P but contains 12% sucrose. Embryos are allowed to acclimate to this medium for 3 h prior to transformation. The scutellar surface of the immature embryos is targeted using particle bombardment with a ubi:moCAH:pinII plasmid. Embryos are transformed using the PDS-1000 Helium Gun from Bio-Rad at one shot per sample using 650 P.S.I. rupture disks. DNA delivered per shot averages at 0.1667 ug. Following bombardment, all embryos are maintained on 560L medium (N6 salts, Eriksson's vitamins, 0.5 mg/l thiamine, 20 g/l sucrose, 1 mg/l 2,4-D, 2.88 g/l proline, 2.0 g/l gelrite, and 8.5 mg/l silver nitrate). After 2–7 days post-bombardment, all the embryos from both treatments are transferred onto N6-based medium containing 50 mg/l cyanamide (Pioneer 560P medium described above, with 50 mg/l cyanamide). Plates are maintained at 28° C. in the dark and are observed for colony recovery with transfers to fresh medium occurring every two to three weeks. Early in the sub-culture regime, GFP+ and GFP− embryos are separated. These two sub-populations are subsequently cultured and analyzed as separate treatments. The PAT~GFP expression cassette and the BI-1 expression cassette co-segregate together, and thus the presence of GFP expression is used to separate BI-1+ and BI-1− progeny for analysis.

Comparing PAT~GFP+/BI-1+transgenic embryos with wild-type (non-transgenic) embryos from the same ear we expect will show that the overall recovery of cyanimide-resistant transformants is much higher for the BI-1 transgenic embryos. For ears from PAT~GFP+/BI-1fs transgenic plants (containing the frame-shift control) we expect there to be no significant improvement in transformation frequencies over segregating wild-type embryos.

Example 10

Using the GmBI1 Gene to Improve Soybean Transformation

Delivery of the GmBI (the soybean BI) gene can be accomplished through numerous well-established methods for plant cells, including for example particle bombardment, sonication, PEG treatment or electroporation of protoplasts, electroporation of intact tissue, silica-fiber methods, microinjection or Agrobacterium-mediated transformation. Using one of the above methods, DNA is introduced into soybean cells capable of growth on suitable soybean culture medium. The BI gene (GmBI1) is cloned into a cassette with a constitutive promoter (for example, the SCP-1 promoter which confers constitutive expression in soybean, see PHI Patent application WO 99/43838) and a 3' sequence such as the nos 3' region. Particle bombardment is used to introduce the SCP1::GmBI1:: nos-containing plasmid along with a SCP1::HYG::nos-containing plasmid (which, when expressed produces a protein which confers hygromycin resistance) into soybean cells capable of growth on suitable soybean culture medium. Such competent cells can be from soybean suspension culture, cell culture on solid medium, freshly isolated cotyledonary nodes or meristem cells. Suspension-cultured somatic embryos of Jack, a *Glycine max* (I.) Merrill cultivar, are used as the target for co-delivery of a BI1 and a HYG-expressing plasmid. For target tissues receiving the BI1 expression cassette, transformation frequency is improved. Media for induction of cell cultures with high somatic embryogenic capacity, for establishing suspensions, and for maintenance and regeneration of somatic embryos are described (Bailey M A, Boerma H R, Parrott W A, 1993 *Genotype effects on proliferative embryogenesis and plant regeneration of soybean, In Vitro Cell Dev Biol* 29P: 102–108). Likewise, methods for particle-mediated transformation of soybean are well established in the literature, see for example Stewart N C, Adang M J, All J N, Boerma H R, Cardineau G, Tucker D, Parrott W A, 1996, Genetic transformation, recovery and characterization of fertile soybean transgenic for a synthetic Bacillus thuringiensis crylAc gene, *Plant Physiol* 112:121–129.

Maintenance of Soybean Embryogenic Suspension Cultures

Soybean embryogenic suspension cultures are maintained in 35 ml liquid media SB196 or SB172 in 250 ml Erlenmeyer flasks on a rotary shaker, 150 rpm, 26C with cool white fluorescent lights on 16:8 hr day/night photoperiod at light intensity of 30–35 uE/m2 s.

Cultures are subcultured every two weeks by inoculating approximately 35 mg of tissue into 35 ml of fresh liquid media. Alternatively, cultures are initiated and maintained in 6-well Costar plates.

SB 172 media is prepared as follows: (per liter), 1 bottle Murashige and Skoog Medium (Duchefa # M 0240), 1 ml B5 vitamins 1000×stock, 1 ml 2,4-D stock (Gibco 11215–019), 60 g sucrose, 2 g MES, 0.667 g L-Asparagine anhydrous (GibcoBRL 11013–026), pH 5.7

SB 196 media is prepared as follows: (per liter) 10 ml MS FeEDTA, 10 ml MS Sulfate, 10 ml FN-Lite Halides, 10 ml FN-Lite P, B, Mo, 1 ml B5 vitamins 1000×stock, 1 ml 2,4-D, (Gibco 11215–019), 2.83 g $KNO_3$, 0.463 g $(NH_4)_2SO_4$, 2 g MES, 1 g Asparagine Anhydrous, Powder (Gibco 11013–026), 10 g Sucrose, pH 5.8.

2,4-D stock concentration 10 mg/ml is prepared as follows: 2,4-D is solubilized in 0.1 N NaOH, filter-sterilized, and stored at $-20°$ C.

B5 vitamins 1000×stock is prepared as follows: (per 100 ml)—store aliquots at $-20°$ C., 10 g myo-inositol, 100 mg nicotinic acid, 100 mg pyridoxine HCl, 1 g thiamine.

Particle Bombardment

Soybean embryogenic suspension cultures are transformed with various plasmids by the method of particle gun bombardment (Klein et al. 1987; *Nature* 327:70.

To prepare tissue for bombardment, approximately two flasks of suspension culture tissue that has had approximately 1 to 2 weeks to recover since its most recent subculture is placed in a sterile 60×20 mm petri dish containing 1 sterile filter paper in the bottom to help absorb moisture. Tissue (i.e suspension clusters approximately 3–5 mm in size) is spread evenly across each petri plate. Residual liquid is removed from the tissue with a pipette, or allowed to evaporate to remove excess moisture prior to bombardment. Per experiment, 4–6 plates of tissue are bombarded. Each plate is made from two flasks.

To prepare gold particles for bombardment, 30 mg gold is washed in ethanol, centrifuged and resuspended in 0.5 ml of sterile water. For each plasmid combination (treatments) to be used for bombardment, a separate micro-centrifuge tube is prepared, starting with 50 µl of the gold particles prepared above. Into each tube, the following are also added; 5 µl of plasmid DNA (at 1 µg/µl), 50µl $CaCl_2$, and 20µl 0.1 M spermidine. This mixture is agitated on a vortex shaker for 3 minutes, and then centrifuged using a microcentrifuge set at 14,000 RPM for 10 seconds. The supernatant is decanted and the gold particles with attached, precipitated DNA are washed twice with 400 µl aliquots of ethanol (with a brief centrifugation as above between each washing). The final volume of 100% ethanol per each tube is adjusted to 40 ul, and this particle/DNA suspension is kept on ice until being used for bombardment.

Immediately before applying the particle/DNA suspension, the tube is briefly dipped into a sonicator bath to disperse the particles, and then 5 µg of DNA prep is pipetted onto each macro-carrier and allowed to dry. The macro-carrier is then placed into the DuPont® Biolistics PDS1000/HE gun. Using the DuPont® Biolistic PDS1000/HE instrument for particle-mediated DNA delivery into soybean suspension clusters, the following settings are used. The membrane rupture pressure is 1100 psi. The chamber is evacuated to a vacuum of 27–28 inches of mercury. The tissue is placed approximately 3.5 inches from the retaining/stopping screen (3rd shelf from the bottom). Each plate is bombarded twice, and the tissue clusters are rearranged using a sterile spatula between shots.

Following bombardment, the tissue is re-suspended in liquid culture medium, each plate being divided between 2 flasks with fresh SB196 or SB172 media and cultured as described above. Four to seven days post-bombardment, the medium is replaced with fresh medium containing 25 mg/L hygromycin (selection media). The selection media is refreshed weekly for 4 weeks and once again at 6 weeks. Weekly replacement after 4 weeks may be necessary if cell density and media turbidity is high.

Four to eight weeks post-bombardment, green, transformed tissue may be observed growing from untransformed, necrotic embryogenic clusters. Isolated, green tissue is removed and inoculated into 6-well microtiter plates with liquid medium to generate clonally-propagated, transformed embryogenic suspension cultures.

Each embryogenic cluster is placed into one well of a Costar 6-well plate with 5 mls fresh SB196 media with 25 mg/L hygromycin. Cultures are maintained for 2–6 weeks with fresh media changes every 2 weeks. When enough tissue is available, a portion of surviving transformed clones are subcultured to a second 6-well plate as a back-up to protect against contamination.

In treatments where both the HYG and BI1 expression cassettes are transformed into immature embryos, a higher number of growing embryogenic cultures are expected on the selective medium and growth of embryogenic cultures is stimulated (relative to treatments with the HYG gene alone).

Regeneration of Soybean Somatic Embryos

To promote in vitro maturation, transformed embryogenic clusters are removed from liquid SB196 and placed on solid agar media, SB 166, for 2 weeks. Tissue clumps of 2–4 mm size are plated at a tissue density of 10 to 15 clusters per plate. Plates are incubated in diffuse, low light (<10 µE) at 26+/−1° C. After two weeks, clusters are subcultured to SB 103 media for 3–4 weeks.

SB 166 is prepared as follows: (per liter), 1 pkg. MS salts (Gibco/BRL—Cat# 11117–017), 1 ml B5 vitamins 1000× stock, 60 g maltose, 750 mg MgCl2 hexahydrate, 5 g activated charcoal, pH 5.7, 2 g gelrite.

SB 103 media is prepared as follows: (per liter), 1 pkg. MS salts (Gibco/BRL—Cat# 11117–017), 1 ml B5 vitamins 1000× stock, 60 g maltose, 750 mg MgCl2 hexahydrate, pH 5.7, 2 g gelrite.

After 5–6 week maturation, individual embryos are desiccated by placing embryos into a 100×15 petri dish with a 1 cm2 portion of the SB103 media to create a chamber with enough humidity to promote partial desiccation, but not death.

Approximately 25 embryos are desiccated per plate. Plates are sealed with several layers of parafilm and again are placed in a lower light condition. The duration of the desiccation step is best determined empirically, and depends on size and quantity of embryos placed per plate. For example, small embryos or few embryos/plate require a shorter drying period, while large embryos or many embryos/plate require a longer drying period. It is best to check on the embryos after about 3 days, but proper desiccation will most likely take 5 to 7 days. Embryos will decrease in size during this process.

Desiccated embryos are planted in SB 71–1 or MSO medium where they are left to germinate under the same culture conditions described for the suspension cultures. When the plantlets have two fully-expanded trifoliolate leaves, germinated and rooted embryos are transferred to sterile soil and watered with a half-strength MS-salt solution. Plants are grown to maturity for seed collection and analysis. Embryogenic cultures from the BI1 treatment are expected to regenerate easily. Healthy, fertile transgenic plants are grown in the greenhouse. Seed-set on BI1 transgenic plants is expected to be similar to control plants, and transgenic progeny are recovered.

SB 71–1 is prepared as follows: 1 bottle Gamborg's B5 salts w/sucrose (Gibco/BRL—Cat# 21153–036), 10 g sucrose, 750 mg MgCl2 hexahydrate, pH 5.7, 2 g gelrite.

MSO media is prepared as follows: 1 pkg Murashige and Skoog salts (Gibco 11117–066), 1 ml B5 vitamins 1000× stock, 30 g sucrose, pH 5.8, 2 g Gelrite.

It is expected that higher BI1-transgene expression levels improve transformation. For this bombardment experiment (to be performed in a similar manner to that described above), soybean suspension cultures are used as the target tissue for bombardment. The treatments include a no-BI control (SCP1:: HYG::nos), or the SCP1:: HYG::nos marker plus one of two BI-expressing plasmids (SCP1:: BI1::nos or nos::BI::nos). For this experiment high levels of BI expression (SCP1) are compared to low levels (nos) of expression. When the SCP1 promoter drives the expression of BI, the transformation frequencies are expected increase. Placing the BI1 gene behind the nos promoter is expected to produce a transformation frequency intermediate to the SCP1:: BI1 frequency and that of the control treatment. It is expected that higher expression levels result in correspondingly higher recovery of transformants.

Example 11

Engineering Resistance Against Maize Ear Mold Disease

A number of fungal pathogens, such as *Fusarium moniliforme*, cause ear mold in maize. *Fusarium moniliforme* growth in maize appears dependent on the presence of dead, senescing or decaying tissues. Among the dead or decaying tissue that are often so exploited by *Fusarium* are silks, husks, pericarp or the cob. Tissues that are still alive are somehow recalcitrant to Fusarium ingress. Exactly why this is so remains unknown at this time. However, this dependency of Fusarium upon dead tissue availability, could be turned into an advantage for improving maize resistance to it, if death or senescence of tissues can be delayed.

Consequently, to the extent that the inventive maize BI genes claimed herein can control cell death in maize, they can be used to enhance ear mold resistance. To that end, any one of these BI genes, or other related inventive genes of this patent, could be used in crop plants, especially maize, to retard cell death and senescence. Ideally this would be done by driving the expression of the BI genes with tissue-preferred promoters in a transgenic plant—especially promoters specific to the tissue most accounting for ear mold ingress, namely silks, husks, pericarp or the cob. Work had already occurred and is continuing to identify and characterize such promoters. Additionally, other promoters, such as those for senescence-induced genes, such as a cysteine protease, could be used to bump up the expression of the BI when senescence begins. Upon elevation of the BI expression by this promoter, the senescence process and cell death will be retarded. Accordingly, ear mold resistance will be gained.

Example 12

Developing General Increased Tolerance to Diseases in Maize and other Crop Plants Plant disease symptoms usually result from cell death in infected tissues. The cause of this death can be two fold: a) direct death-inflicting activity by the pathogens, such as by their production of antibiotic (here anti-plant) compounds or proteins; and b) cell death resulting from activation of the plants' own cell death mechanisms—something that is intrinsic to many of the plants' responses to pathogens. Some pathogens (such as Sclerotinia, Helminthosporium sp., Botrytis etc.) first actively kill the plant tissue and then colonize it, and they can also take advantage of any cell death resulting from activation of the plants' own defense system.

For these reasons, genes which would suppress the initiation and/or the spread of cell death following infection, would help alleviate the damage done by pathogenic organisms, regardless of these two sources. The BI presented here are one such class of genes. A promoter that could drive the BI gene expression in the tissue that is infected by the pathogens would be of choice. In some situations a constitutive promoters such as ubiquitin could be used to drive BI expression constitutively, and therefore keep the plant on guard against cell death and cover many possible tissues that may become infected. In another strategy, promoters for genes known to be expressed in particular tissues can be chosen where the pathogen of interest is known to target particular tissues. Alternatively, or in addition to the tissue-specificity of the promoter, a defense-inducible or death-inducible promoter would be chosen. The expression of a number of maize genes is induced following pathogen attack and many of these are induced in association with necrosis that results from such infection. The promoters for these genes could be used to drive the expression of the BI genes. The expected outcome of this is that upon pathogen attack, the death process is turned on. This then will result in the elevated (ectopic) expression of the BI genes. The expression of these BI genes will then result in a retardation of the initiation of death, or if initiated already, it will retard the spread of the death. In this way, the Bax-inhibitor (BI) gene expression will result in a lessening of the disease symptoms, for after all disease symptoms are in many cases largely a function of the extent of death. It is this death that causes, as in the case of leaf blights, a loss of photosynthetic capacity of the plant, and a corresponding decrease in yield.

Example 13

Use of the Maize BI-DR to Induce Male Sterility

Expression vectors useful for promoting apoptosis through the modulation of BI expression are those that down-regulate BI levels or activity (abbreviated hereafter as BI-DR constructs). A BI-DR construct is an expression cassette in which the transcribed RNA results in decreased levels of BI protein in the cell. Examples would include expressing antisense, expressing an inverted-repeat sequence (which will form a hairpin) constructed from a portion of the BI sequence, expressing the BI sequence fused to another such "hairpin" forming sequence, or expressing BI in a manner that will favor co-suppression of endogenous BI.

Maize expression cassettes directing BI-DR expression to tapetum can be constructed. An expression cassette directing expression of the BI-DR polynucleotide to the tapetum during microsporogenesis is made using the maize MS45 promoter (U.S. Pat. No. 6,037,523 issued Mar. 14, 2000). Embryos are co-bombarded with the selectable marker PAT fused to the GFP gene along with the tapetum-specific BI-DR expression cassette described above. Both inbred and Hi-II transformants are obtained and regenerated as described in examples 6 and 7 above.

It is anticipated that in the regenerated plants (and progeny obtained through the ear of such transgenic plants), induction of apoptosis in the tapetum during the microsporogenesis process will result in male sterility. Upon microscopic examination of the developing anthers it will be apparent that apoptosis has occurred by the death of the tapetal cell layer and abortion of microspores.

Example 14

Cell Death Assays

Gene-directed cell death can be detected using numerous methods. These include methods used to recognize characteristic patterns of morphological, biochemical and molecular changes. These are typically grouped into two broad categories. The first group is morphological changes such as nuclear fragmentation, condensation of cytoplasm, appearance of apoptotic bodies and ultimately phagocytosis of remains. The second group is functional or biochemical changes such as an increase in free calcium, cell dehydration, loss of mitochondrial membrane potential, proteolysis, phosphatidylserine externalization, DNA denaturation and fragmentation, intranucleosomal cleavage and protein cross-linkage.

Commonly used methods for detecting DNA fragmentation include ELISA methods, the TUNEL assay, gel electrophoresis methods, and flow cytometry. Methods are also well known for detecting increased apoptosis-associated proteins such as capsases and PARP. Cell integrity can be assessed using vital staining methods such as propidium iodide or Evan's Blue exclusion. One of the first sub-cellular changes that appear to trigger the cell death cascade is altered ionic balance and membrane potential across the mitochondrial membrane. Mitochondrial membrane potential can be measured using three cationic fluorescent probes, DiOC(6), JC-1, and TMRM. Commercial kits for the above assays currently exist for all of the above (see online catalog & information from CLONTECH™ or from ROCHE™) "both of which are incorporated by reference.

Example 15

Transformation and Regeneration of Maize Callus

Immature maize embryos from greenhouse grown High type II donor plants were bombarded with a plasmid containing a polynucleotide of the invention, ZmBI1–3. The ZmBI1–3 polynucleotide was operably linked to the constitutive promoter nos and the potato proteinase inhibitor 3' sequence (pinII). The plasmid containing nos::ZmBI1–3:: pinII was co-transformed along with a plasmid containing a fusion between a maize-optimized PAT selectable marker gene that confers resistance to the herbicide Bialaphos and a maize-optimized Green Fluorescent Protein (GFP). Transformation was performed as follows.

The ears were surface sterilized in 50% Chlorox bleach plus 0.5% Micro detergent for 20 minutes, and rinsed two times with sterile water. The immature embryos were excised and placed embryo axis side down (scutellum side up), 25 embryos per plate. These were cultured on 560 L medium (see Table 3 for medium formulations) 4 days prior to bombardment in the dark. Medium 560 L was an N6-based medium containing Eriksson's vitamins, thiamine, sucrose, 2,4-D, and silver nitrate. The day of bombardment, the embryos were transferred to 560 Y medium for 4 hours and were arranged within the 2.5-cm target zone. Medium 560Y was a high osmoticum medium (560L with high sucrose concentration).

The plasmid DNA containing the nos:BI1–3:: pinII expression cassette plus plasmid DNA containing the PAT~GFP fusion marker were precipitated onto 1.1 µm (average diameter) tungsten pellets using a $CaCl_2$ precipitation procedure as follows: 100 µl prepared tungsten particles (0.6 mg) in water, 20 µl (2 µg) DNA in Tris-EDTA buffer (1 µg total), 100 µl 2.5 M $CaCl_2$, 40 µl 0.1 M spermidine. As a control treatment, the Ubi::PAT~GFP:: pinII plasmid was co-precipitated with a second plasmid containing a Ubi::firefly luciferase::pinII cassette (keeping the ratios of PAT~GFP plasmid/total DNA consistent in both the control and BI-gene treatments).

Each reagent was added sequentially to the tungsten particle suspension. The final mixture was sonicated briefly. After the precipitation period, the tubes were centrifuged briefly, liquid removed, washed with 500 µl 100% ethanol, and centrifuged again for 30 seconds. Again the liquid was removed, and 60 µl 100% ethanol was added to the final tungsten particle pellet. For particle gun bombardment, the tungsten/DNA particles were briefly sonicated and 5 µl spotted onto the center of each macrocarrier and allowed to dry about 2 minutes before bombardment.

The sample plates were bombarded at a distance of 8 cm from the stopping screen to the tissue, using a Dupont™ biolistics helium particle gun. All samples received a single shot at 650 PSI, with a total of ten aliquots taken from each tube of prepared particles/DNA.

Four to twelve hours post bombardment, the embryos were moved to 560P (a low osmoticum callus initiation medium similar to 560L but with lower silver nitrate), for 3–7 days, then transferred to 560R selection medium, an N6 based medium similar to 560P containing 3 mg/liter Bialaphos, and subcultured every 2 weeks. Multicellular GFP cell clusters became visible after two weeks and their numbers were periodically recorded. After approximately 10 weeks of selection, selection-resistant GFP positive callus clones were sampled and PCR analysis was performed to confirm the presence of the nos::ZmBaxl1–3:: pinII cassette. As seen in Table 3 below, including the nos::BI1–3:: pinII plasmid resulted in a significant increase in transformation frequency (Student's T-test; p<0.05)

Table 3. Transformation results for immature embryos harvested from four ears and split equally between the control treatment (A) and the treatment including the BI gene (B). Transformation frequencies were calculated based on the number of bialaphos-resistant, GFP+ calli recovered per total number of embryos bombarded for a given treatment within an ear.

| Ear | Tx Events | Total Embryos | Tx Freq (%) |
|---|---|---|---|
| A. Control | | | |
| 1 | 1 | 75 | 1.3 |
| 2 | 5 | 75 | 6.7 |
| 3 | 9 | 100 | 9.0 |
| 4 | 13 | 100 | 13.0 |
| | | Mean | 7.5 |
| | | SD | 4.9 |
| B. nos::BI::pinII | | | |
| 1 | 12 | 75 | 16.0 |
| 2 | 8 | 75 | 10.7 |
| 3 | 17 | 100 | 17.0 |
| 4 | 13 | 100 | 13.0 |
| | | Mean | 14.2 |
| | | SD | 2.9 |

Positive lines were transferred to 288J medium, an MS-based medium with lower sucrose and hormone levels, to initiate plant regeneration. Following somatic embryo maturation (2–4 weeks), well-developed somatic embryos were transferred to medium for germination and transferred to the lighted culture room. Approximately 7–10 days later, developing plantlets were transferred to medium in tubes for 7–10 days until plantlets were well established. Plants were then transferred to inserts in flats (equivalent to 2.5" pot) containing potting soil and grown for 1 week in a growth chamber, subsequently grown an additional 1–2 weeks in the greenhouse, then transferred to Classic™ 600 pots (1.6 gallon)(#14–9674–9; Hummert International, Earth City, Mo.) and grown to maturity. Mature, normal-phenotype plants containing the nos::ZmBI1–3:: pinII cassette integrated into the genome were recovered.

What is claimed is:

1. An isolated polynucleotide comprising a member selected from the group consisting of:
   (a) a polynucleotide encoding the polypeptide of SEQ ID NO: 34;
   (b) the polynucleotide of SEQ ID NO:33; and
   (c) the polynucleotide which is complementary to a polynucleotide of (a) or (b);

wherein the polynucleotide of (a), (b) or (c), modulates Bax inhibitor activity.

2. An expression cassette comprising at least one polynucleotide of claim 1.

3. A transgenic plant cell comprising at least one expression cassette of claim 2.

* * * * *